United States Patent [19]

Feyen et al.

[11] 4,200,576
[45] Apr. 29, 1980

[54] BETA-LACTAM ANTIBIOTICS

[75] Inventors: Peter Feyen, Mettmann; Michael Preiss; Karl G. Metzger, both of Wuppertal, all of Fed. Rep. of Germany

[73] Assignee: Bayer Aktiengesellschaft, Leverkusen, Fed. Rep. of Germany

[21] Appl. No.: 862,466

[22] Filed: Dec. 20, 1977

[30] Foreign Application Priority Data

Dec. 24, 1976 [DE] Fed. Rep. of Germany ....... 2658718
Jun. 20, 1977 [DE] Fed. Rep. of Germany ....... 2727586

[51] Int. Cl.$^2$ .................. A61K 31/545; C07D 501/20
[52] U.S. Cl. .................. 424/246; 260/239.1; 424/248.4; 424/248.5; 424/248.51; 424/248.54; 424/256; 424/271; 542/420; 544/21; 544/22; 544/24; 544/25; 544/26; 544/27; 544/28; 544/317; 548/315; 548/316; 260/245.3
[58] Field of Search .................... 542/420; 544/21, 22, 544/24, 25, 26, 27, 28, 317; 548/315, 316; 260/239.1, 293.54, 307 A; 424/246, 248.4, 248.5, 248.51, 248.54, 256, 271, 272, 273

[56] References Cited

FOREIGN PATENT DOCUMENTS 767647 11/1971 Belgium .............................. 260/239.1
767648 11/1971 Belgium .............................. 260/239.1
2152968 4/1973 Fed. Rep. of Germany ........ 260/239.1

Primary Examiner—Bernard Helfin
Assistant Examiner—Vera C. Clarke
Attorney, Agent, or Firm—Sprung, Felfe, Horn, Lynch & Kramer

[57] ABSTRACT

Antibacterially active and animal feedstuff supplement β-lactam antibiotics of the formula

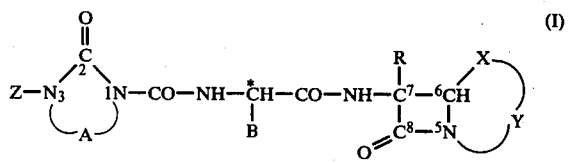

in which
R is H or —UR',
U is O or S,
R' is optionally substituted alkyl, alkenyl, alkinyl, aralkyl, aryl or cycloalkyl,
Z is

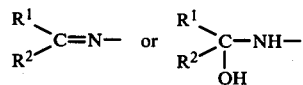

$R^1$ and $R^2$ individually are hydrogen or, individually or together with the carbon atom to which they are bonded, are any of various radicals,
A is —CH$_2$—CH$_2$—, —CH$_2$—CH$_2$—CH$_2$— or

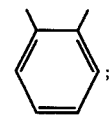

B is optionally substituted phenyl or is cyclohexenyl or cyclohexadienyl;
X is S, O, SO, SO$_2$ or —CH$_2$—; and
Y is a group of the formula

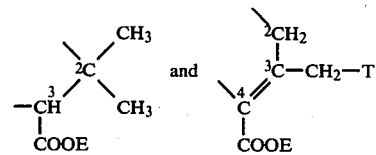

T is hydrogen, alkyl—CO—O—, pyridinium, aminopyridinium, carbamoyloxy, azido, cyano, hydroxyl or optionally substituted —S—phenyl, or is —S—Het,
in which
Het is an optionally substituted heterocyclic 5-membered or 6-membered ring;
and wherein
E is hydrogen, a radical forming, with the carboxyl group to which it is attached, a carboxy ester group, a cation of a salt, or a protective group, or a hydrate thereof. A process is also given for converting R directly from H to UR' employing a base, a halogenating agent and R'UH.

22 Claims, No Drawings

BETA-LACTAM ANTIBIOTICS

The present invention relates to certain new β-lactam compounds to a process for their preparation and to their use as medicaments, in particular as antibacterial agents and as agents for promoting the growth and for improving feedstuff utilisation in animals.

It has already been disclosed that certain α-(imidazolidin-2-oxo-1-yl-carbonylamino)-benzylpenicillins have an antibacterial action (compare Belgian Patent Specifications Nos. 767,647 and 767,648 as well as Netherlands Patent Specification No. 7,114,254 and German Offenlegungsschrift (German Published Specification) No. 2,152,968).

The new β-lactam antibiotics according to the invention differ chemically from the known compounds of the state of the art, above all, in that the $N_3$ of the imidazolidinone radical is bonded to the N atom of an imino group.

The present invention provides as new compounds β-lactams of formula I

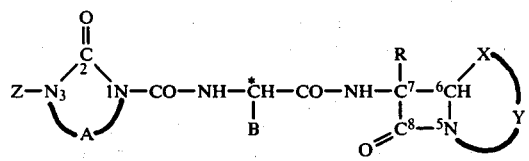

in which

R is hydrogen or a group —UR', in which

U is oxygen or sulphur and

R' is optionally substituted alkyl, alkenyl, alkinyl, aralkyl, aryl or cycloalkyl Z is a group of the formula

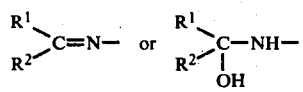

wherein $R^1$ and $R^2$ are the same or different and each is hydrogen, optionally substituted alkyl or alkenyl, optionally substituted cycloalkyl, cycloalkenyl or cycloalkadienyl, optionally substituted aralkyl, optionally substituted aryl, optionally substituted heterocyclyl, carboxyl, methoxycarbonyl, ethoxycarbonyl, cyano, nitro, lower alkylcarbonyl, —CONH₂, —CONHCH₃, —CON(CH₃)₂, —SO₂NH₂, —SO₂—NHCH₃ or —SO₂N(CH₃)₂, or $R^1$ and $R^2$, together with the carbon atom to which they are bonded, represent an optionally substituted 3-membered to 7-membered saturated or unsaturated carbocyclic or heterocyclic ring;

A is —CH₂—CH₂—, —CH₂—CH₂—CH₂— or

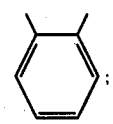

B is optionally substituted phenyl or is cyclohexenyl or cyclohexadienyl;

X is S, O, SO, SO₂ or —CH₂—; and

Y is a group of the formula

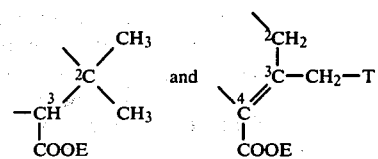

in which the carbon atom which carries the carboxyl group is bonded to the nitrogen atom of the β-lactam ring and T is hydrogen, alkyl—CO—O—, pyridinium, aminopyridinium, carbamoyloxy, azido, cyano, hydroxyl or optionally substituted —S—phenyl, or is —S—Het, in which Het is an optionally substituted heterocyclic 5-membered or 6-membered ring;

and wherein

E is hydrogen, a radical forming, with the carboxyl group to which it is attached, a carboxy ester group such as, for example, the pivaloyl group, a cation of a salt or is a suitable protective group; said β-lactams of formula I being optionally in either of the two possible R- and S-configurations, with respect to the chirality centre C*, and in the form of mixtures of the diastereomers resulting therefrom, and, when Z is a group of formula

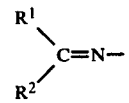

in which $R^1$ and $R^2$ are different, the β-lactams of formula I also being optionally in the syn form and/or in the anti form, with respect to the imino group, said β-lactams of formula I also being optionally in the form of one or more hydrate forms thereof.

Among the new β-lactam salts and esters of the invention, those salts and esters that are pharmaceutically acceptable are particularly important and are preferred.

Furthermore, it has been found that the compounds of the invention may be prepared by a process (process A), comprising reaction of a compound of formula II.

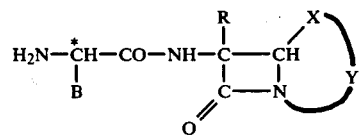

in which R, B, C*, X and Y have the same meaning as defined hereinbefore in formula I, with a compound of the formula III

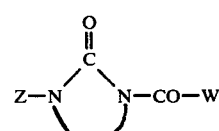

in which

Z and A have the same meaning as defined hereinbefore in formula I, and

W is halogen, azide or another nucleofugic leaving group, usually in the presence of a solvent, and optionally in the presence of an acid-binding agent, preferably at a temperature of from about $-20°$ C. to about $+50°$ C., and optionally converting the resulting $\beta$-lactam of formula I when in the form of a salt or ester into the free acid form or when in the form of an acid into a salt or ester.

The new $\beta$-lactam free acid and salt and ester forms of the general formula I can be interconverted in any suitable manner or method for such interconversion, known in the art.

In a further aspect the present invention provides a process (Process B) for the preparation of compounds of the general formula I in which Z, A, B, X and Y have the same meaning as first defined hereinbefore in formula I and R is a group —UR' in which U and R' have the same meaning as defined hereinbefore in formula I comprising treatment of a corresponding compund of the general formula I in which Z, A, B, X and Y have the same meaning as defined hereinbefore and R is H, and E is H or a cation, namely an organic or inorganic cation, with an excess of a base, preferably from 2 to 10 equivalents of base in the presence of 1 to 8 equivalents of a halogenating agent in an inert organic, preferably anhydrous, solvent and an excess of a compound of formula RH in which R is a group —UR' as defined hereinbefore preferably at a temperature below $-10°$ C.

In this form, the process differs significantly from the processes disclosed previously for the preparation of compounds of analogous structure, in which exclusively compounds with a protected carboxyl group were methoxylated.

It is to be regarded as decidedly surprising that virtually no side reactions, and only the stereospecific replacement at $C_6$ or $C_7$, occurs, even with sensitive penicillins and cephalosporins which contain unprotected functional groups.

The present state of the art regards protection of the carboxyl group as an essential prerequisite. Groups additionally present in the molecule (such as OH, NH and a further carboxyl group), which according to existing knowledge also had to be protected, likewise do not interfere with the reaction. The process according to the invention is without doubt unrivalled in its advantage of being a one-stage process and in its stereoselectivity and its high yields and is thus an important contribution to the art.

Surprisingly, the compounds of the invention exhibit a considerably higher and, above all, broader spectrum antibacterial action, effective against several families of bacteria in the Gram-negative range, than, for example, the $\beta$-lactam antibiotics knwon from the state of the art. Because of their powerful antibacterial properties and because of their ability to improve the growth of and feedstuff utilisation by animals, the compounds according to the invention are an important contribution to the art.

If, for example, D-$\beta$-aminobenzylpenicillin and 1-chlorocarbonyl-3-benzylideneimino-imidazolidin-2-one are used as the starting materials, the course of the reaction can be represented by the following equation:

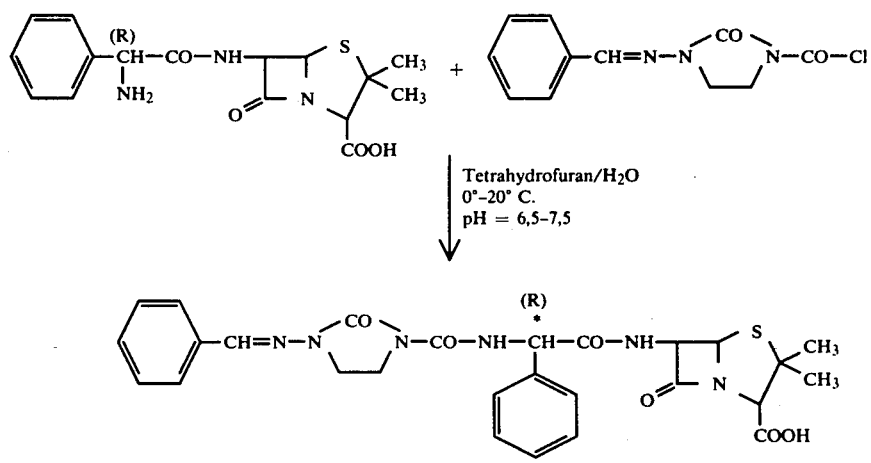

The equation which follows can be indicated as an example of the preparation of the substances according to the invention by the direct introduction of a group —UR' as first defined hereinbefore in formula I (R is not H), onto $C_6$ (or $C_7$ as appropriate) (Process B):

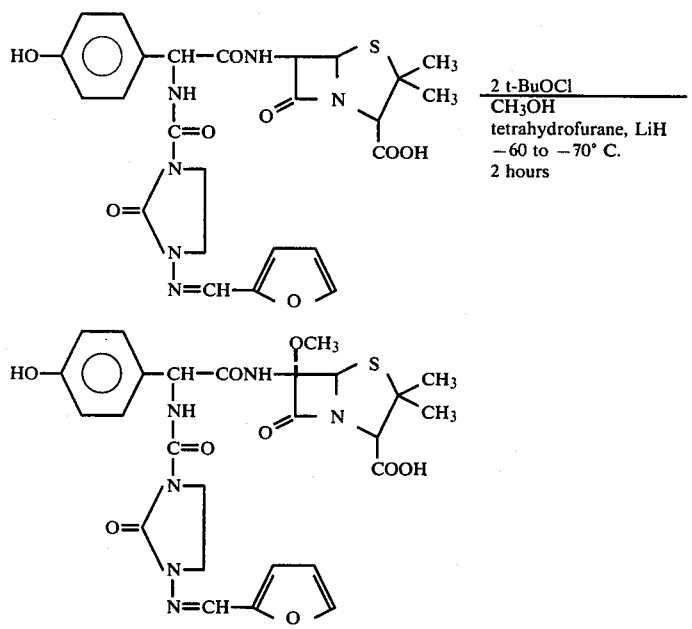

R' preferably is alkyl which is substituted by halogen, preferably chlorine and bromine, amino, monoalkylamino, dialkylamino, the alkyl substituents on the N atom of the amino group preferably each having 1 to 6 C atoms, or alkoxy having 1 to 6 C atoms; alkenyl having 3 to 6 C atoms, alkinyl having 3 to 6 C atoms, cycloalkyl having 3 to 7 C atoms or benzyl, phenyl or naphthyl.

However, the compounds in which R' is an unsubstituted alkyl radical having 1 to 4 C atoms, such as methyl, ethyl, n-propyl, i-propyl, n-butyl, i-butyl or —CH$_2$CH$_2$N(CH$_3$)$_2$ and U is oxygen are particularly preferred, and those in which —UR' is methoxy are especially preferred.

In the general formulae, R$^1$ and/or R$^2$ may each be an optionally substituted, straight-chain or branched, alkyl, having preferably 1 to 6, most preferably 1 to 4, carbon atoms. Examples which may be mentioned are optionally substituted methyl, ethyl, n- and i-propyl, and n-, i- and t-butyl. R$^1$ and/or R$^2$ may also each be an optionally substitute straight-chain or branched, alkenyl having preferably 2 to 6, most preferably 2 to 4, carbon atoms. Examples which may be mentioned are optionally substituted ethenyl, propen-1-yl, propen-2-yl, buten-3-yl and buten-2-yl-.

R$^1$ and/or R$^2$ may also each be an optionally substituted, monocyclic, bicyclic or tricyclic, cycloalky, cycloalkenyl or cycloalkadienyl, preferably containing 3 to 10, most preferably 3, 5 or 6 carbon atoms. Examples which may be mentioned are optionally substituted cyclopropyl, cyclobutyl, cyclopentyl, cyclopentenyl, cyclohexyl, cyclohexenyl, cyclohexadienyl, cycloheptyl, bicyclo-[2,2,1]-heptyl, bicyclo-[2,2,2]-octyl and adamantyl.

R$^1$ and R$^2$ may also each be optionally substituted aryl having preferably from 6 to 10 carbom atoms in the aryl moiety. Examples which may be mentioned are optionally substituted phenyl or naphthyl. Substituents in the phenyl ring may be in the o-position, m-position or p-position. The radicals may also be mentioned as further examples of R$^1$ and R$^2$.

R$^1$ and/or R$^2$ may also each be aralkyl, optionally substituted in the aryl moiety and/or alkyl moiety, having preferably 6 or 10, most preferably 6, carbon atoms in the aryl moiety and preferably from 1 to 4, most preferably 1 or 2, carbon atoms in the alkyl part, the alkyl moiety being straight-chain or branched. Examples which may be mentioned are optionally substituted benzyl and phenylethyl.

R$^1$ and R$^2$ may also each be optionally substituted, hetero-paraffinic, hetero-aromatic or hetero-olefinic, 5-membered to 7-membered, preferably 5-membered or 6-membered, rings having preferably from 1 to 3, most preferably 1 or 2 identical or different, hetero-atoms. The hetero-atom(s) may each be oxygen, sulphur or nitrogen. Examples of the heterocyclic groups which may be mentioned are optionally substituted thienyl, furyl, oxazolyl, isoxazolyl, thiazolyl, isothiazolyl, pyrrolyl, imidazolyl, pyrazolyl, oxdiazolyl, thiadiazolyl, triazolyl, oxtriazolyl, thiatriazolyl, tetrazolyl, pyridyl, pyrazinyl, pyrimidinyl, tetrahydrofuranyl, dioxanyl, pyrrolidinyl, piperidinyl, morpholinyl, pyronyl-2and pyronyl-4.

When R$^1$ and/or R$^2$ is/are alkyl, alkenyl, cycloalkyl, cycloalkenyl, cycloalkadienyl, aryl and aralkyl, the R$^1$ and/or R$^2$ group(s) can have one or more, preferably 1 to 3, most preferably 1 or 2, identical or different substituents R$^3$ as defined hereinbelow. Most preferably, the said radicals R$^1$ and R$^2$ are unsubstituted or contain one said substituent R$^3$.

When R$^1$ and/or R$^2$ is/are heterocyclyl, the R$^1$ and/or R$^2$ group(s) can have one or more, preferably 1 to 3, most preferably 1 or 2, identical or different substituents $R^4$ as defined hereinbelow. Most preferably a heterocyclyl $R^1$ or $R^2$ radical is unsubstituted or contains one substituent $R^4$, as defined hereinbelow.

In the following statements, the expression "lower alkyl" wherever it occurs, including when bonded to other atoms or groups (as for example in lower alkoxy, $$\underset{|}{\text{HCON}}-\text{(lower alkyl)},$$

and the like), denotes straight-chain or branched alkyl having preferably 1 to 6 most preferably 1 to 4, carbon atoms. Examples which may be mentioned are optionally substituted methyl, ethyl, n- and i-propyl and n-, i- and t-butyl. "Lower alkyl" can be substituted by 1 to 5, in particular 1 to 3, identical or different halogen atoms, halogen atoms being preferably fluorine, chlorine and bromine, especially fluorine and chlorine. Examples which may be mentioned are trifluoromethyl, chloro-di-fluoromethyl, bromomethyl, 2,2,2-tri-fluoroethyl and pentafluoroethyl.

$R^3$ may be an atom or a group and preferably is halogen, most preferably fluorine, chlorine, bromine or iodine, most desirably fluorine, chlorine or bromine; amino; amino-lower alkylamino, most preferably methylamino or ethylamino, most desirably methylamino; di-lower alkylamino, most preferably dimethylamino or diethylamino, most desirably dimethylamino; pyrrolidyl;piperidyl; HCO—NH—; lower alkyl—CO—NH—, most preferably $CH_3$—CO—NH—; H—CO—N (lower alkyl)—, most preferably H—CO—N($CH_3$)—or H—CO—N($C_2H_5$)—; lower alkyl —CO—N(lower alkyl)—, most preferably $CH_3$—CO—N($CH_3$)—; (lower alkyl)$_2$C=N—; lower alkyl—$SO_2$—NH—, most preferably $CH_3$—$SO_2$—NH—or $C_2H_5$—$SO_2$—NH—, most desirably $CH_3$—$SO_2$—NH—; lower alkyl —$SO_2$—N(lower alkyl)—, most preferably $CH_3$—$SO_2$—N($CH_3$)—; HO—$SO_2$—NH—; HO—$SO_2$—N(lower alkyl)—, most preferably HO—$SO_2$—N($CH_3$)— or HO—$SO_2$—N($C_2H_5$)—; amidino; (lower alkyl)$_2$ —N—CH=N—, especially $(CH_3)_2$N—CH=N—;

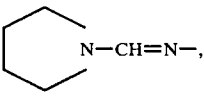

guanido, nitro, azido or hydroxyl, or lower alkyl-oxy-, most preferably $CH_3$—O— and $C_2H_5$—O—, most desirably $CH_3$—O—; H—CO—O—, or lower alkyl —CO—O—, most preferably $CH_3$—CO—O, $C_2H_5$—CO—O— or $(CH_3)_3$C—CO—O—; lower alkyl —O—CO—O—, most preferably $CH_3$ —O—CO—O—, $C_2H_5$—O—CO—O— or $(CH_3)_3$C—O—CO—O—; $H_2N$—CO—O—; lower alkyl—NH—CO—O—, most preferably $CH_3$—NH—CO—O— or $C_2H_5$—NH—CO—0—; (lower alkyl)-$_2$N—CO—O—, most preferably $(CH_3)_2$N—CO—O— or $(C_2H_5)_2$N—CO—O—,

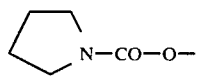

or $H_2N$—$SO_2$—O—; lower alkyl —NH—$SO_2$—O—, most preferably $CH_3$—NH—$SO_2$—O— or $C_2H_5$—NH—$SO_2$—O—; (lower alkyl)$_2$ N—$SO_2$—O—, most preferably $(CH_3)_2$ N—$SO_2$— —O— or $(C_2H_5)_2$ N—$SO_2$—O—; HOOC— or $H_2N$—CO—; (lower alkyl)-$_2$—N—CO—, most preferably $(CH_3)_2$N—CO— or $(C_2H_5)$N—CO—; OHC—, HO—$SO_2$—O—or HS—; lower alkyl—S—, most preferably $CH_3$—S—, $CF_3$—S—, $C_2H_5$—S— or $(CH_3)_2$CH—S—;

$$\underset{O}{\overset{\|}{\text{lower alkyl}-S-}}, \text{most preferably } \underset{O}{\overset{\|}{CH_3-S-}} \text{ or } \underset{O}{\overset{\|}{C_2H_5-S-}};$$

$HO_3S$—; lower alkyl—$SO_2$—, most preferably $CH_3$—$SO_2$—, $CF_3SO_2$— and $C_2H_5$—$SO_2$—; the group $H_2N$—$SO_2$—; lower alkyl —NH—$SO_2$—, most preferably $CH_3$—NH—$SO_2$— or $C_2H_5$—NH—$SO_2$—; (lower alkyl)$_2$ N—$SO_2$—, most preferably $(CH_3)_2$ N—$SO_2$— or $(C_2H_5)_2$ N—$SO_2$—;

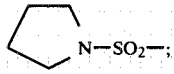

the group HO—$SO_2$—S—; straight-chain or branched alkyl having 1 to 6 carbon atoms, especially methyl, ethyl, propyl, isopropyl, n-butyl, sec.-butyl or tert.-butyl, most preferably methyl; or phenyl or phenoxy.

Each substituent $R^4$ may be an atom or group and preferably is lower alkyl, most preferably methyl, ethyl and isopropyl, especially methyl; trifluoromethyl; halogen, most preferably fluorine, chlorine or bromine; amino; lower alkylamino, most preferably $CH_3$—NH— or $C_2H_5$—NH—; di-lower alkylamino, most preferably $(CH_3)_2$N— or $(C_2H_5)_2$N—; formylamino; acetylamino; $CH_3$—O—CO—NH— or $C_2H_5$O—CO—NH—; $CH_3$—$SO_2$—NH—; hydroxyl; methoxy or ethoxy; methylthio or ethylthio; $CH_3$—$SO_2$—; $CH_3$—SO—; HOOC—; $HO_3S$—; HCO—; lower alkyl—CO—, most preferably $CH_3$—CO—; lower alkyl—O—CO—, most preferably $CH_3$—O—CO— or $C_2H_5O$—CO—; or —CN.

When $R^1$ and $R^2$ together represent a nitrogen-containing heterocyclyl $R^4$ is a substituent on one or more nitrogen atoms of said heterocyclyl and preferably is lower alkyl, most preferably methyl, ethyl, propyl or isopropyl, especially methyl or ethyl; —C≡N; —CHO; —COO—lower alkyl, most preferably —COO—$CH_3$, —$COOC_2H_5$, —$COOCH(CH_3)_2$ or —COO—$C(CH_3)_3$; —CO—$NH_2$; —CO—NH—lower alkyl, most preferably —CO—NH—$CH_3$, —CO—NH—$C_2H_5$ or —CO—NH—$CH(CH_3)_2$; or —CO—lower alkyl, most preferably —CO—$CH_3$, —CO—$C_2H_5$ or —CO—$CH(CH_3)_2$.

When $R^1$ and $R^2$, together with the carbon atom to which they are bonded, represent an unsaturated ring, said unsaturated ring preferably contains 1 or 2 double bonds. The ring can also cotain 1 or more, preferably 1 or 2, in particular 1, hetero-atom or hetero-group. Hetero-atoms which may be mentioned are oxygen, sulphur and/or nitrogen. Examples of hetero-groups which may be mentioned are the $SO_2$ group and the lower alkyl-N-group, one hetero-atom or one hetero-group preferably being in the 4-position (relative to the carbon atom to which $R^1$ and $R^2$ are bonded) in the case of 6-membered rings. Particularly preferred rings which may be mentioned are:

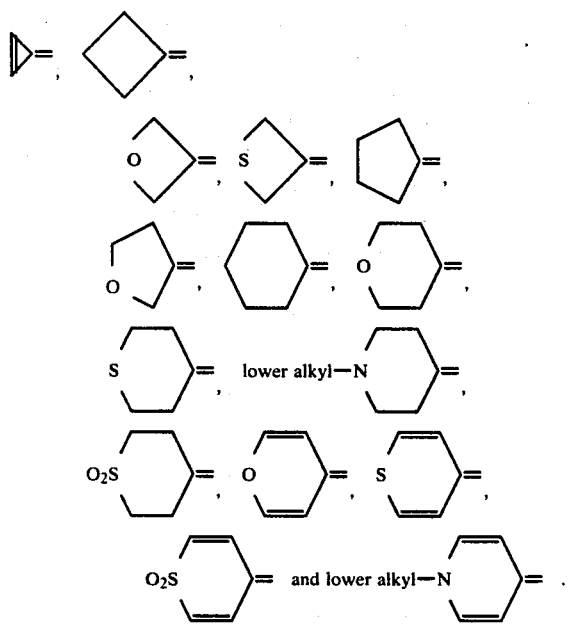

When $R^1$ and $R^2$, together with the carbon atom to which they are bonded, represent a substituted ring, said ring can contain one or more, preferably 1 to 3, in particular 1 or 2, identical or different substituents $R^5$. $R^5$ preferably denotes halogen, most preferably fluorine, chlorine or bromine; hydroxyl; lower alkoxy, most preferably methoxy or ethoxy; lower alkylthio, most preferably methylthio or ethylthio; amino; lower alkylamino, most preferably $CH_3—NH—$ or $C_2H_5—NH—$; di-lower alkylamino, most preferably dimethylamino or diethylamino; —CN; —COOH; —COOCH$_3$ or —COOC$_2$H$_5$; or straight-chain or branched lower alkyl, most preferably methyl or ethyl.

At least one of the radicals $R^1$ and $R^2$, most preferably is hydrogen.

Z most preferably represents the group

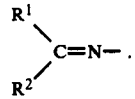

Compounds which contain the radical

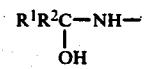

are formed when this radical is already present in the compounds of the formula III, or can be formed when the reaction is carried out in water-containing solvents.

When B is phenyl it can carry one or more, preferably 1 to 3, in particular 1 or 2, identical or different substituents. The substituents can be in the o-position, m-position and/or p-position. Preferably, one substituent is in the p-position or m-position. Examples of substituents which may be mentioned are halogen, for example fluorine, chlorine, bromine or iodine, preferably fluorine, chlorine or bromine; alkyl having 1 to 6, preferably 1 to 4, most preferably 1 or 2, carbon atoms; cyano and methylsulphonyl. Substituted phenyl radicals B which may be mentioned are, in particular, the hydroxphenyl radical (preferably p-hydroxyphenyl), the methylphenyl radical (preferably p-methylphenyl), the cyanophenyl radical (preferably m- and p-cyanophenyl), the methylsulphonyl radical (preferably p-methylsulphonylphenyl) and the fluorophenyl radical (preferably o-fluorophenyl and m-fluorophenyl).

In the definition of T, alkyl in alkyl—CO—O— preferably is alkyl having 1 to 4, most preferably 1 or 2, carbon atoms. Examples which may be mentioned are methyl and ethyl, methyl being particularly preferred.

The heterocyclic ring Het in —S—Het (in the definition of T) consists of 5 or 6 ring members and contains 1 to 4 preferably 1 to 3, identical or different heteroatoms, hetero-atoms being oxygen, sulphur and nitrogen. The heterocyclic ring is preferably unsaturated and particularly preferably contains 2 double bonds. The heterocyclic ring can contain one or more, preferably 1 or 2, in particular one, substituent. Examples of substituents which may be mentioned are: halogen, for example fluorine, chlorine, bromine or iodine, preferably chlorine or bromine, amino, lower alkylamino, di-lower alkylamino, lower alkyl, cycloalkyl(having 3 to 7, preferably 5 or 6, carbon atoms in the cycloalkyl moiety), lower alkyloxy (wherein the alkyl moiety has the same meaning as that given for "lower alkyl" hereinbefore), trifluoromethyl, phenyl and benzyl, and acylamino with preferably 2 to 5, most preferably 2 or 3, carbon atoms. Particularly preferred examples of —S—Het which may be mentioned are:

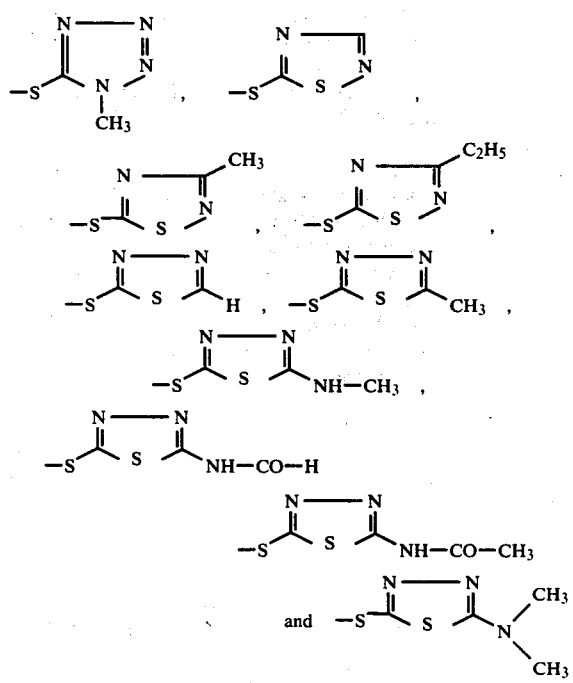

The —S— phenyl radical in the definition of T may be substituted by one or more, preferably 1 to 3, most preferably 1 or 2, identical or different substituents, substituents which are preferred being those which are listed hereinbefore as examples of substituents of the radical —S—Het.

Compounds according to the invention in which C* is present in the D-configuration are very particularly preferred.

All the crystal forms and hydrate forms of the compounds according to the invention, of the general formula I, and their salts are believed to be antibacterially active in the same way.

When the leaving group W is halogen it usually is fluorine, chlorine or bromine, preferably bromine or chlorine, most preferably chlorine.

Nucleofugic leaving groups in the definition of W are to be understood as all the nucleofugic groups customarily used in organicchemistry, and above all those which are described in Angewandte Chemie, 81 (1969), page 543.

Non-toxic, pharmaceutically acceptable salts of formula I are salts of the corresponding acid compounds with inorganic and organic bases, in particular at the acid carboxyl group or the acid carboxyl and sulphonic acid groups of said acid compounds. All the bases customarily used in pharmaceutical chemistry, in particular in the chemistry of antibiotics, may be employed as bases here. Examples of inorganic bases which may be mentioned are: alkali metal hydroxides and alkaline earth metal hydroxides, alkali metal carbonates and alkaline earth metal carbonates and alkali metal bicarbonates, such as sodium hydroxide and potassium hydroxide, calcium hydroxide and magnesium hydroxide, sodium carbonate and potassium carbonate, calcium carbonate and sodium bicarbonate and potassium bicarbonate; aluminium hydroxide and ammonium hydroxide. Primary, secondary and tertiary aliphatic amines and heterocyclic amines can be employed as organic amines. Examples which may be mentioned are: di-lower alkylamines and tri-lower alkylamines, for example diethylamine and triethylamine, tri-β-hydroxyethylamine, procaine, dibenzylamine, N,N'-dibenzylethylenediamine, N-benzyl-β-phenylethylamine, N-methyl- and N-ethyl-morpholine, 1-ephenamine, dehydroabietylamine, N,N'-bis-dehydroabietylethylene-diamine and N-lower alkylpiperidine. So-called basic amino-acids, such as lysine or arginine, can also be advantageously used as bases. Particularly preferred salts are the sodium salts. Preferred esters of formula I include those wherein E is pivaloyl.

Very particularly preferred compounds of the formula I are those in which:

R is hydrogen, alkoxy having 1 to 4 C atoms, preferably methoxy, or the radical —OCH$_2$CH$_2$N(CH$_3$)$_2$, Z is a group of formula

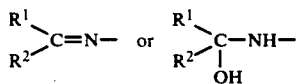

wherein

R$^1$ is hydrogen; and

R$^2$ is phenyl optionally substituted by halogen (preferably fluorine, chlorine and bromine), alkyl having 1 to 4 carbon atoms (preferably methyl), alkoxy having 1 to 4 carbon atoms (preferably methoxy), nitro, cyano, alkylsulphonyl having 1 to 4 carbon atoms (preferably methylsulphonyl) or CH$_3$OOC—, or furyl or thienyl, optionally substituted, preferably in the 4-position or 5-position, by halogen (preferably chlorine or bromine), NO$_2$, alkyl or alkoxycarbonyl having 1 to 4 carbon atoms or CH$_3$COOCH$_2$—, the furyl and thienyl rings preferably being bonded in the 2-position or 3-position; or is pyridyl (preferably pyridyl-3); or is optionally substituted cyclic, alkyl or alkenyl having up to 7 carbon atoms, in particular cyclohexenyl, or alkyl or alkenyl having up to 4 carbon atoms, the said alkyl and alkenyl groups being optionally substituted, preferably by halogen and/or alkoxy having 1 to 4 carbon atoms, preferably methoxy; and A is —CH$_2$—CH$_2$—; and B is phenyl, hydroxyphenyl (preferably p-hydroxyphenyl) or cyclohexadienyl (preferably cyclohexa-1,4-dien-1-yl); and Y is a group of the formula

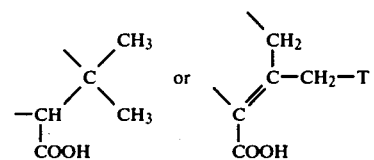

wherein

T is hydrogen, —O—CO—CH$_3$, hydroxyl or thiadiazolylthio or tetrazolylthio optionally substituted by alkyl having 1 to 4 carbon atoms or CF$_3$; and C* is in the D- configuration as well as the sodium salts of these compounds.

The compounds of the general formula II used as starting materials are already known, or can be obtained by known methods (compare DOS (German Published Specification) No. 2,555,159).

All the crystal forms, hydrate forms and salts of the compounds of the general formula II are suitable starting materials for the process according to the invention.

Examples which may be mentioned are: α-aminobenzylpenicillin, α-amino-p-hydroxybenzylpenicillin, α-amino-p-methylbenzylpenicillin, α-amino-p-chlorobenzylpenicillin, 6-[2-amino-2-(1,4-cyclohexadien-1-yl)-acetamido]-penicillanic acid, 7-(α-aminophenylacetamido)-3-methyl-ceph-3-em-4-carboxylic acid 7-(α-amino-phenylacetamido)-3-acetoxymethyl-ceph-3-em-4-carboxylic acid, 7-(2-aminophenylacetamido)-7-methoxy-3-methyl-ceph-3-em-4-carboxylic acid and 7-(2-aminophenylacetamido)-7-methoxy-3-acetoxymethyl-ceph-3-em-4-carboxylic acid or the corresponding trifluoroacetate.

Salts of the compounds of the formula II which can be employed are preferably salts with bases which are listed as being suitable for salt-formation with compounds of the formula I. The sodium salts are particularly preferred.

The compounds of the general formula III used as starting materials can be obtained by known methods. For example, they can be obtained by a reaction route shown in the following reaction diagram (compare, also J.A.C.S. 78 (1956) 5349):

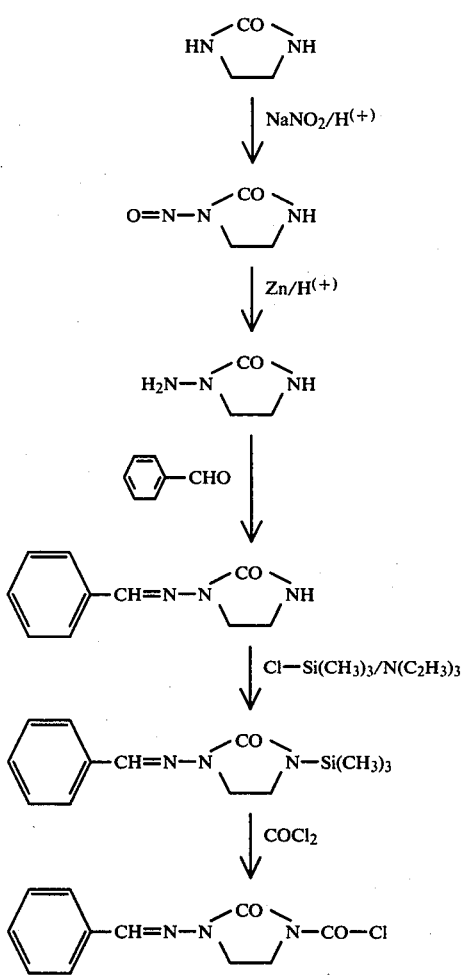

It is also possible to carry out the phosgenation directly, without prior silylation, in an inert organic solvent in the presence of a base.

Examples which may be mentioned of starting compounds, according to the invention, of the general formula III, are: 1-chlorocarbonyl-2-oxo-3-benzalimino-imidazolidine, 1-azido-carbonyl-2-oxo-3-benzalimino-imidazolidine, 1-chlorocarbonyl-2-oxo-3-(4-chloro)-benzalimino-imidazolidine, 1-chlorocarbonyl-2-oxo-3-(4-methoxy)-benzalmino-imidazolidine, 1-chlorocarbonyl-2-oxo-3-(4-nitro)-benzalimino-imidazolidine, 1-chlorocarbonyl-2-oxo-3-(4-cyano)-benzalimino-imidazolidine, 1-chlorocarbonyl-2-oxo-3-(4-methylsulphonyl)-benzalimino-imidazolidine, 1-chlorocarbonyl-2-oxo-3-(thiophene-2-aldimino)-imidazolidine, 1-azidocarbonyl-2-oxo-3-(thiophene-2-aldimino)-imidazolidine, 1-chlorocarbonyl-2-oxo-3-(furane-2-aldimino)-imidazolidine, 1-azidocarbonyl-2-oxo-3-(furane-2-aldimino)-imidazolidine and 1-chlorocarbonyl-2-oxo-3-(but-2-enylideneamino)-imidazolidine.

Those compounds of the general formula III in which W is azide are obtained by known methods, for example from the corresponding compounds of formula III, in which W is halogen, by reaction thereof, for example, with alkali metal azides.

Diluents which can be used in the process (A) according to the invention are water and any inert organic solvent, preferably one which is water-miscible. Examples include, most preferably, lower dialkyl ketones, for example acetone and methyl ethyl ketone, and cyclic ethers, for example tetrahydrofurane and dioxane; nitriles, for example acetonitrile; lower dialkylformamides, for example dimethylformamide; lower alkyl alcohols, for example ethanol and isopropanol, and dimethylsulphoxide. These solvents can also be used in mixtures with one another as well as in any desired mixture of one or more of these solvents with water. The process according to the invention can thus be carried out in solvents consisting of: (a) exclusively water, (b) exclusively one or more organic solvents or (c) water and one or more organic solvents. If, by virtue of the presence of water, it is possible to measure the pH of the reaction medium during the course of the reaction according to the invention, the pH of the reaction mixture is preferably kept at a pH of from 6.5 to 7.5 by adding base or by using a buffer. However, the process according to the invention can also be satisfactorily carried out at other pH values, for example at a pH from 4.5 to 9.0, or at pH from 2.0 to 4.5. Furthermore, it is possible to carry out said reaction in solvents which are not water-miscible, for example halogenated hydrocarbons, such as chloroform or methylene chloride, with the addition of organic bases, preferably lower alkylamines, for example triethylamine and diethylamine, or cyclic bases, for example N-ethylpiperidine. Moreover, the reaction can be carried out in a mixture of water and a solvent which is not water-miscible, such as, for example, a lower alkyl ether, such as diethyl ether, a halogenated hydrocarbon, such as chloroform or methylene chloride; carbon disulphide; isobutyl methyl ketone; an ester, such as ethyl acetate; or an aromatic hydrocarbon, such as benzene, it being appropriate to stir the mixture vigorously and to keep the pH value at from 4.5 to 9.0, or, from 2.0 to 4.5, by adding base or using a conventional buffer solution, for example, a phosphate buffer, acetate buffer or citrate buffer. However, the reaction can also be carried out in water alone in the absence of an organic solvent in the presence of an organic or inorganic base or with the addition of conventional buffer constituents.

Acid-binding agents which can be employed include any acid-binding agent customarily used in the chemistry of antibiotics. These include inorganic bases and organic bases which, for example because of steric hinderance, are difficult to acylate. Examples of inorganic bases which may be mentioned are sodium hydroxide and potassium hydroxide. Virtually all the open-chain or cyclic amines which cannot be acylated or are difficult to acylate, and also heteroaromatic bases, can be used as organic bases. Examples of bases which may be mentioned are tertiary amines, preferably lower alkylamines, for example triethylamine, and/or cyclic bases, for example pyridine, and a secondary amine which may be mentioned which is difficult to acylate is dicyclohexylamine.

The addition of a base is only necessary in the process according to the invention when acid compounds are formed during the reaction, for example in the case where W is halogen or azide.

The reaction temperature can be varied within a relatively wide range. In general, the reaction is carried out at from −20° C. to +50° C., preferably from 0 and +20° C. However, as in most chemical reactions, in principle, higher or lower temperatures can also be used.

The reaction can be carried out under normal pressure, but also under reduced pressure or elevated pressure. In general, the reaction is carried out under normal pressure.

In carrying out the process according to the invention, the proportions of the reactants of the formulae II and III can be varied within wide limits without adversely influencing the result. For example, the starting materials can be reacted with one another in equimolar amounts. However, it can be appropriate to use one of the two reactants in excess, in order to make it easier to purify the desired penicillin or to prepare it in a pure state, and to increase the yield.

For the second process of the invention (process B) comprising direct introduction of a substituent —UR' into a compound of the general formula I in which R is H and E is H or a cation, chemically inert compounds, such as ether, hydrocarbons or halogenohydrocarbon, preferably tetrahydrofurane, are used as solvent.

As for as possible, the temperatures are to be kept below −10° C., but preferably between −40 and −90° C.

t-Butyl hypochlorite is preferably uses as the N-chlorinating agent, but other compounds which contain positively charged chlorine, such as N-chloroacetamide, are also suitable.

The base can be, for example: LiH, NaH, BuLi, PhLi, PhMgBr, or alkyl MgBr, or borax or sodium carbonate. LiH or BuLi is preferably used. In carrying out the process, 1 molar equivalent of a starting compound of the formula I (wherein R is H, E is H or a cation) is reacted with a 3-fold to 6-fold excess of the base, and usually an equimolar amount of t-butyl hypochlorite at a low temperature, an excess (2–100 molar) of a compound RH (wherein R is —UR' as defined hereinbefore) being initially introduced together with the solvent at the same time. It is also possible to initially introduce the base, the solvent and said compound RH, which is preferably an alcohol, such as methanol or ethanol, at a low temperature and then to add the compound of the formula I (wherein R is H) and t-butyl hypochlorite in rapid succession.

The reaction time depends on the size of the group to be introduced. If a methoxy group is introduced, in the case of cephalosporin compounds of formula I 60 minutes are usually sufficient for the reaction to go to completion, and in the case of penicillin compounds of formula I 2 hours are usually sufficient.

However, the rate of reaction can be beneficially shortened by using an excess of t-butyl hypochlorite, but in this case side reactants can occur to an increasing extent. If further functional groups such as OH, NH or COOH, are present in the starting compound an extra equivalent of t-butyl hypochlorite can be used for each further group present in the molecule. The addition of base can also be increased accordingly.

For example, it is possible to employ the reactants of the general formula II in an excess of 0.1 to 0.3 molar equivalents and thereby to achieve a lower decomposition of the reactants of the general formula III in a water-containing solvent mixture. Because of their good solubility in aqueous mineral acids, the excess of the reactants of the general formula II can be easily removed during working up of the reaction mixture.

On the other hand, however, the reactants of the general formula III can also be advantageously employed in an excess of, for example, 0.1 to 1.0 molar equivalents. The reactants of the general formula II are thereby better utilised and the decomposition of the reactants of the general formula III, which proceeds as a side reaction in water-containing solvents, is compensated. Since the compounds of the general formula III, added in excess, are rapidly converted in water into neutral nitrogen-containing heterocyclic compounds, which can be easily removed, the purity of the antibiotics is scarcely impaired here.

The amount of the bases optionally used is determined, for example, by the desire to maintain a particular pH value where a pH measurement and adjustment does not take place or, because of the lack of sufficient amounts of water in the diluent, is not possible or is not appropriate, 2 molar equivalents of base are preferably added.

The working up of the reaction batches for the preparation of the compounds according to the invention and their salts is without exception carried out in the manner known generally for these materials. The isolation and purification of the compounds according to the invention and the liberation of the free acids from salts or the conversion of the free acids into salts are also carried out by methods of organic chemistry which are generally customary and which are familiar to anyone skilled in the art.

The compounds of the general formula I in the form of the free acid are antibacterially active in the same way both in the crystalline form and the amorphous form and both in the anhydrous form and in the various hydrate forms. Likewise, the compounds of the general formula I in the form of their salts, for example the sodium salts, are antibacterially active in the same way both in the crystalline form and in the amorphous form and both in the anhydrous form and in the water-containing form, for example in the hydrate form.

New active compounds which may be mentioned (formulae IV and V) are:

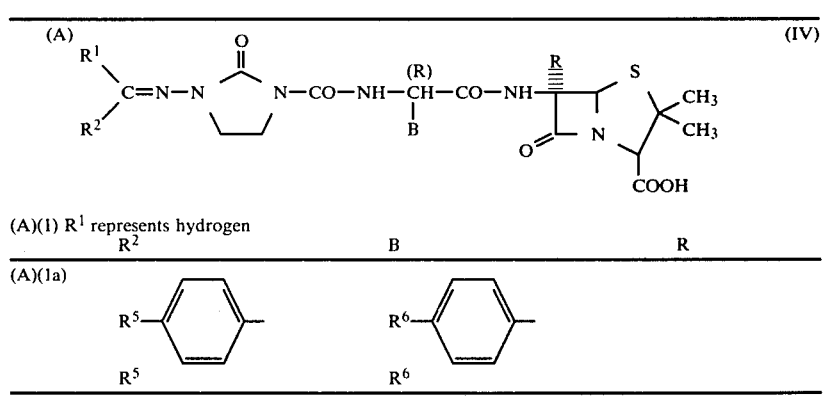

-continued

| | | |
|---|---|---|
| H | H | H |
| 4-Cl | 4-HO— | H |
| 4-CH₃O | H | H |
| 4-NO₂ | H | H |
| 4-CN | H | H |
| 4-CH₃SO₂ | H | H |
| 4-CH₃SO₂ | 4-HO— | H |

| | R² | B | R | |
|---|---|---|---|---|
| (A)(1b) | R⁷ (furan ring with R⁷, R⁸, O) | R⁶-phenyl- | | |
| | R⁷ | R⁸ | R⁶ | |
| | H | H | H | H |
| | H | H | 4-OH | OCH₃ |
| | H | CH₃ | H | H |
| | H | C₂H₅ | H | H |
| | H | i-C₃H₇ | H | H |
| | H | cyclopropyl | H | H |
| | H | CH₃OCH₂ | H | H |
| | H | C₂H₅OCH₂ | H | H |
| | H | (C₂H₅O)₂CH | H | H |
| | H | CH₃S | H | H |
| | H | CH₃O | H | H |
| | H | C₂H₅O | H | H |
| | H | OHC— | H | H |
| | H | O₂N | H | H |
| | H | CH₃SO₂ | H | H |
| | H | CH₃CO | H | H |
| | H | CH₃OCOCH₂ | H | H |
| | H | CH₃OCO | H | H |
| | H | C₂H₅OCO | H | H |
| | H | F | H | H |
| | H | Cl | H | H |
| | H | Br | H | H |
| | H | CH₃SO₂NH | H | H |
| | i-C₃H₇ | H | H | H |
| | H | HOCH₂ | H | H |
| | H | CH₃NHSO₂ | H | H |
| | H | furyl-CH=N— | H | H |
| | H | (furyl-methyl) | | |
| | H | H | H | OCH₃ |
| | H | Cl | 4-OH | OCH₃ |
| | H | H | H | OC₂H₅ |
| | H | H | H | OCH₂CH₂CH₃ |
| | H | H | H | OCH(CH₃)₂ |
| | H | H | H | O—CH₂—CH(CH₃)₂ |
| | H | H | H | O—CH₂—CH₂—N(CH₃)₂ |
| | H | H | 4-OH | OC₂H₅ |
| | H | H | 4-OH | OCH₂CH₂N(CH₃)₂ |
| | H | H | 4-OH | OCH₂CH₂CH₃ |

(A)(2) R and R¹ represent hydrogen; B represents phenyl;
R² represents:

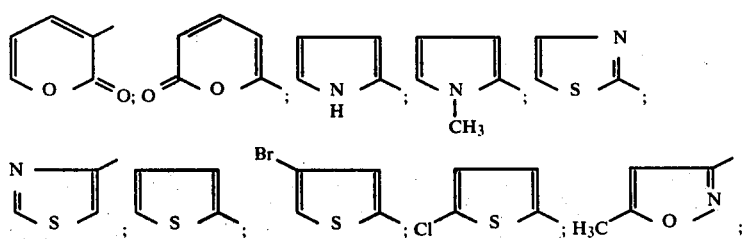

-continued
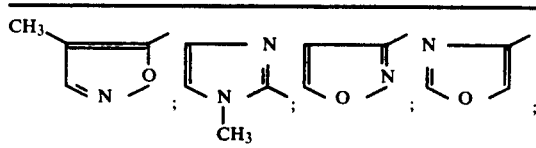
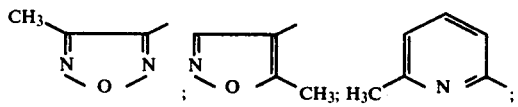
CH₃; C₂H₅; i-C₃H₇;  ; CH₃—CH=CH—;
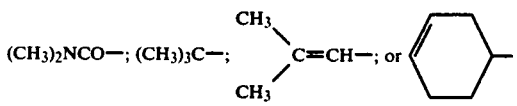
(A)(3) B represents phenyl;
| R¹ | R² |
|---|---|
| CH₃ | CH₃ |
| CH₃ | |
| | 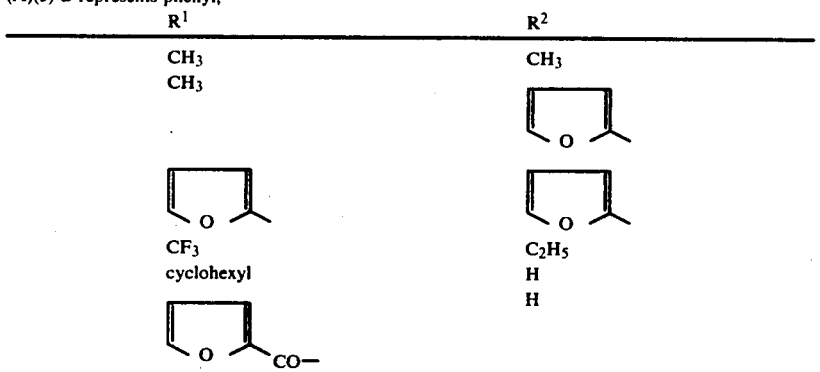 |
| CF₃ | C₂H₅ |
| cyclohexyl | H |
| | H |
(A)(4) B represents 2-furyl, R represents H
| R¹ | R² |
|---|---|
| H | 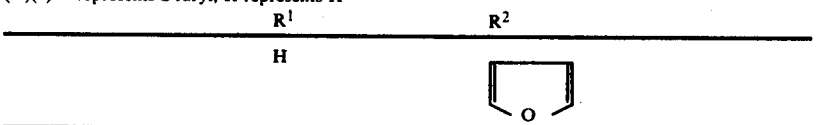 |
(A)(5) B represents p-hydroxyphenyl, R represents H
| R' | R² |
|---|---|
| H | (CH₃)₃C— |
| H | CH₃— |
| H | CH₃—CH=CH— |
(A)(6) B represents cyclohexa-1,4-dien-1-yl; R represents H
| R¹ | R² |
|---|---|
| H | C₆H₅ |
| H | 4-CH₃OC₆H₄ |
| H | 4-CH₃SO₂C₆H₄ |
(A)(7) B represents phenyl; R represents H and
 represents:
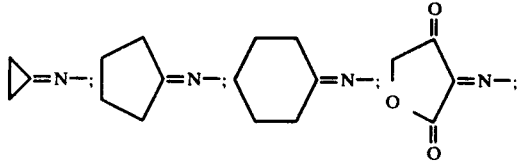

-continued

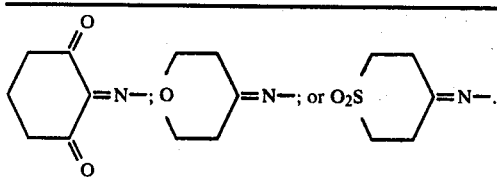

(B) 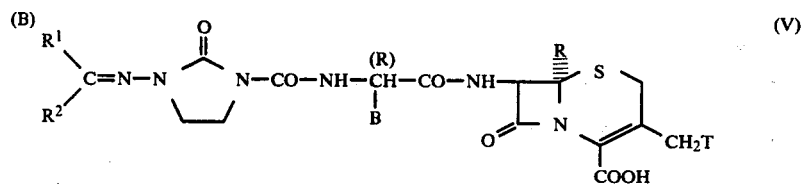 (V)

(B)(1) R¹ represents hydrogen; T represents —O—COCH₃;

| R² | B | R |
|---|---|---|
| (B)(1a)  | | H |

| R⁵ | R⁶ |
|---|---|
| H | H |
| 4-Cl | 4-HO— |
| 4-CH₃O | H |
| 4-NO₂ | H |
| 4-CN | H |
| 4-CH₃SO₂ | H |
| 4-CH₃SO₂ | 4-HO— |

(B)(1b) 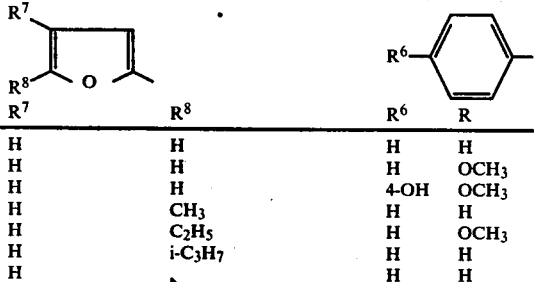

| R⁷ | R⁸ | R⁶ | R |
|---|---|---|---|
| H | H | H | H |
| H | H | H | OCH₃ |
| H | H | 4-OH | OCH₃ |
| H | CH₃ | H | H |
| H | C₂H₅ | H | OCH₃ |
| H | i-C₃H₇ | H | H |
| H | ▷— | H | H |
| H | CH₃OCH₂ | H | H |
| H | C₂H₅OCH₂ | H | H |
| H | (C₂H₅O)₂CH | H | H |
| H | CH₃S | H | H |
| H | CH₃O | H | H |
| H | C₂H₅O | H | H |
| H | OHC— | H | H |
| H | O₂N | H | H |
| H | CH₃SO₂ | H | H |
| H | CH₃SO₂ | H | OCH₃ |
| H | CH₃CO | H | H |
| H | CH₃OCOCH₂ | H | H |
| H | CH₃OCO | H | H |
| H | C₂H₅OCO | H | H |
| H | F | H | OCH₃ |
| H | H | 4-OH | O—C₂H₅ |
| H | H | 4-OH | OCH₂CH₂CH₃ |
| H | H | 4-OH | OCH₂CH₂N(CH₃)₂ |
| H | H | 4-OH | OCH₂CH(CH₃)₂ |
| H | H | H | OC₂H₅ |
| H | H | H | OCH₂CH₂CH₃ |
| H | H | H | OCH(CH₃)₂ |
| H | H | H | OCH₂CH₂CH₂CH₃ |
| H | H | H | OCH₂CH(CH₃)₂ |
| H | H | H | OCH₂CH₂N(CH₃)₂ |
| H | Cl | H | H |
| H | Br | H | H |
| H | CH₃SO₂NH | H | H |
| i-C₃H₇ | H | H | H |
| H | HOCH₂ | H | H |
| H | CH₃NHSO₂ | H | H |

-continued
| H | 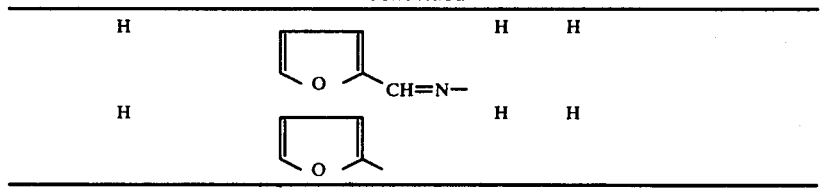 | H | H |
| H | | H | H |
(B)(2) $R^1$ represents hydrogen; B represents phenyl;
T represents —O—CO—$CH_3$; $R^2$ represents (the meaning of R in brackets)
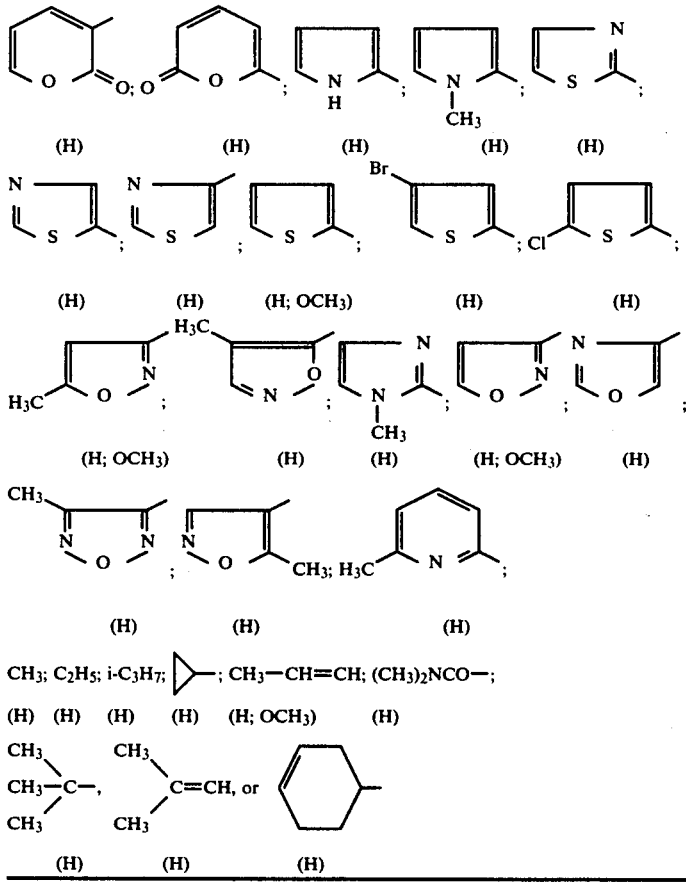
$CH_3$; $C_2H_5$; i-$C_3H_7$; ▷—; $CH_3$—CH=CH; $(CH_3)_2$NCO—;
(H)  (H)  (H)  (H)  (H; $OCH_3$)  (H)
$CH_3$\\ $CH_3$\\
$CH_3$—C—, $CH_3$/C=CH, or ⌬—
$CH_3$/ $CH_3$/
(H) (H) (H)
(B)(3) B represents phenyl; T represents —O—CO—$CH_3$; R = H
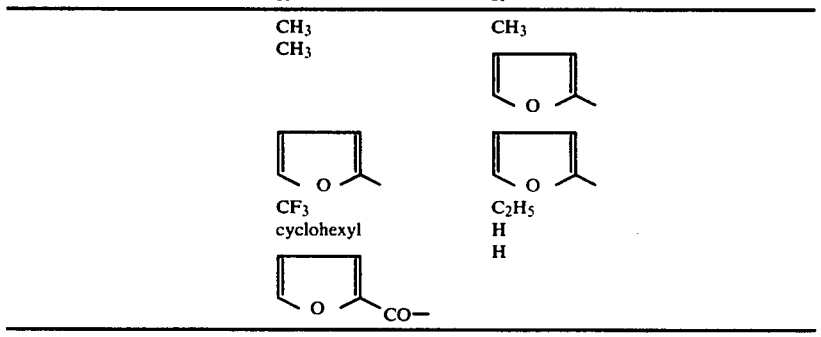
(B)(4) B represents 2-furyl; T represents —O—CO—$CH_3$
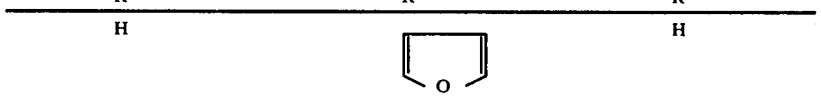

-continued

| | | |
|---|---|---|
| H | [furan-2-yl structure] | OCH$_3$ |

(B)(5) B represents cyclohexa-1,4-dien-1-yl; T represents —O—COCH$_3$, R = H

| R$_1$ | R$_2$ |
|---|---|
| H | C$_6$H$_5$ |
| H | 4-CH$_3$OC$_6$H$_4$ |
| H | 4-CH$_3$SO$_2$C$_6$H$_4$ |

(B)(6) B represents phenyl; T represents —O—COCH$_3$, R represents H, $\overset{R^1}{\underset{R^2}{\diagup}}C=N-$ represents

[structures: cyclopropylidene=N—; cyclopentylidene=N—; cyclohexylidene=N—; 2,4-dioxotetrahydrofuran-3-ylidene=N—; 2,6-dioxocyclohexylidene=N—; tetrahydropyran-4-ylidene=N—; or O$_2$S-containing 6-ring ylidene=N—]

(B)(7)

| R$^1$ | R$^2$ | B | T | R |
|---|---|---|---|---|
| H | [5-methylfuran-2-yl] | C$_6$H$_5$ | OH | H |
| H | [HOCH$_2$-5-methylfuran-2-yl] | C$_6$H$_5$ | OH | H |
| H | [CH$_3$S-5-methylthiophen-2-yl] | C$_6$H$_5$ | OH | H |
| H | [5-methylfuran-2-yl] | cyclohexa-1,4-dien-1-yl | H | OCH$_3$ |
| H | [5-methylfuran-2-yl] | cyclohexa-1,4-dien-1-yl | H | H |

(B)(8) B represents phenyl; R represents H

| $\overset{R^1}{\underset{R^2}{\diagup}}C=N-$ | T |
|---|---|
| [cyclopropylidene]=N— | —OCOCH$_3$ |
| [2,4-dioxotetrahydrofuran-3-ylidene]=N— | —OCOCH$_3$ |

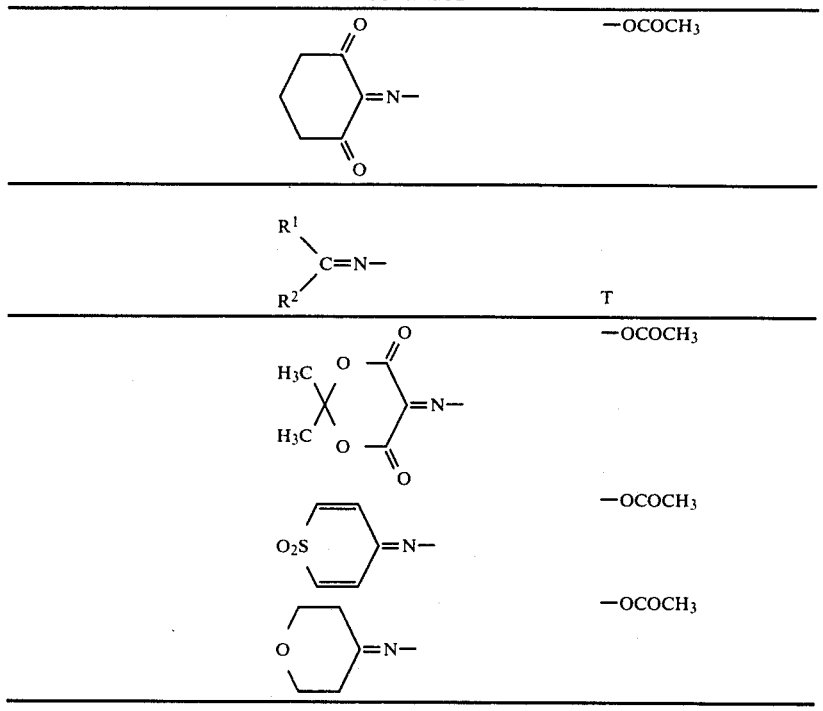

The active compounds according to the invention display a powerful and broad antimicrobial activity, coupled with low toxicity. These properties enable them to be used as chemotherapeutic active compounds in medicine and as substances for preserving inorganic and organic materials, especially organic materials of all kinds, for example polymers, lubricants, paints, fibres, leather, paper and timber, and foodstuffs, and water.

The active compounds according to the invention are active against a very broad spectrum of micro-organisms. With their aid it is possible to combat Gram-negative and Gram-positive bacteria and bacteria-like micro-organisms and to prevent, alleviate and/or cure diseases caused by these pathogens.

The active compounds according to the invention are particularly active against bacteria and bacteria-like micro-organisms. They are, therefore, particularly suitable for the prophylaxis and chemotherapy, in human medicine and verterinary medicine, of local and systemic infections caused by these pathogens.

For example, local and/or systemic diseases which are caused by the following pathogens or by mixtures of the following pathogens can be treated and/or prevented:

Micrococcaceae, such as Staphylococci, for example *Staphylococcus aureus, Staph. epidermidis* and *Staph. aerogenes,* and *Gaffkya tetragena* (Staph. = Staphylococcus);

Lactobacteriaceae, such as Streptococci, for example *Streptococcus pyogenes,* α- and β-haemolysing Streptococci, non-(γ-)-haemolysing Streptococci, *Str. viridans, Str. faecalis* (Enterococci), *Str. agalactiae, Str. lactis, Str. equi* and *Str. anaerobis,* and *Diplococcus pneumoniae* (Pneumococci) (Str.=Streptococcus);

Neisseriaceae, such as Neisseriae, for example *Neisseria gonorrhoeae* (Gonococci), *N. meningitidis* (Meningococci), *N. catarrhalis* and *N. flava* (N.=Neisseria);

Corynebacteriaceae, such as Corynebacteria, for example *Corynebacterium diphtheriae, C. pyogenes, C. diphtheroides, C. acnes, C. parvum, C. bovis, C. renale, C. ovis* and *C. murisepticum.*

Mycobacteriaceae, such as pathogens of mycobacterioses, for example *Mycobacterium tuberculosis, M. bovis, M. avium,* so-called typical mycobacteria of the Runyon groups I, II, III and IV and M. leprae (M.=Mycobacterium);

Enterobacteriaceae, such as Escherichiae bacteria of the Coli group: Escherichia bacteria, for example *Escherichia coli,* Enterobacter bacteria, for example *E. aerogenes* and *E. cloacae,* Klebsiella bacteria, for example *K. pneumoniae, K. pneumoniae* and *K. ozaenae,* Erwiniae, for example Erwinia spec., and Serratia, for example *Serratia marcescens,* (E.=Enterobacter) (K.=Klebsiella), Proteae bacteria of the Proteus group: Proteus, for example *Proteus vulgaris, Pr. morganii, Pr. rettgeri* and *Pr. mirabilis,* and Providencia, for example Providencia sp., (Pr.=Proteus), Salmonelleae: Salmonella bacteria, for example *Salmonella paratyphi* A and B, *S. typhi, S. enteritidis, S. cholerae suis* and *S. typhimurium* (S.=Salmonella, and Shigella bacteria, for example *Shigella dysenteriae, Sh. ambigua, Sh. flexneri, Sh. boydii* and *Sh. sonnei* (Sh.=Shigella);

Pseudomonadaceae, such as Pseudomonas bacteria, for example *Pseudomonas aeruginosa* and *Ps. pseudomallei* (Ps.=Pseudomonas), and Aeromonas bacteria, for example *Aeromonas liquefaciens* and *A. hydrophila* (A.-=Aeromonas);

Parvobacteriaceae, such as Pasteurella bacteria, for example *Pasteurella multocida, Past. pestis* (Yersinia) and *Past. pseudotuberculosis,* Haemophilus bacteria, for example *Haemophilus influenza, H. ducreyi, H. suis, H. canis* and *H. aegypitcus* (H.=Haemophilus) and Bordetella bacteria, for example *B. bronchiseptica* (B.=Bordetella);

Bacteroidaceae, such as Bacteroides bacteria, for example *Bacteroides fragilis* and *B. serpens* (B.=Bacteroides), Fusiforme bacteria, for example *Fusobacterium*

*fusiforme,* and *Sphaerophorus bacteria,* for example *Sphaerophorus necrophorus, Sph. necroticus* and *Sph. pyrogenes* (Sph.=Sphaerophorus);

Bacillaceae, such as aerobic spore-forming Bacillaceae, for example *Bacillus anthracis* (*B. subtilis* and *B. cereus* ) (B.=Bacillus) and anaerobic spore-forming Chlostridia, for example *Clostridium perfringens, Cl. septicium, Cl. oedematien, Cl. histolyticum, Cl. tetani* and *Cl. botulinum* (Cl.=Clostridium).

The above list of pathogens is purely illustrative and is in no way to be interpreted as restrictive.

Examples which may be mentioned of diseases which can be prevented, alleviated and/or cured by the active compounds according to the invention are: diseases of the respiratory passages and of the pharyngeal cavity; otitis; pharyngitis; pneumonia; peritonitis; pyelonephritis; cystitis; endocarditis; systemic infections; bronchitis; arthritis and local infections.

As stated above, the invention also relates to the use in human and veterinary medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administeration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 0.25 to 50 g preferably 1 to 10 g of active ingredient.

The production of the above mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally or intravenously), rectally or locally, preferably orally or parenterally, most preferably intravenously or intramuscularly. Preferred pharmaceutical compositions and medicaments are therefore those adapted for oral or parenteral, especially intravenous or intramuscular administration. Administration in the method of the invention is preferably oral or parenteral; especially intravenous or intramuscular.

In general it has proved advantageous to administer amounts of from 5 to 1000, preferably 20 to 200, mg/kg of body weight per day to achieve effective results. Individual doses preferably contain from 1 to 250, most preferably 10 to 100, mg/kg of body weight. Nevertheless, it can at times be necessary to deviate from those dosage rates, and in particular to do so as a function of the nature and body weight of the human or animal subject to be treated, the individual reaction of this subject of the treatment, the type of formulation in which the active ingredient is administered and the mode in which the administration is carried out, and the point in the progress of the disease or interval at which it is to be administered. Thus it may in some case suffice to use less than the above mentioned minimum dosage rate, whilst other cases the upper limit mentioned must be exceeded to achieve the desired results. Where larger amounts are administered it can be advisable to divide these into several individual administrations over the course of the day.

In further respects the invention provides a preservative comprising a compound of the invention, and a method of preserving organic and inorganic materials which comprises administering to them a compound of the invention either alone or in admixture with a diluent or in the form of a said preservative.

When used as feedstuff additives, the new compounds can be administered in the customary concentrations and formulations, together with the feedstuff or with feedstuff formulations or with the drinking water provided. By this means it is possible to prevent, alleviate and/or cure infections by Gram-negative or Gram-positive bacteria and also to achieve promotion of growth and better utilisation of the feedstuff.

The new penicillins and cephalosporins are distinguished by powerful antibacterial actions, which have been tested in vivo and in vitro.

The penicillins and cephalosporins according to the invention can, in order to broaden the spectrum of activity and to achieve a more powerful action, especially in the case of bacteria which form $\beta$-lactamase, be combined with other antimicrobial active compounds, for example with penicillins which, in particular, are resistant to penicillinase. Such a combination would be, for example, that with oxacillin or dicloxacillin.

The penicillins and cephalosporins according to the invention can, in order to broaden the spectrum of activity or to achieve a more powerful action, also be combined with aminoglycoside antibiotics, such as, for example, gentamycin, kanamycin, sisomycin, amicacin or tobramycin.

The activity of the $\beta$-lactam antibiotics according to the invention can be demonstrated, by way of example, by the following in vitro and in vivo experiments:

1. In vitro experiments

Examples 1.3., 2.3. and 2.4., which can be regarded as typical representatives of the compounds according to the invention, were diluted to a content of 100 $\mu$g/ml with Muller-Hinton nutrient broth, with the addition of 0.1% of glucose. In each case, the nutrient solution contained $1 \times 10^5$ to $2 \times 10^5$ bacteria per milliliter. The small tubes containing this batch were in each case incubated for 24 hours and the degree of turbidity was then determined. Freedom from turbidity indicates action. At a dosage of 100 $\mu$g/ml, the following bacterial cultures were free from turbidity (sp. = species): *Klebsiella pneumoniae; Enterobacter aerogenes* sp.; Providencia; *Serratia marcescens; E. coli* BE; Salmonella sp.; Shigella sp.; Proteus, indole-negative and indole-positive; *Pasteurella pseudotuberculosis;* Brucella sp.; *Haemophilus influenzae; Bordetella bronchiseptica; Staphylococcus aureus* 133; *Neisseria catarrhalis* sp.; *Diplococcus pneumoniae* sp.; *Streptococcus pyogenes* W.; Enterococcus sp.; Lactobacillus sp.; *Corynebacterium diphteriae gravis; Corynebacterium pyogenes* M; *Clostridium tetani* and *Pseudomonas aeruginosa* sp.

2. In vivo experiments

Table 1 which follows shows the action of one of the compounds according to the invention against several bacteria in an animal experiment using white mice. White mice of the $CF_1$ strain were infected intraperitoneally with the particular strain of bacteria indicated.

Table 1

| | Animal experiments with white mice Determination of the $ED_{100}$ after 24 hours | |
|---|---|---|
| Germ | | Dose in mg of the β-lactam antibiotic of Examples 1.3., 2.3 and 2.4 per kg/body weight (subcutaneously) |
| Escherichia coli C 165 | | 2 × 150 |
| Klebsiella 63 | | 2 × 150 |

Therapy: 2 administrations: 30 minutes and 90 minutes after infection. The $ED_{100}$ is the dose at which 100% of the infected animals still survive after 24 hours.

Examples 36 and 36.5 were also investigated in the in vitro test described above. It is shown that all the abovementioned bacterial cultures also remain free from turbidity in this test.

In addition, the compound 7-methoxy-7-(D-α-[(2-oxo-3-furfurylideneamino-imidazolidin-1-yl)-carbonylamino]-phenylacetamido]-3-acetoxymethyl-ceph-3-em-4-carboxylic acid was compared with the commercial product Cefazolin in the agar dilution test using OXOID DST agar as the growth medium. In this comparison, the substances were diluted in liquid agar in two steps; after the agar had solidified, the bacteria were applied to the agar surface, using a multiple inoculation apparatus and the plates were incubated at 37° C. for 24 hours. After 24 hours, the concentration at which no colony formation took place was read as the minimum inhibitory concentration (MIC).

The table which follows shows the results of this comparison.

| | MIC in mcg/ml | |
|---|---|---|
| Germ | Example No. 36.5 | Cefazolin |
| E. coli T 7 | ≦0.25 | 16.0 |
| E. coli A 261 | ≦0.25 | 4.0 |
| E. coli F 14 | 4.0 | 16.0 |
| Klebsiella pneumoniae | | |
| 57 US | 1.0 | 4.0 |
| 1852 | 1.0 | 16.0 |
| Proteus vulgaris 1017 | 16.0 | >256 |

The process according to the invention is illustrated by the examples which follow:

The α-aminobenzylpenicillin used in the examples which follow contained about 14% of water; however, anhydrous α-aminobenzylpenicillin [compare U.S. Pat. No. 3,144,445] can also be equally well used.

The α-amino-p-hydroxybenzylpenicillin used in the examples contained about 13% of water; however, anhydrous α-amino-p-hydroxybenzylpenicillin can also be equally well used.

The 6-[2-amino-2-(1,4-cyclohexadien-1-yl)-acetamido]-penicillanic acid used in the examples was essentially anhydrous.

The 7-(α-amino-phenylacetamido)-3-methyl-ceph-3-em-4-carboxylic acid used in the examples contained about 5% of water; however, anhydrous 7-(α-amino-phenylacetamido)-3-methyl-ceph-3-em-4-carboxylic acid can also be equally well used.

The 7-(α-amino-phenylacetamido)-3-acetoxymethyl-ceph-3-em-4-carboxylic acid used in the examples contained 8% of water; however, anhydrous 7-(αamino-phenylacetamido)-3-acetoxymethyl-ceph-3-em-4-carboxylic acid can also be equally well used.

The water content of the starting compounds is not important in carrying out the process according to the invention.

By "ampicillin" is meant that α-aminobenzylpenicillin with the D = R-configuration in the side chain, by "amoxicillin" is meant that α-amino-p-hydroxy-benzylpenicillin with the D = R-configuration in the side chain and by "epicillin" is meant that α-amino-α-(1,4-cyclohexadien-1-yl)-methylpenicillin with the D = R-configuration in the side chain.

By "cefalexin" is meant that 7-(α-aminophenylacetamido)-3-methyl-ceph-3-em-4-carboxylic acid with the D = R-configuration in the side chain and by "cephaloglycine" is meant that 7-(α-aminophenylacetamido)-3-acetoxymethyl-ceph-3-em-4-carboxylic acid with the D = R-configuration in the side chain.

Unless otherwise indicated, the NMR spectra of the compounds according to the invention were recorded in $CD_3OD$ solution. The notations in brackets have the following meanings:

s = singlet
d = doublet
m = multiplet
AB = AB system
t = triplet
q = quartet

Unless otherwise indicated, the IR spectra of the compounds according to the invention were recorded in liquid paraffin suspensions.

Explanation of the abbreviations used in the examples:

vol. = volume
pts. by wt. = parts by weight
pts. by vol. = parts by volume
hrs. = hours
hr. = hour
THF = tetrahydrofurane
DMF = dimethylformamide
ether = diethyl ether
ethyl acetate = acetate acid ethyl ester
room temperature = about 20° C.
abs. = absolute
decomp. pt. = decomposition point The % data for the yields denotes yields in % of theory.

EXAMPLE 1

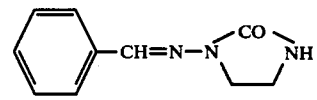

1.1.

2-Oxo-imidazolidine (31.5 pts. by wt.) is dissolved in 2 N sulphuric acid (1,000 pts. by vol.), the solution is cooled to 3-6° C., a solution of sodium nitrite (25.25 pts. by wt.) in water (50 pts. by vol.) is added dropwise in the course of 13 minutes, whilst stirring and cooling further, the mixture is then subsequently stirred for a further 1.5 hrs. in an ice bath and purified zinc dust (55 pts. by wt.) is then introduced in the course of one hour. The mixture is stirred for a further 0.5 hr., whilst cooling with ice, and then subsequently stirred for a further 1 hr. at room temperature. The unreacted zinc is then filtered off and washed with a little water, benzaldehyde (35 pts. by wt.) is added to the combined filtrates and the mixture is stirred vigorously for 0.5 hr. The 1-benzalimino-2-oxo-imidazolidine which has precipitated is then filtered off and, after drying (49.2 pts. by wt.; melting point = 194–200° C.) is recrystallised from ethanol.

Yield 41.4 pts. by wt., melting point = 202° C.
IR spectrum: 1720 cm⁻¹ (C=O).
calculated: C, 63.5; H, 5.9; N, 22.2. found: C, 64.1; H, 5.7; N, 22.7.

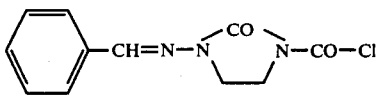

1.2

A mixture of 1-benzalimino-2-oxo-imidazolidine (11.7 pts. by wt.) (see 1.1.), benzene (120 pts. by vol.) and triethylamine (13.8 pts. by vol.) is heated to the boil and a solution of trimethylchlorosilane (10 pts. by wt.) in benzene (50 pts. by vol.) is then added dropwise in the course of 1 hr., whilst stirring. The mixture is then kept at the boil for a further 5.5 hrs. and the triethylammonium hydrochloride which has separated out is filtered off hot and washed with hot benzene. A solution of phosgene (6.2 pts. by wt.) in benzene (30 pts. by vol.) is added to the cooled, combined benzene filtrates. The mixture is allowed to stand overnight well sealed at room temperature. The majority of the excess phosgene present is then removed by means of a dry air stream. The 1-chlorocarbonyl-2-oxo-3-benzalimino-imidazolidine is filtered off and dried.

Yield 8.9 pts. by wt., melting point=250°–252° decomp.
IR spectrum: 1800 cm⁻¹ (—CO—Cl)
calculated: C, 52.5; H, 4.0; Cl, 14.1; N, 16.7. found: C, 51.8; H, 5.6; Cl, 14.6; N, 16.8.

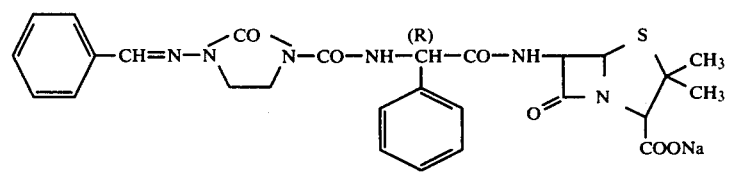

1.3.

Ampicillin (14 pts. by wt.) is suspended in 80% strength aqueous tetrahydrofurane 8140 pts. by vol.) and dissolved by means of the amount of triethylamine which is just necessary (the pH is then 8.0), 1-chlorocarbonyl-2-oxo-3-benzalimino-imidazolidine (7.8 pts. by wt.) (see 1.2.) is introduced slowly, whilst stirring, and the pH is kept at 7.0–7.5 during this procedure by the appropriate addition of triethylamine. The mixture is then further stirred until no further triethylamine must be added in order to maintain the pH range indicated (about 1–2 hrs.). The mixture is diluted with water (200 pts. by vol.), the pH was adjusted to 6.5, the tetrahydrofuran is substantially evaporated off in vacuo and the aqueous solution which remains is washed once with ether in a separating funnel, then covered with a layer of ethyl acetate and acidified down to pH 2 by means of dilute HCl, whilst stirring. The organic phase is then separated off, washed with saturated NaCl solution, dried over MgSO₄ and, after diluting with the same volume of ether, an about 1-molar sodium 2-ethylhexanoate solution in methanol-containing ether is added until precipitation stops. The sodium 6-{D-α-[(2- oxo-3-benzalimino-imidazolidin-1-yl)-carbonylamino]-phenylacetamido}-penicillanate is filtered off, washed with ether and then with a mixture of ether and methanol (5–10%) and isopropanol and dried.

Yield 6.2 pts. by wt., β-lactam content 91%.

According to the NMR spectrum, the substance still contains 2.5 mols of H₂O, 0.1 mol of isopropanol and 0.04 mol of sodium 2-ethyl-hexanoate. This was taken into consideration in the calculated analysis values.

calculated: C, 51.5; H, 5.3; N, 13.0; S, 5.0. found: C, 50.9; H, 5.2; N, 12.9; S, 5.1.

NMR signals at τ=2.1–2.8 (11H); 4.3–4.65 (3H); 5.8 (1H); (in CD₃OD) 6.1–6.35 (4H) and 8.3–8.6 ppm (6H).

IR spectrum (carbonyl range): 1770, 1730, 1665, 1610 and (in liquid paraffin) 1540 cm⁻¹.

1.4

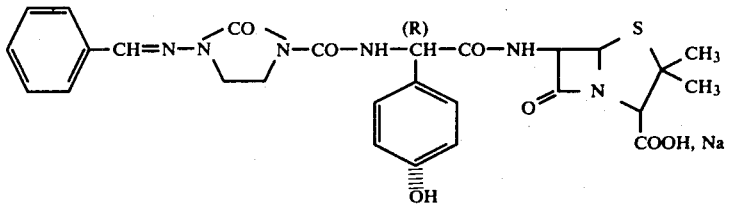

This penicillin is prepared from amoxicillin trihydrate (6.0 pts. by wt.) and 1-chlorocarbonyl-2-oxo-3-benzaliminoimidazolidine (3.6 pts. by wt.) (see 1.2.) in the manner described under 1.3. On acidifying the aqueous reaction solution to pH 1.5 with dilute hydrochloric acid (about 20% strength), some of the penicillic acid liberated is not taken up by the ethyl acetate. This portion is filtered off, washed with water and dried (yield: 5.2 pts. by wt.). Further sodium salt of the penicillin can then be precipitated from the ethyl acetate phase with sodium 2-ethyl-hexanoate (yield: 1.4 pts. by wt.).

6-{D-α-[(2-Oxo-3-benzalimino-imidazolidin-1-yl)-carbonylamino]4-hydroxyphenylacetamino}-penicillanic acid Yield: 5.2 pts. by wt.
β-Lactam content (iodometric): 81%
(from the NMR spectrum): 89%

According to the NMR spectrum, the substance contains 3.4 mols of H₂O and 0.5 mol of ether per mol of substance. If this is taken into consideration in the calculated analysis values, the following are found:

calculated: C, 51.2; H, 5.9; N, 12.4; S, 4.7. found: C, 50.7; H, 5.5; N, 12.8; S, 4.8.

NMR signals at τ=2.2–3.3 (10H); 4.3–4.65 (3H); 5.7 (1H); (in CD₃OD) 6.15–6.4 (4H) and 8.35–8.6 ppm (6H).

IR spectrum (carbonyl range): 1780, 1740 (shoulder), 1725,
(in liquid paraffin) 1645 and 1520 cm⁻¹.

Sodium 6-{D-α-[(2-oxo-3-benzalamino-imidazolidin-1-yl)-carbonylamino]-4-hydroxyphenylacetamido}-penicillanate Yield: 1.4 pts. by wt.

β-Lactam content (iodometric): 96%
(from the NMR spectrum): 87%

According to the NMR spectrum, the substance contains 2.5 mols of H₂O and 0.25 mol of sodium 2-ethyl-hexanoate per mol of substance (and in addition an unknown impurity, in an unknown amount, originating from the amoxil used). If the identified concomitant materials are taken into consideration in the calculated analysis values, there results:

calculated: C, 50.6; H, 5.2; N, 12.2; S, 4.6. found: C, 51.2; H, 6.0; N, 11.7; S, 4.5.

NMR signals at τ=2.1–3.3 (10H); 4.4–4.7 (3H); 5.8 (1H); (in CD₃OD) 6.1–6.4 (4H) and 8.3–8.6 ppm (6H).

IR spectrum (carbonyl range): 1770, 1735, 1670, 1600 and (in liquid paraffin) 1560–1520 cm⁻¹.

and reacted with 12.6 pts. by wt. of 1-chlorocarbonyl-2-oxo-3-benzalimino-imidazolidine as in Example 13 and the mixture is worked up. On acidifying with dilute hydrochloric acid (for example 2 N HCl) 7-{D-α-[(2-oxo-3-benzalimino-imidazolidin-1-yl)-carbonylamino]-phenylacetamido}-3-acetoxymethyl-ceph-3-em-4-carboxylic acid precipitates (1.9 pts. by wt., corresponding to 61.4%). The precipitate is dissolved in 5 pts. by vol. of dimethylacetamide, 3 pts. by vol. of a methanolic 1 M sodium 2-ethyl-hexanoate solution are added and the mixture is added to 30 pts. by vol. of a 10:1 mixture of ether/methanol, whilst stirring, whereupon 1.7 pts. by wt. of sodium 7-{D-α-[(2-oxo-3-benzalimino-imidazolidin-1-yl)-carbonylamino]-phenylacetamido}-3-acetoxymethyl-ceph-3-em-4-carboxylate of decomp. pt. 180°–185° C. precipitate.

The ethyl acetate phase is worked up as in Example 1.3, whereupon a further 0.9 pt. by vol. (corresponding to 28.0%) of the sodium salt is obtained.

$C_{29}H_{27}N_6NaO_8S.H_2O$: calculated: C, 52.72; H, 4.42; N, 12.71; S, 4.85. found: C, 52.5; H, 4.9; N, 12.2; S, 4.6.

IR (KBr): 1760, 1725, 1670, 1605 and 1520 cm⁻¹.

NMR (CD₃OD/D₂O): 7.75 and 7.40 (m, 11H), 5.75 (d, 1H), 5.57 (s, 1H), 5.00 (d, 1H), 4.87 (overlaid by the signal of the replaceable protons), 3.82 (m, 4H) and 2.08 (s, 3 H) δ.

The signals of the C-2 protons are overlaid by the

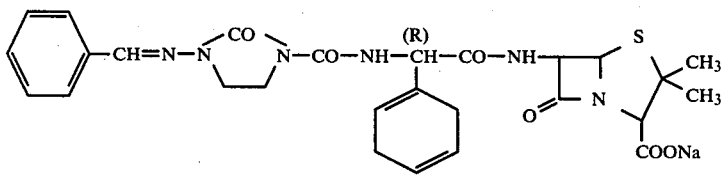

1.5

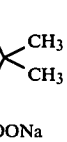

This penicillin is prepared from epicillin (1.5 pts. by wt.) and 1-chlorocarbonyl-2-oxo-3-benzalimino-imidazolidine (1.1 pts. by wt.) in the manner described under 1.3. Yield: 1.7 pts. by wt. of sodium 6-{D-α-[(2-oxo-3-benzalimino-imidazol-1-yl)-carbonylamino]-cyclohex-1,4-dien-1-yl-acetamido}-penicillanate with a β-lactam content (iodometric) of 90%, (derived from the NMR spectrum: 91%).

According to the NMR spectrum, the substance contains 2.5 mols of H₂O and 0.072 mol of sodium 2-ethyl-hexanoate. This was taken into consideration in the following analysis values:

calculated: C, 51.2; H, 5.4; N, 13.0; S, 4.9. found: C, 50.9; H, 5.7; N, 13.6; S, 4.6.

NMR signals at τ=2.0–2.65 (5H); 4.0 (1H); 4.25 (2H); (in CD₃OD) 4.45 (2H); 4.95 (1H); 5.75 (1H); 6.0–6.3 (4H); 7.1–7.4 (4H) and 8.25–8.5 ppm (6H).

IR spectrum (carbonyl range); 1765, 1730, 1660, 1600 and (in liquid paraffin) 1530 cm⁻¹.

CD₃OD solvent peak.

The β-lactam content is between 80 and 85%.

EXAMPLE 2

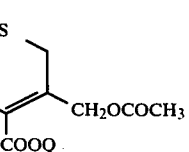

2.1.

15.8 pts. by wt. of 2-oxo-imidazolidine, 12.6 pts. by wt. of sodium nitrite and 27.5 pts. by wt. of zinc dust are processed as in Example 1.1. and the mixture is stirred overnight with 23.2 by wt. of 4-chlorobenzaldehyde.

20.5 pts. by wt. of 1-(4-chloro)-benzalimino-2-oxo-imidazolidine of melting point 223°–235° C.

$C_{10}H_{10}ClN_3O$: calculated: C, 53.70; H, 4.51; N, 18.79; Cl, 15.85. found: C, 53.9; H, 4.5; N, 18.7; Cl, 16.0.

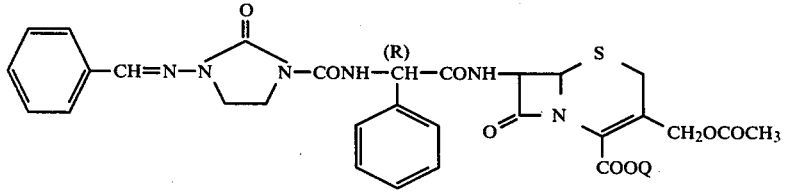

1.6

Q = H, Na 2.25 pts. by wt. of cephaloglycine dihydrate are suspended in 50 ml of 80 percent strength aqueous THF IR (KBr): 3250, 3130, 1735, 1705 and 1595 cm⁻¹.

NMR (d₆-DMSO): 7.66 and 7.45 (AB, 4H), 7.60 (s, 1H), 7.15 (s, broad, 1H), and m, centred at 3.6 (4H) δ.

Ir (KBr): 1760, 1725, 1665 and 1595 cm⁻¹.

NMR (CD₃OD): 7.6–7.2 (m, 10H), 5.60 (s, 1H), 5.45 (q, 2H), 4.15 (s, 1H), 3.80 (broad s, 4H), 1.57 (s, 3H) and 1.48 (s, 3H)δ.

2.2

2.4

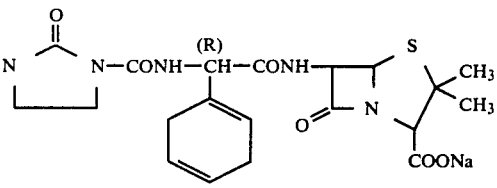

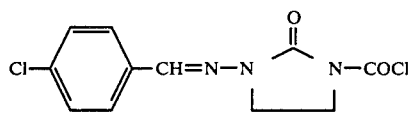

A solution of 31.0 pts. by wt. of trimethylchlorosilane in 100 pts. by vol. of abs. dioxane is added dropwise to a boiling solution of 21.4 pts. by wt. of 1-(4-chloro)-benzalimino-2-oxo-imidazolidine and 31.0 pts. by wt. of triethylamine in 240 pts. by vol. of absolute dioxane in the course of 1 hr., whilst stirring. The mixture is then heated under reflux overnight, the triethylammonium hydrochloride which was separated out is filtered off hot and washed with hot dioxane and, after cooling, a solution of 9.9 pts. by wt. of phosgene in 60 pts. by vol. of abs. dioxane is added to the filtrate. After standing for 12 hrs. at room temperature, excess phosgene is blown out of the mixture by means of dry air. The precipitate is filtered off, the filtrate is concentrated and the residue is recrystallized from abs. acetonitrile. 8.9 pts. by wt. of 1-chlorocarbonyl-2-oxo-3-(4-chloro)-benzalimino-imidazolidine of decomp. pt. 188°–192° C. IR (liquid paraffin): 1800 and 1700 cm⁻¹.

2.0 pts. by wt. of sodium epicillin in 40 pts. by vol. of 80% strength by volume THF are reacted with 3.5 pts. by wt. of 1-chlorocarbonyl-2-oxo-3-(4-chloro)-benzalimino-imidazolidine as in Example 1.5. This gives 0.4 pt. by wt. of sodium 6-{D-α-[(2-oxo-3-{4-chloro}-benzalimino-imidazolidin-1-yl)-carbonylamino]-cyclohex-1,4-dien-1-yl-acetamido}-penicillanate with a β-lactam content of 92%.

IR (KBr): 1770, 1730, 1670 and 1605 cm⁻¹.

NMR (CD₃OD): 7.78 (s, 1H), 7.76 and 7.36 (AB, 4H), 5.95 (m, 1H), 5.72 (s, 2H), 5.50 (s, 2H), 5.00 (s, 1H), 4.20 (s, 1H), 3.95 (s, broad, 4H), 2.75 (s, broad, 4H), 1.65 (s, 3H), and 1.58 (s, 3H) δ.

2.5

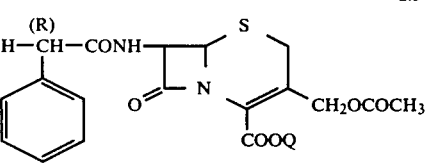

Q = H, Na 2.25 pts. by wt. of cephaloglycine dihydrate in 40 pts. by vol. of 80% strength by volume THF are reacted with 3.5 pts. by wt. of 1-chlorocarbonyl-2-oxo-3-(4-chloro)-benzalimino-imidazolidine as in Example 1.6. This gives 0.6 pt. by wt. of sodium 7-{D-α-[(2-oxo-3-{4-chloro}-benzalimino-imidazolidin-1-yl)-carbonylamino]-phenylacetamido}-3-acetoxymethyl-ceph-3-em-4-carboxylate with a 62-lactam content of 80–85%.

IR (KBr): 1760, 1720, 1660 and 1595 cm⁻¹.

2.3.

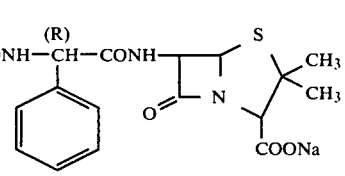

7.9 pts. by wt. of ampicillin trihydrate in 80 pts. by vol. of 80% strength by volume aqueous THF are reacted with 2.8 pts. by wt. of 1-chlorocarbonyl-2-oxo-3-(4-chloro)-benzalimino-imidazolidine as in Example 1.3. This gives 1.4 pts. by wt. of sodium 6-{D-α-[(2-oxo-3-{4-chloro}-benzalimino-imidazolidin-1-yl)-carbonylamino]-phenylacetamido}-penicillanate of decomp. pt. 210°–215° C. with a β-lactam content of 87%.

NMR (CD₃OD): 7.7 and 7.4 (m, 10H), 5.65 (d, 1H), 5.60 (s, 1H), 5.0–4.8 m (overlaid by the signal of the replaceable protons) 3.88 and 3.70 (overlaid multiplets) and 2.03 (s, 3H) δ.

C₂₉H₂₆ClN₆NaO₈S.1½ H₂O.¼ dimethylacetamide: calculated: C, 50.25; H, 4.22; N, 11.72; S, 4.48. found: C, 50.1; H, 4.5; N, 11.1; S, 5.4.

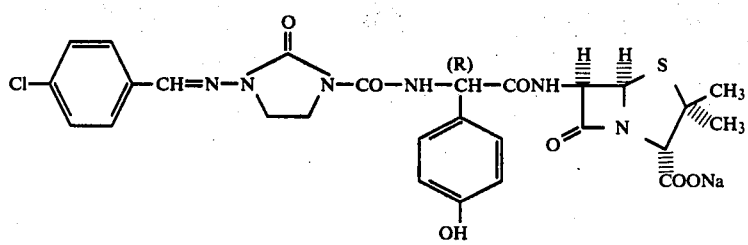

6.3 pts. by wt. of amoxicillin trihydrate in 80 pts. by vol. of 80 percent strength aqueous THF are reacted with 2.9 pts. by wt. of 1-chlorocarbonyl-2-oxo-3-(4-chloro)-benzalimino-imidazolidine as in Example 1.4. This gives 4.6 pts. by wt. of sodium 6-{D-α-[(2-oxo-3-{4-chloro}-benzalimino-imidazolidin-1-yl)-carbonylamino]-4-hydroxyphenylacetamido}-penicillanate of decomp. pt. 220°–4° C.

IR (KBr): 1775, 1730, 1670 and 1615 cm$^{-1}$.

NMR (CD$_3$OD): 6.7–8.0 (9H), 5.4–5.6 (3H), 4.95 (3 replaceable H), 4.15 (1 H), 3.80 (4H), 1.58 (3H) and 1.52 3H) δ.

$C_{27}H_{26}ClN_6NaO_7S.2H_2O$: calculated: C, 48.18; H, 4.49; N, 12.49; S, 4.77. found: C, 48.7; H, 5.1; N, 12.6; S, 4.5.

EXAMPLE 3

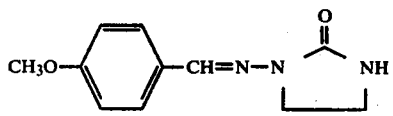

15.8 pts. by wt. of 2-oxo-imidazolidine 12.6 pts. by wt. of sodium nitrite and 27.5 pts. by wt. of zinc dust are processed as in Example 2.1. and the mixture is reacted with 22.4 pts. by wt. of 4-methoxybenzaldehyde. This gives 15.8 pts. by wt. of 1-(4-methoxy)-benzalimino-2-oxo-imidazolidine of melting point 179°–181° C.

IR (KBr): 3250, 3130, 1725, 1700 and 1605 cm$^{-1}$.

NMR (d$_6$-DMSO): 7.56 and 6.92 (AB, 4H), 7.52 (s, 1H), 7.04 (s, 1H), 3.72 (s, 3H) and m centered at 3.52 (4H) δ.

$C_{11}H_{13}N_3O_2$: calculated: C, 60.27; H, 5.97; N, 19.17. found: C, 60.3; H, 5.9; N, 18.9.

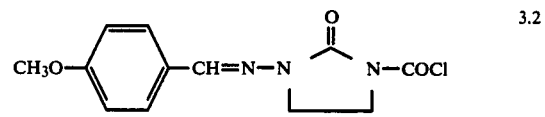

A solution of 20.0 pts. by wt. of trimethylchlorosilane in 50 pts. by vol. of abs. benzene is added dropwise to a boiling solution of 13.6 pts. by wt. of 1-(4-methoxy)-benzalimino-2-oxo-imidazolidine and 27.6 pts. by vol. of triethylamine in 120 pts. by vol. of abs. benzene and the mixture is reacted and worked up as in Example 1.2. This gives 6.2 pts. by wt. of 1-chlorocarbonyl-2-oxo-3-(4-methoxy)-benzalimino-imidazolidine of melting point 204°–208° C.

IR (liquid paraffin): 1800 cm$^{-1}$.

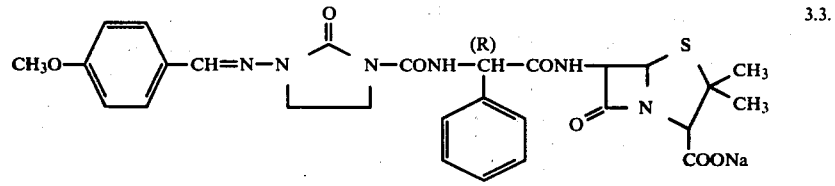

6.9 pts. by wt. of ampicillin trihydrate in 70 pts. by vol. of 80% strength by volume THF and 2.4 pts. by wt. of 1-chlorocarbonyl-2-oxo-3-(4-methoxy)-benzalimino-imidazolidine are reacted as in Example 1.3. This gives 4.5 pts. by wt. of sodium 6-{D-α-[(2-oxo-3-{4-methoxy}-benzalimino-imidazolidin-1-yl)-carbonylamino]-phenylacetamido}-penicillanate of decomp. pt. 213°–223° C. with a β-lactam content of 87%.

IR (KBr): 1770, 1730, 1675 and 1605 cm$^{-1}$.

NMR (CD$_3$OD): 7.60 and 6.85 (AB, 4H), 7.4 (m, 5+1H), 5.60 (s, 1H), 5.45 (q, 2H), 4.15 (s, 1H), 3.72 (s, 3H), 3.63 (broad s, 4H), 1.55 (s, 4H), 1.55 (s, 3H), and 1.50 (s, 3H) δ.

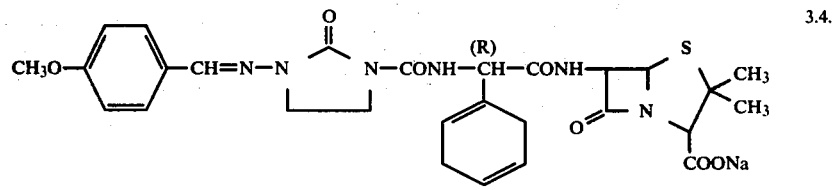

2.0 pts. by wt. of sodium epicillin in 40 pts. by vol. of 80% strength by volume THF are reacted with 2.1 pts. by wt. of 1-chlorocarbonyl-2-oxo-3-(4-methoxy)-benzalimino-imidazolidine as in Example 1.5. This gives 3.5 pts. by wt. of sodium 6-{D-α-[(2-oxo-3-{4-methoxy}-benzalimino-imidazolidin-1-yl)-carbonylamino]-cyclohex-1,4-dien-1-yl-acetamido}-penicillanate with a β-lactam content of 68%.

IR (KBr): 1760, 1720, 1655 and 1600 cm$^{-1}$.

NMR (CD$_3$OD): 7.60 and 6.85 (AB, 4H), 74.0 (s, overlaying the AB system, 1H), 5.90 (broad s, 1H), 5.67 (s, 2H), 5.50 (s, 2H), 5.00 (s, 1H), 4.20 (s, 1H), 3.77 (broad s, 4H), 2.72 (broad s, 4H), 1.65 (s, 3H) and 1.57 (s, 3H) δ.

well as 24.9 pts. by wt. of 4-nitrobenzaldehyde are reacted as in Example 2.1. The 1-(4-nitro)-benzalimino-2-oxo-imdazolidine formed is freed from impurities by boiling with ethanol; 37.6 pts. by wt. of melting point 265°-267° C.

IR (KBr): 3430, 3260, 1720, 1595 and 1570 cm$^{-1}$.

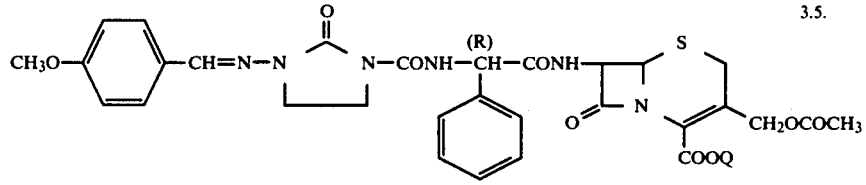

3.5.

Q = H, Na 2.25 pts. by wt. of cephaloglycine dihydrate suspended in 40 pts. by vol. of 80% strength by volume THF are reacted with 1.41 pts. by wt. of 1-chlorocarbonyl-2-oxo-3-(4-methoxy)-benzalimino-imidazolidine as in Example 1.6. and mixture is worked up. On acidifying, 7-{D-α-[(2-oxo-3-{4-methoxy}-benzalimino-imidazolidin-1-yl)-carbonylamino]-phenylacetamido}-3-acetoxymethyl-ceph-3-em-4-carboxylic acid precipitates (1.2 pts. by wt.), which is reacted with 1.9 pts. by vol. of a 1 M sodium 2-ethyl-hexanate solution as in Example 1.4 to give sodium 7-{D-α-[(2-oxo-3-{4-methoxy}-benzalimino-imidazolidin-1-yl)-carbonylamino]-phenylacetamido}-3-acetoxymethyl-ceph-3-em-4-carboxylate (0.7 pt. by wt.).

The ethyl acetate phase is worked up as in Example 1.3, whereupon a further 1.6 pts. by wt. of the sodium salt of decomp. pt. 220°-230° with a β-lactam content of 80% are obtained. IR (KBr): 1770, 1730, 1660 and 1610 cm$^{-1}$.

NMR (d$_6$-DMSO): 8.20 and 7.88 (AB, 4H), 7.68 (s, 1H), 7.37 (broad s, 1H) and m, centred at 3.65 (4H) δ.

calculated: C, 51.28; H, 4.31; N, 23.92. found: C, 51.2; H, 4.3; N, 23.9.

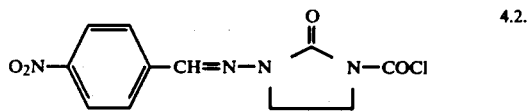

4.2.

8.8 pts. by wt. of 1-(4-nitro)-benzalimino-2-oxo-imidazolidine, 12.1 pts. by wt. of triethylamine, 12.0 pts. by wt. of trimethylchlorosilane and 3.9 pts. by wt. of phosgene are reacted as in Example 2.2. The 1-chlorocarbonyl-2-oxo-3-(4-nitro)-benzalimino-imidazolidine is recrystallised from abs. acetonitrile; 2.6 pts. by wt. of decomp. pt. 188°-192° C. result.

IR (liquid paraffin): 1800, 1760 and 1700 cm$^{-1}$.

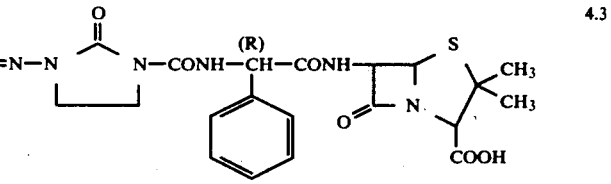

4.3

NMR (CD$_3$OD/D$_2$O): 7.55 and 6.85 (AB, 4H), 7.40 (s, overlaying the AB system, 1H), 5.67 (d, 1H), 5.47 (s, 1H), 5.15-4.85 (m, overlaid by the signal of the replaceable protons), 3.76 (broad s, 4H) and 2.05 (s, 3H) δ.

C$_{30}$H$_{29}$N$_6$NaO$_9$S.H$_2$O 690.6: calculated: C, 52.18; H, 4.52; N, 12.17; S, 4.65. found: C, 51.9; H, 4.4; N, 11.8; S, 5.1.

EXAMPLE 4

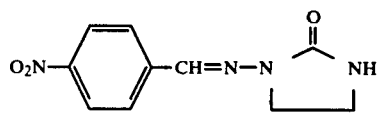

4.1.

15.8 pts. by wt. of 2-oxo-imidazolidine, 12.6 pts. by wt. of sodium nitrite and 27.5 pts. by wt. of zinc dust as 6.8 pts. by wt. of ampicillin trihydrate in 70 pts. by vol. of 80% strength by volume aqueous THF are reacted with 2.5 pts. by wt. of 1-chlorocarbonyl-2-oxo-3-(4-nitro)-benzalimino-imidazolidine as in Example 1.3. This gives 3.0 pts. by wt. of sodium 6-{D-α-[(2-oxo-3-{4-nitro}-benzaliminoidazolidin-1-yl)-carbonylamino]-phenylacetamido}-penicillanate of decomp. pt. 220°-5° C. with a β-lactam content of 98%.

IR (KBr): 1765, 1730, 1670 and 1600 cm$^{-1}$.

NMR (CD$_3$OD): 8.30 and 7.96 (AB system, 4H), 7.81 (s, 1H), m centred at 7.45 (5H), 5.64 (s, 1H), 5.57 (q, 2H), 4.20 (s, 1H), 3.88 (broad s, 4H), 1.58 (s, 3H) and 1.50 (s, 3H) δ.

C$_{27}$H$_{26}$N$_7$NaO$_8$S.2.5 H$_2$O: calculated: C, 47.93; H, 4.62; N, 14.50; S, 4.74. found: C, 47.7; H, 4.3; N, 14.4; S, 4.8.

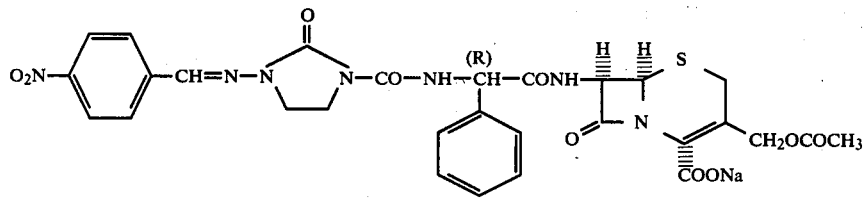
4.4.

6.5 pts. by wt. of cephaloglycine dihydrate in 80 pts. by vol. of 80 percent strength aqueous THF are reacted with 4.4 pts. by wt. of 1-chlorocarbonyl-2-oxo-3-(4-nitro)-benzalimino-imidazolidine as in Example 3.5.

This gives 9.3 pts. by wt. of sodium 7-{D-α-[(2-oxo-3-{4-nitro}-benzalimino-imidazolidin-1-yl)-carbonylamino]-phenylacetamido}-3-acetoxy-methyl-ceph-3-em-4-carboxylate of decomp. pt. 220°-5° C.

IR (KBr): 1760, 1730, 1660 and 1605 cm$^{-1}$.

$C_{29}H_{26}N_7NaO_{10}S.2$ $H_2O$: calculated: C, 48.13; H, 4.19; N, 13.56; S, 4.42. found: C, 48.0; H, 4.1; N, 13.4; S, 4.4.

EXAMPLE 5

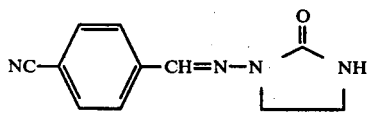
5.1.

12.6 pts. by wt. of 2-oxo-imidazolidine, 10.1 pts. by wt. of sodium nitrite and 21.8 pts. by wt. of zinc dust are processed as in Example 2.1. and reacted with 17.3 pts. by wt. of 4-cyanobenzaldehyde. This gives 26.2 pts. by wt. of 1-(4-cyano)-benzalimino-2-oxo-imidazolidine, which is freed from impurities by successive washing with water, ethanol and ether. Melting point 265°-267° C.

(IR (KBr): 3210, 3120, 2220, 1720 and 1590 cm$^{-1}$.

NMR (d$_6$-DMSO): b 7.88 (s, 4H), 7.66 (s, 1H), 7.30 (broad s, 1H), and m centred at 3.7 (4H) δ.

calculated: C, 61.68; H, 4.71; N, 26.15. found: C, 59.8; H, 4.6; N, 25.9.

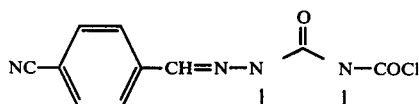
5.2.

7.5 pts. by wt. of 1-(4-cyano)-benzalimino-2-oxo-imidazolidine and 12.1 pts. by wt. of triethylamine in 60 pts. by vol. of abs. dioxane as well as 12.0 pts. by wt. of trimethylchlorosilane in 25 pts. by vol. of abs. dioxane and 3.9 pts. by wt. of phosgene are reacted as in Example 2.2. The 1-chlorocarbonyl-2-oxo-3-(4-cyano)-benzalimino-imidazolidine is recrystallised from abs. acetonitrile; 4.7 pts. by wt. of melting point 260°-264° C. result. IR (liquid paraffin): 1800 cm$^{-1}$.

calculated: C, 52.09; H, 3.28; N, 20.25; Cl, 12.82. found: C, 52.0; H, 3.3; N, 20.3; Cl, 12.5.

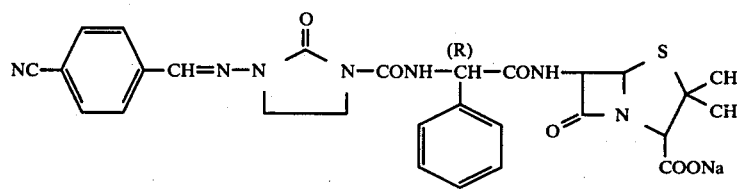
5.3.

7.9 pts. by wt. of ampicililn trihydrate in 80 pts. by vol. of 80strength by volume aqueous THF are reacted with 2.7 pts. by wt. of 1-chlorocarbonyl-2-oxo-3-(4-cyano)-benzalimino-imidazolidine as in Example 1.3. This gives 2.3 pts. by wt. of sodium 6-{D-α-[(2-oxo-3-{4-cyano}-benzalimino-imidazolidine-1-yl)-carbonylamino]-phenylacetamido}-pencillanate of decomp. pt. 225°-230° C. with a β-lactam content of 88%.

IR (KBr): 2220, 1770, 1730, 1665 and 1600 cm$^{-1}$.

NMR (CD$_3$OD): 7.95–7.20 (10H), 5.56 (s, 1H), 5.42 (q, 2H), 4.12 (s, 1H), 3.87 (broad s, 4H), 1.57 (s, 3H) and 1.48 (s, 3H) δ.

$C_{28}H_{26}N_7NaO_6S$. 2.5 $H_2O$: calculated: C, 51.21; H, 4.76; N, 14.93. found: C, 51.6; H, 4.9; N, 14.4.

EXAMPLE 6

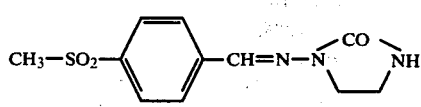
6.1.

This substance is prepared from 15.8 pts. by wt. of imidazolidone and 31.0 pts. by wt. of 4-methylsulphonylbenzaldehyde in the manner described in Example 1.1, but in a 1:1 (volume) water/dichloromethane mixture. The crude product is recrystallised from nitromethane.

Yield- 9.2 pts. by wt. of 1-(4-methylsulphonyl)-benzalimino-2-oxo-imidazolidine, melting point =b 264° C. NMR signals at τ=2.0 (4H), 2.2 (1H), 5.9–6.65 (4H) and 6.7 ppm (3H).

calculated: C, 49.4; H, 4.9; N, 15.7; O, 18.0; S, 12.0. found: C, 48.6; H, 5.0; O, 18.3; S, 12.1.

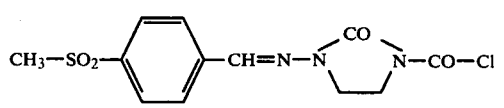
6.2.

Ths substance is prepared from 9.2 pts. by wt. of 1-(4-methylsulphonyl)-benzalimino-2-oxo-imidazolidine in the manner described in Example 1.2. The crude product is recrystallised from nitromethane and acetonitrile. Yield 5.4 pts. by wt. of 1-chlorocarbonyl-2-oxo-3-(4-methylsulphonyl)-benzalimino-imidazolidine.

Melting point =208°–213° C.

calculated: C, 43.7 ; H, 3.6; Cl, 10.8; N, 12.8; S, 9.7. found: C, 43.8; H, 4.9; Cl, 10.2; N, 12.5; S, 9.5.

as the soduim salt. Yield: 2.0 pts. by wt. of the sodium salt of D-α-{[2-oxo-3-(b 4-methylsulphonyl)-benzalimino-imidazolidin-1-yl)]-carbonylamino}-p-hydroxybenzylpenicillin.

β-Lactam content: 85 .

6.3.

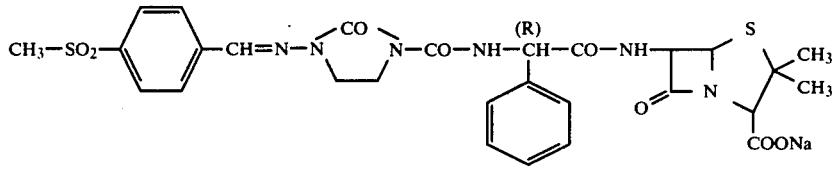

Ths penicillin is prepared from ampicillin trihydrate (2.0 pts. by wt.) and 1-chlorocarbonyl-2-oxo-3-(4-methylsulphonyl)-benzalimino-imidazolidine (1.6 pts. by wt.) in the manner described in Example 1.3. In this procedure, the pencillic acid separates out as a crystalline precipitate (1.6 pts by wt.) which is insoluble in water and ethyl acetate. Ths penicillic acid is dissolved in a ittle dimethylformamide, the calculated amount of sodium 2-ethylhexanoate solution (in methanol-containing ether) is added and the sodium salt of the penicillin According to the NMR spectrum, this penicillin contains about 0.2 mols of water, 0.25 mol of ethyl acetate, 0.7 mol of dimethylformamide and 0.08 mol of sodium 2-ethylhexanoate. This was taken into consideration in the calculated analysis data.

calculated: C, 47.4; H, 5.1; N, 11.7; S, 8.0. found: C, 47.2; H, 5.0; N, 11.1; S, 7.9.

NMR signals at τ=2.1 (4H), 2.2 (1H), 2.5–3.3 (4H), 4.35–4.65 (3H), 5.8 (1H), 5.9–6.4 (4H), 6.85 (3H) and 8.2–8.7 ppm (6H).

6.5.

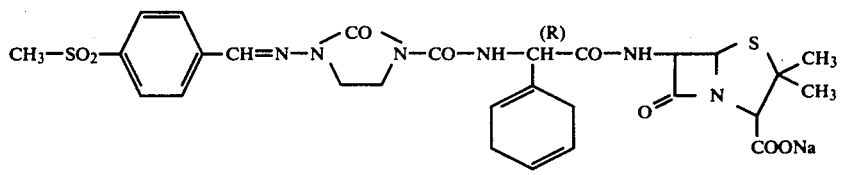

is precipitated by pouring the mixture into a large amount of ether.

Yield: 0.85 pt. by wt. of the sodium salt of D-α-{[2-oxo-3-(4-methylsulphonyl)-benzalimino-imidazolidin-1-yl]-carbonylamino}-benzylpenicillin.

β-Lactam content: 90%.

According to the NMR spectrum, the penicillin contains about 1.5 mols of water, 0.2 mol of ethyl acetate, 0.25 mol of dimethylformamide and 0.15 mol of sodium 2-ethylhexanoate. This was taken into consideration in the calculated analysis values:

calculated: C, 49.1; H, 5.1; N, 11.6; S, 8.5. found: C, 48.5; H, 4.8; N, 11.8; S, 8.4.

NMR signals at τ=2.05 (4H), 2.2 (1H), 2.2–2.8 (5H), 4.3–4.65 (3H), 5.8 (1H), 5.9–6.4 (4H), 6.85 (3H) and 8.2–8.7 pm (6H).

This penicillin is obtained from epicillin (1.0 pt. by wt.) and 1-chlorocarbonyl-2-oxo-3-(4-methylsulphonyl)-benzalimino-imidazolidine (0.94 pt. by wt.) in the manner described in Example 1.3. and 6.3., first as the crystalline penicillic acid (1.8 pts. by wt.) and then as the sodium salt. Yield: 1.6 pts. by wt. of the sodium salt of D-α-{[b 2-oxo-3-(4-methylsulphonyl)-benzalimino-imidazolidin-1-yl]-carbonylamino}-α-(1,4-cyclohexadiene-1-yl)-methylpenicillin.

β-Lactam content: 81%.

According to the NMR spectrum, this penicillin contains about 3.0 mols of water, 0.3 mol of ethyl acetate, 0.4 mol of dimethylformamide and 0.12 mol of sodium 2-ethylhexanoate. This was taken into consideration in the calculated analysis values:

calculated: C, 47.3; H, 5.5; N, 11.3; S, 8.1. found: C, 6.4.

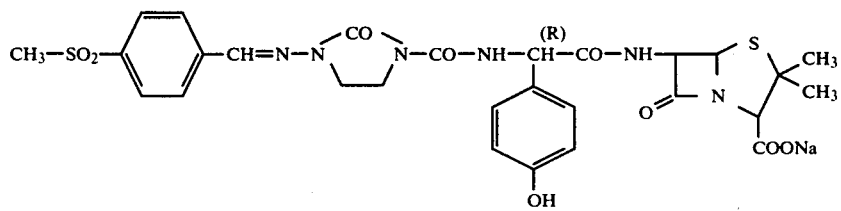

This penicillin is obtained from amoxicillin (1.5 pts. by wt.) and 1-chlorocarbonyl-2-oxo-3-(4-methylsulphonyl)-benzalimino-imidazolidine (1.18 pts. by wt.) in the manner described in Example 1.3. and 6.3., first as the crystalline penicillic acid (1.8 pts. by wt.) and then 46.9; H, 5.5; N, 11.3; S, 8.1.

NMR signals at τ=2.0 (4H), 2.15 (1H), 4.0 (1H), 4.25 (2H), 4.45 (2H), 5.0 (1H), 5.8 (1H), 5.8–6.3 (4H), 6.8 (3H), 7.0–7.4 (4H), and 8.2–8.7 ppm (6H).

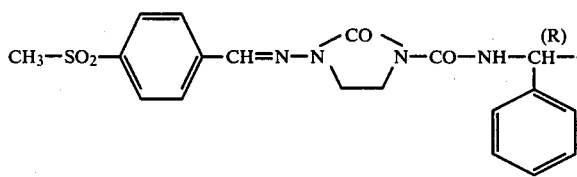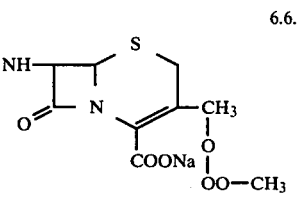

6.6.

This cephalosporin is obtained from cephaloglycine (1.5 pts. by wt.) and 1-chlorocarbonyl-2-oxo-3-(4 methylsulphonyl)-benzalimino-imidazolidine (1.0 pt. by wt.) in the manner described in Example 1.3. and 6.3., partially first as the crystalline acid (portion undissolved in ethyl acetate and water) (1.0 pt. by wt.) and partially directly as the sodium salt (portion dissolved in ethyl acetate and precipitated from this as the sodium salt) (0.75 pt. by wt.) Still further sodium salt is then prepared from the penicillic acid as described in Example 6.3. Total yield: 1.85 pts. by wt. of sodium 7 D-α-[{2-oxo-3-(4-methylsulphonyl)-benzalimino-imidazolidin-1-yl]-carbonylamino}-phenylacetamido]-3-acetoxymethyl-ceph-3-em-4-carboxylate.

β-Lactam content: 84%.

According to the NMR spectrum, ths cephalosporin contains about 1.7 mols of water, 0.4 mol of dimethylformamide, 0.4 mol of ethyl acetate and 0.16 mol of sodium 2-ethylhexanoate. This was taken into consideration in the calculated analysis figures:

calculated: C, 47.4; H, 4.6; N, 10.5; S, 7.5. found: C, 47.3; H, 4.2; N, 10.8; S, 8.1.

NMR signals at τ=2.1 (4H), 2.25 (1H), 2.5–2.9 (5H), 4.3–4.6 (2H), 5.05–5.3 (3H), 6.0–6.3 (4H), 6.7 (2H), 6.9 (3H) and 8.0 ppm (3H).

IR (KBr): 3240 and 1705 (broad) cm$^{-1}$.

NMR (d$_6$-DMSO): 7.88 (s, 1H), 7.3–7.0 (heteroaromatic protons, as well as NH, 4H) and m, centred at 3.6 (4H).

calculated: C, 49.22; H, 4.65; N, 21.52; S, 16.42. found: C, 49.4; H, 4.6; N, 21.4; S, 16.1.

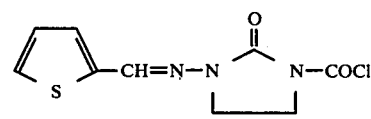

7.2.

9.8 pts. by wt. of 1-(thiophene-2-aldimino)-2-oxo-imidazolidine, 16.2 pts. by wt. of triethylamine, 16.1 pts. by wt. of trimethylchlorosilane and 5.1 pts. by wt. of phosgene are reacted as in Example 1.2. This gives 7.7 pts. by wt. of 1-chlorocarbonyl-2-oxo-3-(thiophene-2-aldimino)-imidazolidine of decomp. pt. 184°–188° C.

IR (liquid paraffin): 1830 and 1720 cm$^{-1}$.

The chlorocarbonyl compound still contains starting material, which was not removed since it does not interfere with the subsequent reactions.

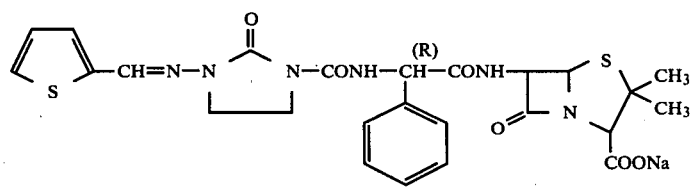

7.3.

EXAMPLE 7

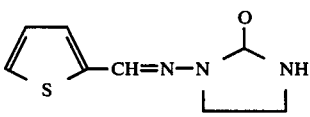

7.1.

15.8 pts. by wt. of 2-oxo-imidazolidine, 12.6 pts. by wt. of sodium nitrite and 27.5 pts. by wt. of zinc dust as well as 18.5 pts. by wt. of thiophene-2-aldehyde are reacted as in Example 1.1. The 1-(thiophene-2-aldimino)-2-oxo-imidazolidine formed is freed from impurities by boiling with ethanol or is recrystallised from dimethylformamide. b 22.4 pts. by wt. of melting point 263°–265° C.

2.6 pts. by wt. of 1-chlorocarbonyl-2-oxo-3-(thiophene-2-aldimino)-imidazolidine and 4.1 pts. by wt. of ampicillin trihydrate in 40 pts. by vol. of 80% strength by volume aqueous THF are reacted as in Example 1.3. This gives 0.4 pt. by wt. of sodium 6-{D-α-[(2-oxo-3-{thiophene-2-aldimino}-imidazolidin-1-yl)-carbonylamino]-phenylacetamido}-penicillanate of decomp. pt. 210°–220° C. with a β-lactam content of 89%.

IR (KBr): 1760, 1720, 1660 and 1600cm$^{-1}$.

NMR (CD$_3$OD): 7.90 (s, 1H), 7.5–6.8 (aromatic and hetero-aromatic protons, 8H), 5.51 (s, with overlaying m at about 5.4, together with 3H), 4.12 (s, 1H), 3.79 (broad s, 4H), 1.57 (s, 3H) and 1.48 (s, 3H) δ. C$_{25}$H$_{25}$N$_6$NaO$_6$S$_2$.2.5 H$_2$O.0.25 ether; 656.1 calculated: C, 47.60; H, 5.00; N, 12.81; S, 9.79. found: C, 47.6; H, 5.5; N, 12.4; S, 10.0.

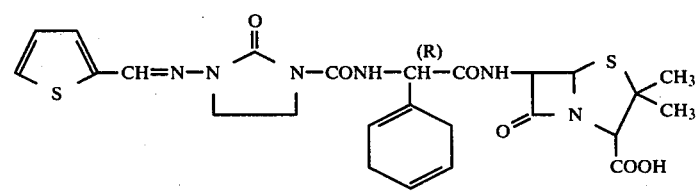

7.4.

2.6 pts. by wt. of 1-chlorocarbonyl-2-oxo-3-(thiophene-2-aldimino)-imidazolidine and 2.0 pts. by wt. of sodium epicillin in 40 pts. by vol. of 80% strength by volume aqueous THF are reacted as in Example 1.5. This gives 0.8 pt. by wt. of sodium 6-{D-α-[(2-oxo-3-{thiophene-2-aldimino{-imidazolidin-1-yl)-carbonylamino]-cyclohex-1,4-dien-1-yl-acetamido}-penicillanate of decomp. pt. 205°-215° C. with a β-lactam content of 89%.

IR (KBr): 1770, 1730, 1665 and 1605 cm$^{-1}$.

NMR (CD$_3$OD): 8.00 (s, 1H), 7.5-7.0 (heteroaromatic protons, 3H), 5.95 (broad s, 1H), 5.70 (s, 2H), 5.50 (s, 2H), 5.00 (s, 1H), 4.20 (s, 1H), 3.86 (broad s, 4H), 2.73 (broad s, 4H), 1.64 (s, 3H) and 1.57 (s, 3H) δ.

C$_{25}$H$_{27}$N$_6$NaO$_6$S$_2$.2 H$_2$O, 530.6: calculated: C, 47.61; H, 4.95; N, 13.32; S, 10.16. found: C, 47.6; H, 5.1; N, 13.0; S, 10.2.

15.8 pts. by wt. of 2-oxo-imidazolidine, 12.6 pts. by wt. of sodium nitrite and 27.5 pts, by wt. of zinc dust as well as 15.8 pts. by wt. of furane-2-aldehyde are reacted as in Example 1.1. This gives 17.5 pts. by wt. of 1-furylideneamino-2-oxo-imidazolidine of melting point 218°-220° C.

IR (KBr): 3200, 3110, 1715 and 1585 cm$^{-1}$.

NMR (d$_6$-DMSO): 7.70 (m, 1H), 7.50 (s, 1H), 7.15 (broad s, 1H), 6.50-6.75 (m, 2H) and m, centred at 3.55 (4H) δ.

calculated: C, 53.63; H, 5.06; N, 23.45. found: C, 53.7; H, 5.0; N, 23.2.

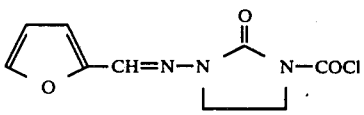
8.2.

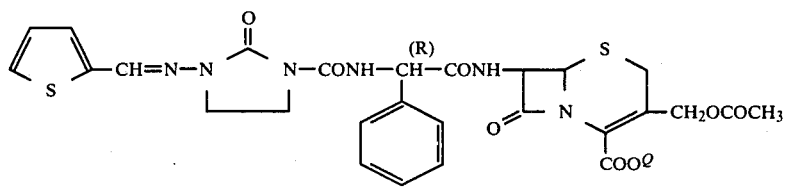
7.5.

Q = H, Na 1.50 pts. by wt. of 1-chlorocarbonyl-2-oxo-3-(thiophene-2-aldimino)-imidazolidine and 2.25 pts. by wt. of cephaloglycine dihydrate in 40 pts. by vol. of 80% strength by volume THF are reacted as in Example 1.6. On acidifying, 7-{D-α-[(2-oxo-3-{thiophene-2-aldimino}-imidazolidin-1-yl)-carbonylamino]-phenylacetamido}-3-acetoxymethyl-ceph-3-em-4-carboxylic acid precipitates (0.6 pt. by wt.), which is reacted with 3 pts. by vol. of a 1 M sodium 2-ethyl-hexanoate solution as in Example 1.4. to give sodium 7-{D-α-[(2-oxo-3-{thiophene-2-aldimino}-imidazolidin-1-yl)-carbonylamino]-phenylacetamido}-3-acetoxymethyl-ceph-3-em-4-carboxylate.

The β-lactam content is 75–80%.

IR (KBr): 1755, 1720, 1660 and 1600 cm$^{-1}$.

NMR (CD$_3$OD): 7.95 (s, 1H), 7.5–6.8 (aromatic and hetero-aromatic protons, 8H), 5.75–5.00 (m, 3H), 4.8 (overlaid by the signal of the replaceable protons), 3.82 (broad s, 4H) and 2.00 (s, 3H) δ. cl EXAMPLE 8

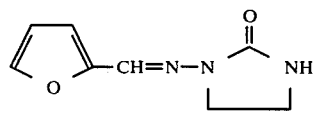
8.1.

11.5 pts. by wt. of 1-furylideneamino-2-oxo-imidazolidine, 10.0 pts. by wt. of triethylamine, 13.2 pts. by wt. of trimethylchlorosilane and 6.2 pts. by wt. of phosgene are reacted as in Example 1.2. This gives 3.8 pts. by wt. of 1-chlorocarbonyl-2-oxo-3-furylideneamino-imidazolidine of decomp. pt. 130° C.

IR (liquid paraffin): 1800 and 1700 cm$^{-1}$. The chlorocarbonyl compound still contains starting material, which was not removed since it does not interfere with the subsequent reactions.

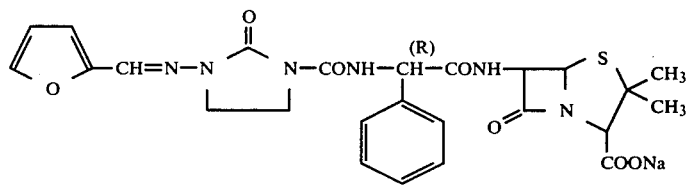
8.3.

6.1 pts. by wt. of 1-chlorocarbonyl-2-oxo-3-(furane-2-aldimino)-imidazolidine and 20.4 pts. by wt. of ampicillin trihydrate in 200 pts. by vol. of 80% strength by volume aqueous THF are reacted as in Example 1.3. This gives 2.3 pts. by wt. of sodium 6-{D-α-[(2-oxo-3-furylideneamino-imidazolidin-1-yl)-carbonylamino]-phenylacetamido}-penicillanate of decomp. pt. 200°-207° C. with a β-lactam content of 81%.

IR (KBr): 1760, 1715, 1660 and 1600 cm$^{1\ 1}$.

NMR (CD$_3$OD): 7.60 (s, 1H), 7.50–6.35 (aromatic and hetero-aromatic protons, 8H), 5.55 (s, 1H), 5.40 (q, 2H), 4.12(s, 1H), m, centred at 3.75 (4H), 1.55 (s, 3H) and 1.48 (s, 3H) δ.

C$_{24}$H$_{25}$N$_6$NaO$_7$S.1.5 H$_2$O.0.25 ether: calculated: C, 49.22; H, 5.04; N, 13.76; S, 5.26. found: C, 49.5; H, 4.8; N, 13.5; S, 5.2.

8.4.

[Structural formula: furyl-CH=N-N(imidazolidinone)-CONH-CH(R)(phenyl)-CONH-β-lactam-CH2OCOCH3, COOQ]

Q = H, Na 10.0 pts. by wt. of cephaloglycine dihydrate in 100 pts. by vol. of 80 percent strength aqueous THF and 6.1 pts. by wt. of 1-chlorocarbonyl-2-oxo-3-furylideneamino-imidazolidine are reacted as in Example 1.6. and the mixture is worked up. On slowly acidifying with 0.1 N HCL at 5°-10° C., 13.1 pts. by wt. of crystalline acid (Q=H) precipitate. This precipitate is dissolved in 500 pts. by vol. of acetone, the small proportion of insoluble material is filtered off and the filtrate is concentrated. The residue is suspended in 120 pts. by vol. of water and 1.5 N sodium hydroxide solution is added until the solid dissolves, the pH being kept between 7.5 and 8.0. The mixture is filtered, 940 pts. by vol. of acetone and then 190 pts. by vol. of ethyl acetate are added to the filtrate and the sodium salt is then precipitated by adding 380 pts. by vol. of ether dropwise. This gives 7.8 pts. by wt. of crystalline sodium 7-{D-α-[(2-oxo-3-furylideneamino-imidazolidin-1-yl)-carbonylamino]-phenylacetamido}-3-acetoxymethyl-ceph-3-em-4-carboxylate of decomp. pt. 215°-220° C. with a β-lactam content of 95%.

IR (KBr): 1765, 1730, 1670, 1615, 1530, 1480, 1390, 1265, 1230, 1020, 740 and 695 cm$^{-1}$.

NMR (D$_2$O/CD$_3$OD): 7.50 (s, 2H), 7.30 (s, 5H), 6.65 (1H), 6.45 (1H), 5.56 (d, 1H), 5.38 (s, 1H), 4.91 (pseudo d, overlaid by the signal of the replaceable protons), 3.76 (6H) and 2.03 (s, 3) δ.

C$_{27}$H$_{25}$N$_6$NaO$_9$S.H$_2$O: calculated: C, 49.84; H, 4.18; N, 12.91; S, 4.92. found: C, 49.4; H, 4.6; N, 12.9; S, 4.9.

EXAMPLE 9

9.1.

[Structure: 2-chlorothiophene-CH=N-N(imidazolidinone)-NH]

18.9 pts. by wt. of 2-oxo-imidazolidine, 15.2 pts. by wt. of sodium nitrite and 33.2 pts. by wt. of zinc dust are processed as in Example 2.1. and reacted with 29.1 pts. by wt. of 2-chlorothiophene-5-aldehyde. This gives 36.0 pts. by wt. of 1-(2-chlorothiophene-5-aldimino)-2-oxo-imidazolidine, which was purified by successive washing with water, ethanol and ether. Melting point 194°-197° C.

IR (KBr): 3260, 1700 (broad) and 1580 cm$^{-1}$.

NMR (d$_6$-DMSO): 7.92 and 7.78 (s, together 1H, syn-form and anti-form), 7.16 and 7.10 (AB with overlaid NH, 3H) and m, centred at 3.6 (4H) δ.

calculated: C, 41.84; H, 3.51; N, 18.28; S, 13.96. found: C, 41.9; H, 3.8; N, 18.0; S, 14.3.

9.2.

[Structure: 2-chlorothiophene-CH=N-N(imidazolidinone)-N-COCl]

8.6 pts. by wt. of 1-(2-chlorothiophene-5-aldimino)-2-

8.5.

[Structural formula: furyl-CH=N-N(imidazolidinone)-N-CO-NH-CH(R)(4-hydroxyphenyl)-CONH-β-lactam-C(CH3)2, COONa]

9.4 pts. by wt. of amoxicillin trihydrate in 100 pts. by vol. of 80 percent strength aqueous THF are reacted with 5.5 pts. by wt. of 1-chlorocarbonyl-2-oxo-3-(furane-2-aldimino)-imidazolidine as in Example 1.4. This gives (0.1 pts. by wt. of sodium 6-{D-α-[(2-oxo-3-furylideneamino-imidazolidin-1-yl)-carbonylamino]-4-hydroxyphenylacetamido}-penicillanate.

IR (KBr): 1775, 1730, 1670 and 1615 cm$^{-1}$.

NMR (CD$_3$OD): 7.7-6.6 (8H), 5.5 (3H), 4.18 (s, 1H), 3.90 (s, 4H), 1.58 (s, 3H) and 1.50 (s, 3H) δ.

oxo-imidazolidine and b 12.1 pts. by wt. of triethylamine in 60 pts. by vol. of abs. dioxane as well as 12.0 pts. by wt. of trimethylchlorosilane in 25 pts. by vol. of abs. dioxane and 3.9 pts. by wt. of phosgene are reacted as in Example 2.2. The precipitate which separates out after driving off excess phosgene is filtered off and dried. This gives 5.1 pts. by wt. of 1-chlorocarbonyl-2-oxo-3-(2-chlorothiophene-5-aldimino)-imidazolidine of decomp. pt. 215°-220° C.

IR (liquid paraffin): 1800 cm$^{-1}$.

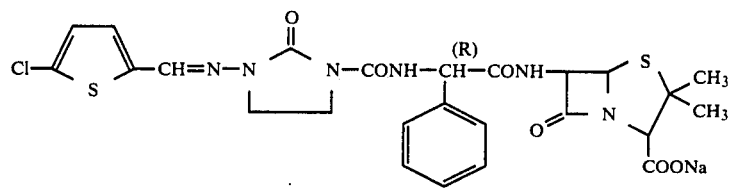

9.3.

13.9 pts. by wt. of ampicillin trihydrate in 140 pts. by vol. of 80% strength by volume aqueous THF are reacted with 5.0 pts. by wt. of 1-chlorocarbonyl-2-oxo-3-(2-chlorothiophene-5-aldimino)-imidazolidine as in Example 1.3. This gives 7.5 pts. by wt. of sodium 6-{D-α-[(2-oxo-3-{2-chlorothiophene-5-aldimino}-imidazolidin-1-yl)-carbonylamino]-phenylacetamido}-penicillanate of decomp. pt. 215°–225° C. with a β-lactam content of 90%.

IR (KBr): 1765, 1730, 1670 and 1605 cm$^{-1}$.

NMR (CD$_3$OD): 7.77 (s, 1H), m, centred at 7.32 (5H), 7.06 and 6.83 (AB, 2H), 5.55 (s, 1H), 5.42 (q, 2H), 4.13 (s, 1H), 3.77 (broad s, 4H), 1.56 (s, 3H) and 1.48 (s, 3H) δ.

$C_{25}H_{24}ClN_6NaO_6S_2 \cdot 1$ H$_2$O. ¼ ether: calculated: C, 47.10; H, 4.33; N, 12.68; S, 9.68; Cl, 5.35. found: C, 47.0; H, 4.2; N, 12.5; S, 9.5; Cl, 4.9.

EXAMPLE 10

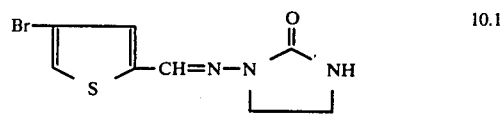

10.1

15.8 pts. by wt. of 2-oxo-imidazolidine, 12.6 pts. by wt. of sodium nitrite and 27.5 pts. by wt. of zinc dust are processed as in Example 2.1. and the mixture is reacted with 31.5 pts. by wt. of 3-bromothiophene-5-aldehyde. This gives 41.2 pts. by wt. of 1-(3-bromothiophene-5-aldimino)-2-oxo-imidazolidine, which is purified by successive washing with water, ethanol and ether and recrystallised from DMF.

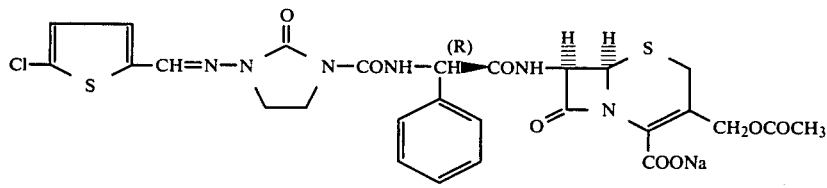

9.4

Melting point 253°–255° C.

IR (KBr): 3230 and 1710 cm$^{-1}$.

NMR (d$_6$-DMSO): 7.77 (s, 1H), 7.60 (s, 1H), 7.28 (s, 1H), 7.24 (s, 1H) and m, centred at 3.6 (4H).

calculated: C, 35.04; H, 2.93; N, 15.33; S, 11.70; Br, 29.15. found: C, 34.7; H, 2.9; N, 15.5; S, 11.8; Br, 29.2.

2.5 pts. by wt. of cephaloglycine dihydrate in 50 pts. by vol. of 80 percent strength THF are reacted with 1.7 pts. by wt. of 1-chlorocarbonyl-2-oxo-(2-chlorothiophene-5-aldimino)-imidazolidine as in Example 1.6. and the mixture is worked up. This gives 2.5 pts. by wt. of sodium 7-{D-α-(2-oxo-3-{2-chlorothiophene-5-aldimino}-imidazolidin-1-yl)-carbonylamino]-phenylacetamido}-3-acetoxymethyl-ceph-3-em-4-carboxylate.

IR (KBr): 1760, 1730, 1670 and 1600 cm$^{-1}$.

NMR (CD$_3$OD/D$_2$O): 7.87 (s, 1H), 7.50 (s, 5H), 7.18 (d, 1H), 6.93 (d, 1H), 5.65 (d, 1H), 5.53 (s, 1H), 5.05 (overlaid by the signal of the replaceable protons), 3.83 (6H) and 2.10 (s, 3H) δ.

$C_{27}H_{24}ClN_6O_8S_2 \cdot H_2O$: calculated: C, 46.26; H, 3.74; N, 11.99; S, 9.14; Cl, 5.07. found: C, 46.3; H, 3.9; N, 11.9; S, 9.5; Cl, 5.0.

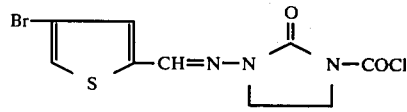

10.2.

12.2 pts. by wt. of 1-(3-bromothiophene-5-aldimino)-2-oxo-imidazolidine and 14.1 pts. by wt. of triethylamine in 120 pts. by vol. of abs. dioxane as well as 14.0 pts. by wt. of trimethylchlorosilane in 50 pts. by vol. of abs. dioxane and 4.6 pts. by wt. of phosgene are reacted as in Example 2.2. The precipitate which separates out after driving off excess phosgene is filtered off, the filtrate is concentrated and the residue is triturated with abs. ether and filtered off. This gives 7.5 pts. by wt. of 1-chlorocarbonyl-2-oxo-3-(3-bromothiophene-5-aldimino)-imidazolidine of melting point 165–170, which still contains a proportion of starting material.

IR (liquid paraffin): 1780 and 1690 cm$^{-1}$.

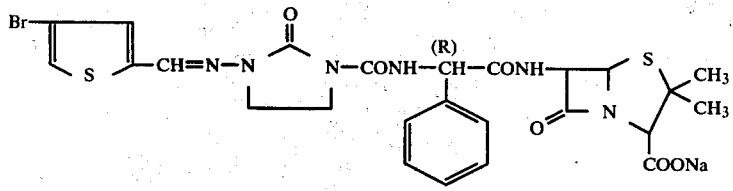

10.3.

6.5 pts. by wt. of ampicillin trihydrate in 70 pts. by vol. of 80% strength by volume aqueous THF and 2.7 pts. by wt. of 1-chlorocarbonyl-2-oxo-3-(3-bromothiophene-5-aldimino)-imidazolidine are reacted as in Example 1.3. This gives 2.2 pts. by wt. of sodium 6-{D-α-[(2-oxo-3-{3-bromothiophene-5-aldimino}-imidazolidin-1-yl)-carbonylamino]-phenylacetamido}-penicillanate of decomp. pt. 210°–220° C., with a β-lactam content of 85%.

IR (KBr): 1765, 1730, 1675 and 1610 cm$^{-1}$.

NMR (CD$_3$OD): 7.83–7.20 (8H), 5.53 (s, 1H), 5.42 (q, 2H), 4.12 (s, 1H), 3.78 (broad s, 4H), 1.55 (s, 3H) and 1.48 (s, 3H) δ.

$C_{25}H_{24}BrN_6NaO_7S_2.H_2O$: calculated: C, 41.50; H, 3.91; S, 8.84. found: C, 41.7; H, 4.3; S, 8.3.

EXAMPLE 11

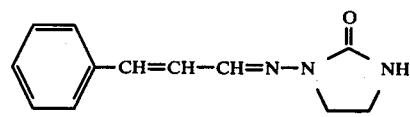

11.1.

Cinnamaldehyde (18.5 pts. by wt.) are added to a solution of 1-amino-2-oxo-imidazolidine hydrochloride (21 pts. by of 1-amino-2-oxo-imidazolidine hydrochlo-

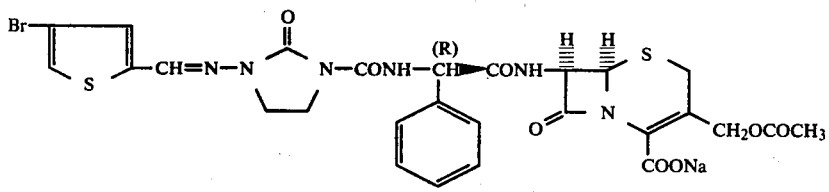

10.4.

6.5 pts. by wt. of cephaloglycine dihydrate in 80 pts. by vol. of 80 percent strength aqueous THF are reacted with 5.0 pts. by wt. of 1-chlorocarbonyl-2-oxo-3-(3-bromothiophene-5-aldimino)-imidazolidine as in Example 1.6. and the mixture is worked up. This gives 4.2 pts. by wt. of sodium 7-{D-α-[(2-oxo-3-{3-bromothiophene-5-aldimino}-imidazolidin-1-yl)-carbonylamino]-phenylacetamido}-3-acetoxymethyl-ceph-3-em-4-carboxylate of decomp. pt. 190°–5° C.

IR (KBr): 1760, 1725, 1670 and 1605 cm$^{-1}$.

$C_{27}H_{24}Br_6NaO_8S_2.H_2O$: calculated: C, 43.50; H, 3.52; N, 11.28; S, 8.59. found: C, 43.8; H, 3.8; N, 10.8; S, 8.1.

ride (21 pts. by wt.) in 1 N sodium hydroxide soluton (150 pts. by vol.) at 20° C., whilst stirring, and the mixture is subsequently stirred for a further 90 minutes at the same temperature and then left to stand for 16 hrs. The precipitate which separates out is filtered off, washed thoroughly with water and dried over P$_4$O$_{10}$ in a desiccator.

Yield: 29.9 pts. by wt.

Melting point=209°–210° C. (Kofler stage)

The substance still contains 0.28 molar equivalents of water. This is taken into consideration in the following calculated analysis values:

calculated: C, 65.4; H 6.1; N, 19.1. found: C, 65.5; H, 6.1; N, 19.1.

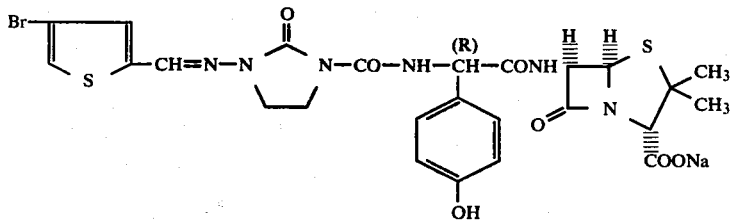

10.5.

7.5 pts. by wt. of amoxicillin trihydrate in 100 pts. by vol. of 80 percent strength aqueous THF are reacted with 6.0 pts. by wt. of 1-chlorocarbonyl-2-oxo-3-(3-bromothiophene-5-aldimino)-imidazolidine as in Example 1.4. This gives 4.3 pts. by wt. of sodium 6-{D-α-[(2-oxo-3-{3-bromothiophene-5-aldimino}-imidazolidin-1-yl)-carbonylamino]-4-hydroxyphenyl-acetamido}-penicillanate.

IR (KBr): 1760, 1720, 1670 and 1605 cm$^{-1}$.

NMR (CD$_3$OD): 7.80 (s, 1H), 6.6–7.4 (6H), 5.5 (m, 3H), 4.12 (s, 1H), 3.78 (s, broad, 4H), 1.54 (s, 3H) and 1.48 (s, 3H) δ.

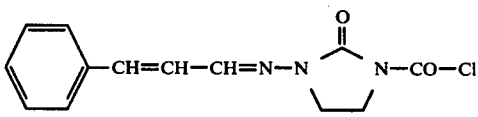

11.2.

A solution of phosgene (4.3 pts. by vol.) in benzonitrile (15 pts. by vol.) is added dropwise to a mixture of 1-(cinnamylidene-amino)-2-oxo-imidazolidine (10 pts. by wt.), benzonitrile (50 pts. by vol.) and triethylamine (7.7 pts. by vol.), whilst stirring and cooling with ice/-water. The mixture is then subsequently stirred for 4.5 hrs., with further cooling. The precipitate which has formed is then filtered off, stirred in about 30 pts. by vol. of dichloromethane for 2 hrs. at 20° C., filtered off again and then dried over $P_4O_{10}$ in a desiccator.

Yield: 8.2 pts. by wt.

Melting point=277°-230° C. (Kofler stage)

The substance still contains triethylamine hydrogen chloride, which, however, is not troublesome during the further reaction.

IR spectrum (—CO—Cl): 1800 cm$^{-1}$ (in liquid paraffin).

namylidene amino)-imidazolidine (1.49 pts. by wt.) in the manner described in Example 1.3.

Yield: 1.3 pts. by wt. of sodium D-α-[(2-oxo-3-cinnamylideneamino-imidazolidin-1-yl)-carbonylamino]-p-hydroxybenzylpenicillin.

β-Lactam content: 88%.

The penicillin contains 1.5 molar equivalents of $H_2O$ and 0.36 molar equivalent of sodium 2-ethylhexanoate (according to the NMR spectrum). This was taken into consideration in the following calculated analysis figures:

calculated: C, 53.6; H, 5.2; N, 11.8; S, 4.5. found: C, 53.6; H, 5.7; N, 11.7; S, 4.6.

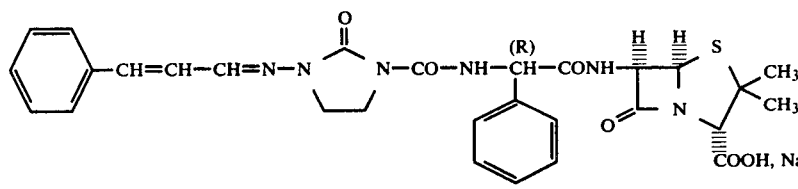

11.3.

This penicillin is prepared from ampicillin trihydrate (2.0 pts. by wt.) and 1-chlorocarbonyl-2-oxo-3-(cinnamylideneamino)-imidazolidine (2.06 pts. by wt.; in excess because of the triethylamine still present in the substance) in the manner described in Example 1.3.

Yield: 2.1 pts. by wt. of sodium D-α-[(2-oxo-3-cinnamylideneamino-imidazolidin-1-yl)-carbonylamino]-benzylpenicillin.

β-Lactam content: 82%.

According to th NMR spectrum, the substance contains about 2.6 molar equivalents of $H_2O$ and 0.56 molar equivalent of sodium 2-ethylhexanoate. This was taken into consideration in the following calculated analysis data:

calculated C, 53.6; H, 5.6; N, 11.2; S, 4.3. found: C, 53.6; H, 5.6; N, 10.8; S, 4.3.

NMR signals at τ=2.3-3.2 (13H), 4.45 (1H), 4.45-4.75 (AB, 2H), 5.9 (1H), 6.1-6.4 (4H), 8.5 (3H) and 8.55 ppm (3H).

IR spectrum (carbonyl range): 1770, 1730, 1670, 1610 and (in liquid paraffin) 1525 cm$^{-1}$ IR spectrum (carbonyl range): 1770, 1740, 1670, 1615 and (in liquid paraffin) 1555-1520 cm$^{-1}$.

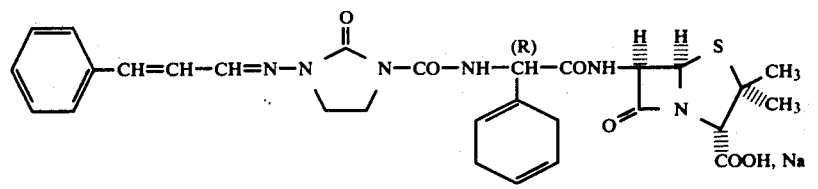

11.5.

This penicillin is prepared from epicillin (1.5 pts. by wt.) and 1-chlorocarbonyl-2-oxo-3-(cinnamylideneamino)-imidazolidine (1.77 pts. by wt.; in excess since it still contained triethylamine hydrochloride) in the manner described in Example 1.3.

Yield: 1.6 pts. by wt. of sodium D-α-[(2-oxo-3-cinnamylideneamino-imidazolidin-1-yl)-carbonylamino]-α-(1,4-cyclohexadien-1-yl)-methylpenicillin.

β-Lactam content: 82%.

According to the NMR, the penicillin contained about 2 molar equivalents of water and 0.36 molar equivalent of sodium 2-ethylhexanoate. This was taken into consideration in the calculated analysis figures:

calculated: C, 54.0; H, 5.6; N, 11.8; S, 4.5. found: C, 54.0; H, 5.7; N, 11.7; S, 4.5.

IR spectrum (carbonyl range): 1772, 1730, 1670, 1610 and (in liquid paraffin) 1530 cm$^{-1}$.

NMR signals at τ=2.25-3.15 (8H), 4.05 (1H), 4.3 (2H), 4.5 (2H), 5.0 (1H), 5.8 (1H), 6.05-6.4 (4H),

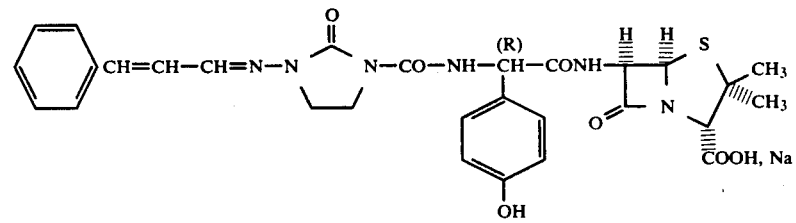

11.4.

This penicillin is prepared from amoxicillin trihydroate (1.5 pts. by wt.) and 1-chlorocarbonyl-2-oxo-3-(cin- 7.15-7.45 (4H), 8.4 (3H) and 8.46 ppm (3H).

11.6.

[Structure: phenyl-CH=CH-CH=N-N(imidazolidinone)-N-CO-NH-CH(phenyl)-CONH-[β-lactam with CH₃-CO-O-CH₂ and S, COOH, Na]]

This cephalosporin is prepared from cephaloglycine dihydrate (1.5 pts. by wt.) and 1-chlorocarbonyl-2-oxo-3-(cinnamylidene-amino)-imidazolidine (1.08 pts. by wt.; in excess since the substance still contains triethylamine hydrochloride) in a manner corresponding to that described for the penicillins in Examples 1.3. and 1.6. In this procedure, after removng the tetrahydrofurane at pH 7.0, a precipitate which is insoluble in water and ethyl acetate is filtered off and is stirred with a mixture of ethyl acetate and water at pH 2.0. After filtering off, the precipitate is stirred with 10 pts. by vol. of dimethylformamide, the undissolved material is filtered off and, after diluting the filtrate with 150 pts. by vol. of ether, the sodium salt is precipitated.

Yield: 0.5 pt. by wt. of sodium 7-{D-α-[(2-oxo-3-cinnamylideneamino-imidazolidin-1-yl)-carbonylamino]-phenylacetamido}-3-acetoxymethyl-ceph-3-em-4-carboxylate.

β-Lactam content: 80%.

According to the NMR, this cephalosporin contains about 3molar equivalents of water and 0.65 molar equivalent of sodium 2-ethylhexanoate. This was taken into consideration in the following calculated analysis values:

calculated: C, 52.3; H, 5.4; N, 10.1; S, 3.9. found: C, 52.4; H, 5.6; N, 10.3; S, 3.8.

IR spectrum (carbonyl range): 1770, 1730, 1668, 1612 and (in liquid paraffin) 1540 cm$^{-1}$.

NMR signals at $\tau$=2.1–2.9 (13H), 3.9–4.3 (2H), 4.75–5.1

(in deuterated DMF) (3H), 4.0 (4H), 6.6 (2H) and 7.9 ppm (3H).

EXAMPLE 12

12.1.

[Structure: pyridin-3-yl-CH=N-N(2-oxo-imidazolidin-1-yl)NH]

Pyridine-3-aldehyde (10.7 pts. by wt.) is added to a solution of 1-amino-2-oxo-imidazolidine (10.1 pts. by wt.) in a mixture of methanol and water (50 pts. by vol. each) and the mixture is then stirred for about 20 hrs. at 20° C. The precipitate which has formed is then filtered off, washed with water and a little methanol and dried at 60° C. over P₄O₁₀ in vacuo.

Yield: 16.5 pts. by wt.
Melting point=195° C. (Kofler stage)
calculated: C, 56.9; H, 5.3; N, 29.5; O, 8.4. found: C, 56.9; H, 5.2; N, 30.0; O, 8.0.

12.2

[Structure: pyridin-3-yl-CH=N-N(2-oxo-imidazolidin-1-yl)N-COCl × HCl]

A solution of phosgene (1.35 pts. by vol.) in tetrahydrofurane (10 pts. by vol.) is added to a suspension of 1-(3-pyridyl-methylideneamio)-2-oxo-imidazolidine (3.0 pts. by wt.) in a mixture of benzonitrile (30 pts. by vol.) and triethylamine (2.6 pts. by vol.), whilst cooling with icewater. After 20 minutes, the mixture is allowed to come to 20° C.and is then stirred at this temperature overnight. The precipitate present is then filtered off, washed with ether and then with dichloromethane and dried.

Yield: 4.2 pts. by wt.
IR spectrum (CO.Cl): 1800 cm$^{-1}$ (in liquid paraffin)
Melting point=252° C. (Kofler stage).

12.3.

[Structure: pyridin-3-yl-CH=N-N(imidazolidinone)-N-CO-NH-CH(phenyl)-CONH-[β-lactam with CH₃, CH₃ (penicillin), COOH, Na]]

This penicillin is prepared from ampicillin trihydrate (1.0 pt. by wt.) and 1-chlorocarbonyl-2-oxo-3-(3-pyridylmethylideneamino)-imidazolidine (0.63 pt. by wt.) in the manner described in Example 1.3. In this procedure, on acidifying the reaction solution, which has been freed from tetrahydrofurane and covered with a layer of ethyl acetate, some of the penicillin is obtained as the free acid (0.20 pt. by wt.; IR spectrum ]carbonyl range]: 1775, 1725, 1670 and 1520 cm$^{-1}$ in liquid paraffin), dissolved in ethyl acetate. The sodium salt is obtained from the organic phase by precipitation with sodium 2-ethylhexanoate solution.

Yield: 0.70 pt. by wt. of sodium-D-α-{[(2-oxo-3-(3-pyridyl-methylideneamino)-imidazolidin-1-yl]-carbonylamino}-benzylpenicillin.

β-Lactam content: 90%.,

According to the NMR spectrum, the penicillin contains about 3.3 molar equivalents of water and 0.13 molar equivalent of sodium 3-ethylhexanoate. This was taken into consideration in the following calcualted analysis data:

calculated: C, 48.6; H, 5.3; N, 14.7; S, 4.8. found: C, 48.5; H, 5.8; N, 14.5; S, 4.8.

IR spectrum (carbonyl range): 1768, 1722, 1667, 1625, 1600
(in liquid paraffin) 1550 and 1525 cm$^{-1}$.

NMR signals at $\tau$=1.0–1.2 (1H), 1.35–1.55 (1H), 1.6–1.85 (1H), 2.15 (1H), 2.3–2.8 (6H), 4.3 (1H), 4.3–4.6 (AB; 2H), 5.8 (1H), 5.9–6.2 (4H), 8.4 (3H) and 8.45 ppm (3H).

Yield: 3.2 pts. by wt. Melting point=209°–210° C. (Kofler stage).
calculated: C, 54.3; H, 4.5; C, 13.4; N, 15.8. found: C, 54.5; H, 4.6;1 Cl, 13.5; N, 15.4.
IR spectrum (CO.Cl): 1810 cm$^{-1}$ (in liquid paraffin).

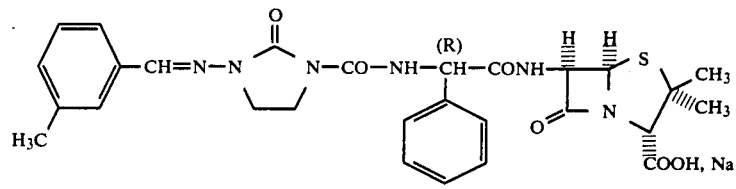

13.3

EXAMPLE 13

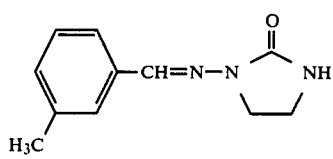

13.1

3-Methylbenzaldehyde is added to a mixture of 1-amino-2-oxo-imidazolidine hydrochloride (14.0 pts. by wt.) and 1 N sodium hydroxide solution (100 pts. by vol.) and the mixture is then subsequently stirred for 5 hrs. at 20° C. The precipitate formed is then filtered off, washed with water and dried.

Yield: 20.3 pts. by wt. Melting point—205°–207° C. (Kofler stage).

This penicillin is obtained when ampicillin trihydrate (2.0 pts. by wt.) and 1- chlorocarbonyl-2-oxo-3-(3-methylbenzylidene-amino)-imidazolidine (1.6 pts. by wt.) are reacted in the manner described in Example 1.3.

Yield: 2.55 pts. by wt. of sodium D-α-{[(2-oxo-3-(3-methylbenzylidene-amino)-imidazolidin-1-yl]-carbonylamino}-benzylpenicillin.

β-Lactam content: 980%.

According to the NMR spectrum, the penicillling contains some sodium 2-ethylhexanoate (about 0.06 molar equivalent) and water (3 molar equivalents). This was taken into consideration in the calculated analysis data:

calculated: C, 52.1; H, 5.41; N, 12.6; S, 4.8. found: C, 51.9; H, 6.3; N, 12.4; S, 4.9.

IR spectrum (carbonyl range): 1770, 1730, 1675, 1612 and (in liquid paraffin) 1530 cm$^{-1}$.

NMR signals at $\tau$=2.25–2.9 (10H), 4.35 (1H), 4.35–4.65 (AB, (CD$_3$OD) 2H), 5.85 (1H), 6.1–6.4 (4H), 7.7 (3H), 8.4 (3H) and 8.5 ppm (3H).

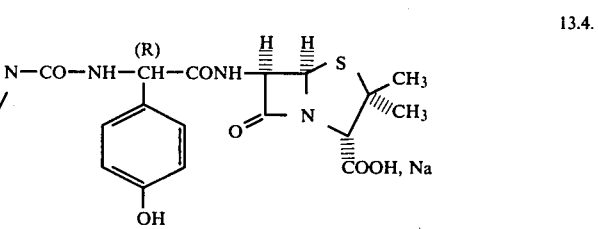

13.4.

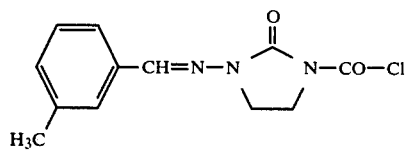

13.2

A solution of trimethylchlorosilane )9.65 pts. by wt.) in benzene (50 pts. by vol.) is added dropwise to a weakly boiling mixture of 1-(3-methyl-benzylidene-amino)-2-oxo-imidazolidine (12.1 pts. by wt.), benzene (150 pts. by vol.) and triethylamine (13.4 pts. by vol.) in the course of one hour. The mixture is then boiled under reflux for 20 hrs. and the triethylamine hydrochloride is filtered off hot and rinsed with hot benzene. A solution of phosgene (4.7 pts. by vol.) in benzene (30 pts. by vol.) is added to the combined filtrates, which have been cooled to 10° C., and the mixture is then left to stand at 20° C. for 48 hrs. The precipitate which has formed is then filtered off, washed with benzene, subsequently triturated with dichloromethane (40 pts. by vol.) and then dried.

This penicillin is obtained when amoxicillin trihydrate (1.0 pt. by wt.) and 1-chlorocarbonyl-2-oxo-3-(3-methylbenzyliene-amino)-imidazolidine (0.73 pt. by wt.) are reacted with one another according to Example 1.3.

Yield: 1.1 pts. by wt. of crystalline sodium D-α-α-{[(2-oxo-3-(3-methylbenzylidene-amino)-imidazolidin-1-yl]-carbonylamino}-p-hydroxybenzylpenicillin.

β-Lactam content: 90%.

According to the NMR spectrum, the penicillin contains some sodium 2-ethylhxanoate (0.16 molar equivalent) and water (2.9 molar equivalents). This was taken into consideration in the following calculated analysis data:

calculated: C, 50.5; H, 5.3; N, 12.1; S, 4.6. found: C, 50.5; H, 5.4; N, 11.9; S, 4.6.

IR spectrum (carbonyl range): 1790, 1765, 1720, 1690, 1660, (in liquid paraffin) 1612, 1590, 1550 and 1510 cm$^{-1}$.

NMR signals at $\tau$=2.2–3.3 (9H), 4.4–4.65 (3H), 5.85 (1H), (in CD$_3$OD) 6.0–6.3 (4H), 7.65 (3H),8.4 (3H) and 8.5 ppm (3H).

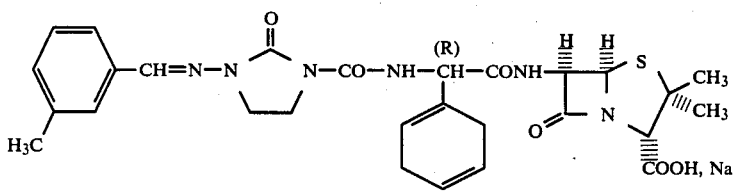

This penicillin is obtained when epicillin (1.0 pt. by wt.) is reacted with 1-chlorocarbonyl-2-oxo-3-(3-methylbenzylidene-amino)-imidazolidine (0.91 pt. by wt.) in the manner described in Example 1.3. During the precipitation of the sodium salt, 0.8 pt. by wt. of the amorphous penicillin was first obtained, and 0.9 pt. by wt. of crystalline sodium D-α-{[(2-oxo-3-(3-methyl-benzylidene-amino)-imidazolidin-1-yl]-carbonylamino}-α-(1,4-cyclohexadien-1-yl)-methyl-penicillin was obtained by further precipitation from its mother liquor.

IR spectrum of the amorphous salt (carbonyl range): 1770,
(in liquid paraffin) 1730, 1670, 1610 and 1525 cm$^{-1}$.
IR spectrum of the crystalline salt (carbonyl range): 1790, (in liquid paraffin (1775), 1740, 1712, 1660, 1600, 1575 and 1520 cm$^{-1}$.

NMR signals at $\tau32$ 2.1–2.8 (5H), 4.05 (1H), 4.3 (2H), 4.5 (2H), (in CD$_3$OD) 5.0 (1H), 5.8 (1H), 6.1 (4H), 7.25 (4H), 7.65 (3H), 8.35 (3H) and 8.45 ppm (3H).

NMR signals at $\tau=1.85$–2.8 (10H), 3.9–4.3 (2H), 4.7–5.0 (3H), (in d$_7$-DMF) 5.8–6.1 (4H), 6.4–6.7 (2H), 7.5 (3H) and 7.8 ppm (3H).

EXAMPLE 14

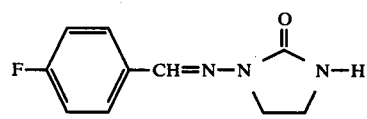
14.1.

This substance is obtained from 1-amino-2-oxo-imidazolidine hydrochloride (14.0 pts. by wt.) and 4-fluorobenzaldehyde (12.8 pts. by wt.) in the manner described in Example 13.1.

Yield: 20.4 pts. by wt. Melting point=229°–230° C. (Kofler stage).

14.2.

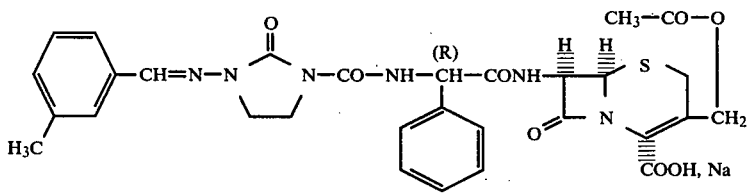
13.6.

This cephalosoprin is obtained when cephaloglycine dihydrate (1.0 pt. by wt.) is reacted with 1-chlorocarbonyl-2-oxo-3-(3-methylbenzylideneamino)-imidazolidine (0.69 pt. by wt.) in the manner described for the penicillins in Examples 1.3. and 1.6. The sodium salt separated out as a gel-like precipitate which could not be filtered off. All the volatile constituents were therefore stripped off and the residue was treated with dry ether. The cephalosporin salt was thereby obtained as a loose white powder.

Yield: 1.2 pts. by wt. of sodium 7-{D-α-[(2-oxo-3{3-methylbenzylideneamino}-imidazolidin-1-yl)-carbonylamino]-phenylacetamido}-3-acetoxymethyl-ceph-3-em-4-carboxylate.

β-Lactam content: 90%.

The cephalosporin salt contains about 2.9 molar equivalents of water. This was taken into consideration in the calculated analysis data:
calculated: C, 51.2; H, 4.9; N, 11.9; S, 4.6. found: C, 51.4; H, 5.5; N, 11.7; S, 4.7.

IR spectrum (carbonyl range): 1765 (shoulder), 1740, 1660, (in liquid paraffin) 1610 and 1535 cm$^{-1}$.

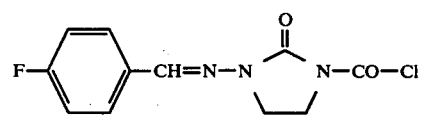

A solution of phosgene (4.2 pts. by vol.) in benzonitrile (10 pts. by vol.) is added dropwise to a mixture of 1-(4-fluorobenzylidene-amino)-2-oxo-imidazolidine (6.0 pts. by wt.), benzonitrile (50 pts. by vol.) and triethylamine (8 pts. by vol.), whilst cooling with ice/water and stirring, and the mixture is then subsequently stirred for a further 3 hrs. at 20° C. The precipitate is then filtered off, suspended in dichloromethane (240 pts. by vol.), filtered off again and dried.

Yield: 0.9 pt. by wt. (still more of this substance is in the mother liquor).

The substance is not completely free from triethylamine hydrochloride, which, however, was not troublesome in the further reaction.

IR spectrum (CO.Cl): 1820/1810 cm$^{-1}$ (in liquid paraffin)

Melting point=240°–247° C. decomp. (Kofler stage).

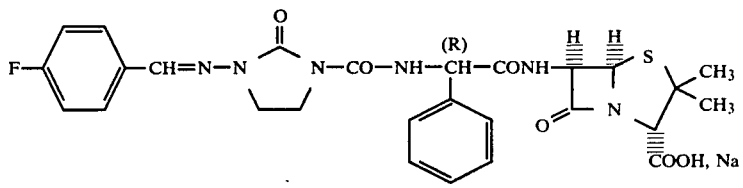

14.3.

This penicillin is obtained when ampicillin trihydrate (1.0 pt. by wt.) and 1-chlorocarbonyl-2-oxo-3-(4-fluorobenzylidene-amino)-imidazolidine (0.8 pt. by wt.) are reacted with one another in the manner described in Example 1.3.

Yield: 1.2 pts. by wt. of crystalline sodium D-α-{[(2-oxo-3-(4-fluorobenzylidene-amino)-imidazolidin-1-yl]-carbonylamino}-benzylpenicillin.

β-Lactam content: 93%.

According to the NMR spectrum, the penicillin contains about 1.7 molar equivalents of water. This was taken into consideration in the calculated analysis values:

calculated: C, 51.1; H, 4.6; N, 13.2; S, 5.0. found: C, 51.1; H, 5.4; N, 13.2; S, 5.1.

IR spectrum (carbonyl range): 1790, (1767), 1730, 1702, 1670 (in liquid paraffin) (shoulder), 1660 and 1602 cm⁻¹.

NMR signals at τ=2.1–3.1 (10H), 4.4 (1H), 4.4–4.65 (AB, 2H), (in CD₃OD) 5.85 (1H), 6.0–6.3 (4H), 8.45 (3H) and 8.55 ppm (3H).

IR spectrum (carbonyl range): 1775 (shoulder), 1760 (shoulder), (in liquid paraffin) 1735, 1680, 1610 and 1550–1520 cm⁻¹.

NMR signals at τ=2.1–2.9 (10), 4.2–4.35 (1H), 4.4 (1H), (in CD₃OD) 5.0–5.2 (3H), 6.1 (4H), 6.5–6.7 (2H) and 8.0 ppm (3H).

EXAMPLE 15

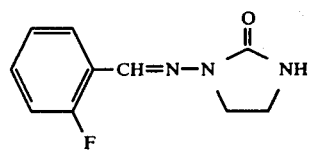

15.1.

This substance is obtained from 1-amino-2-oxo-imidazolidine hydrochloride (14.0 pts. by wt.) and 2-fluorobenzaldehyde (12.7 pts. by wt.), as in Example 13.1., in a yield of 17.6 pts. by wt.

Melting point 214°–216° C. (Kofler stage).

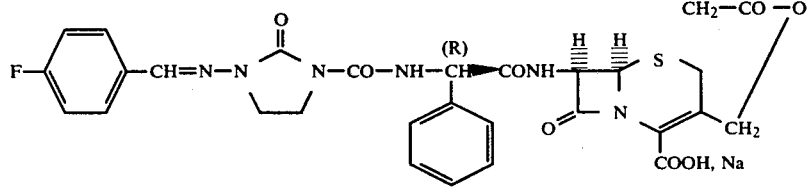

14.4.

This cephalosporin is obtained when cephloglycine dyhydrate (1.0 pt. by wt.) is reacted with 1-chlorocarbonyl-2-oxo-3-(4-fluorobenzylidene-amino)-imidazolidine (0.7 pt. by wt.) in the manner described for the penicillins in Examples 1.3. and 1.6. Since the sodium salt separated out as a gel and was difficult to filter off in this form, all the volatile constituents were removed in vacuo and the residue was treated with a mixture of ether/methanol (10/1).

During this procedure, the sodium salt was converted into a loose, white powder.

Yield: 0.5 pt. by wt. of sodium 7-{D-α-[(2-oxo-3-p-fluorobenzylideneamino-imidazolidin-1-yl)-carbonylamino]-phenylacetamido}-3-acetoxymethyl-ceph-3-em-4-carboxylate.

β-Lactam content: 91%.

According to the NMR spectrum, the cephalosporin contains about 0.13 molar equivalent of sodium 2-ethyl-hexanoate and 1.7 molar equivalents of water. This was taken into consideration in the calculated analysis data:

calculated: C, 50.7; H, 4.4; N, 11.8; S, 4.5. found: C, 50.7; H, 4.4; N, 11.8; S, 4.6.

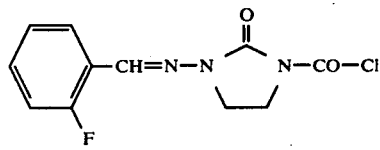

15.2.

A solution of phosgene (4.2 pts. by vol.) in benzonitrile (10 pts. by vol.) is added dropwise to a mixture of b  1-(2-fluorobenzylidene-amino)-2-oxo-imidazolidine (6.0 pts. by wt.), benzonitrile (50 pts. by vol.) and triethylamine (8 pts. by vol.), whilst stirring and cooling with ice/water. The mixture is subsequently stirred for a further 3 hrs. at 20° C. The precipitate is then filtered off, washed with ether, suspended in about 120 pts. by vol. of dichloromethane, filtered off again and dried.

Yield: 5.6 pts. by wt.

Melting point=230° C. (Kofler stage)

IR spectrum (CO.Cl): 1800 (with shoulder at about 1815) cm⁻¹.

The substance contains some triethylamine hydrochloride, which, however, was not troublesome in the further reaction.

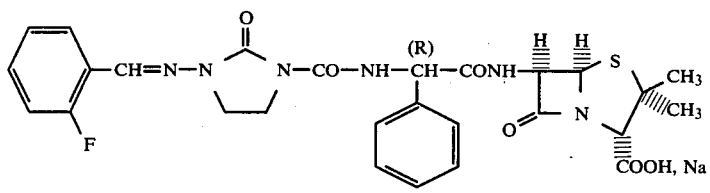

15.3.

This penicillin is obtained from ampicillin trihydrate (1.0 pt. by wt.) and 1-chlorocarbonyl-2-oxo-3-(2-fluorobenzylidene-amino)-imidazolidine (0.8 pt. by wt.) when they are reacted with one another using the procedure described in Example 1.3.

Yield: 0.55 pt. by wt. of crystalline sodium D-α- {[2-oxo-3-(2-fluorobenzylidene-amino)-imidazolidin-1-yl]-carbonylamino}-benzylpenicillin.

β-Lactam content: 90%.

According to the NMR spectrum, the penicillin contains about 2.9 molar equivalents of water. This was taken into consideration in the following calculated analysis figures:

calculated: C, 49.4; H, 4.9; N, 12.8; S, 4.9. found: C, 49.4; H, 4.9; N, 12.6; S, 5.3.

IR spectrum (carbonyl range): 1793, (1775), 1740, (1700 and (in liquid paraffin) 1680, both shoulders), 1660, 1610, 1560 and 1520 cm$^{-1}$.

NMR signals at $\tau = 1.8$–3.1 (10), 4.4 (1H), 4.4–4.65 (2H), 5.8 (in CD$_3$OD) (1H), 6.0–6.3 (4H), 8.45 (3H) and 8.55 ppm (3H).

calculated: C, 49.2; H, 4.5; N, 11.7; S, 4.5. found: C, 49.1; H, 4.3; N, 11.7; S, 4.9.

IR spectrum (carbonyl range): 1780, 1730, 1670, 1610 and (in liquid paraffin) 1530 cm$^{-1}$.

NMR signals at $\tau = 1.8$–2.9 (10H), 4.0–4.4 (2H), 4.8–5.1 (3H), (in d$_7$-DMF) 5.8–6.2 (4H), 6.5–6.75 (2H) and 7.95 ppm (3H).

EXAMPLE 16

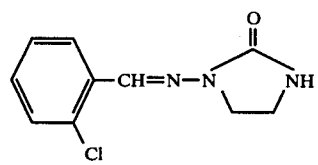

16.1.

47.5 pts. by wt. of 2-oxo-imidazolidine, 38.0 pts. by wt. of sodium nitrite and 82.5 pts. by wt. of zinc dust are processed as in Example 2.1. and the mixture is reacted with 64.0 pts. by wt. of 2-chlorobenzaldehyde. This

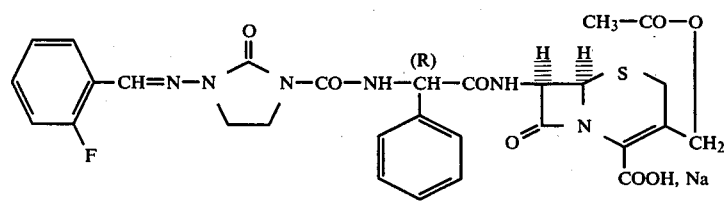

15.4.

This cephalosporin is obtained from cephaloglycine dihydrate (1.5 pts. by wt.) and 1-chlorocarbonyl-2-oxo-3-(2-fluorobenzylidene-amino)-imidazolidine (1.07 pts. by wt.) according to the preparation process described for the penicillins in Examples 1.3. and 1.6. During the working up, on acidifying the mixture to pH 2, some of the cephalosporin is obtained as the free acid (0.2 pt. by wt.; IR spectrum [carbonyl range]: 1780, 1745, 1670 and 1540 cm$^{-1}$ in liquid paraffin), which is insoluble in water and ethyl acetate. If the cephalosporin formed is dissolved in the organic phase, it is obtained from this in a yield of 0.8 pt. by wt. as sodium 7-{D-α-[(2-oxo-3-{2-fluorobenzylidene-amino}-imidazolidin-1-yl)-carbonyl-amino]-phenylacetamido}-3-acetoxymethyl-ceph-3-em-4-carboxylate.

The following data relate to the sodium salt.

β-Lactam content: 91%.

According to the NMR spectrum, the cephalosporin contains about 2.8 molar equivalents of water and 0.05 molar equivalent of sodium 2-ethylhexanoate. This was taken into consideration in the calculated analysis data:

gives 65.0 pts. by wt. of 1-(2-chloro)-benzoalimino-2-oxo-imidazolidine, which is recrystallised from ethanol. Melting point 216°–17° C.

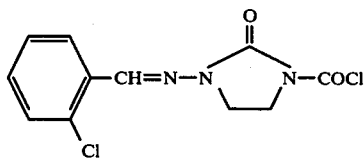

16.2.

50.0 pts. by wt. of 1-(2-chloro)-benzalimino-2-oxo-imidazolidine and 73.0 pts. by wt. of triethylamine in 400 pts. by vol. of abs. dioxane as well as 72.7 pts. by wt. of trimethylchlorosilane in 150 pts. by vol. of abs. dioxane and 44.5 pts. by wt. of phosgene are reacted as in Example 2.2. This gives 37.2 pts. by wt. of 1-chlorocarbonyl-2-oxo-3-(2-chloro)-benzalimino-imidazolidine, which is recrystallised from acetonitrile. Melting point 233°–7° C.

IR (liquid paraffin): 1800 cm$^{-1}$.

calculated: C, 46.18; H, 3.17; N, 14.68; Cl, 24.78. found: C, 46.1; H, 3.2; N, 14.6; Cl, 24.7.

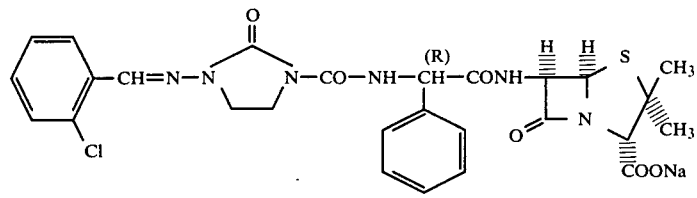

16.3.

14.1 pts. by wt. of ampicillin trihydrate in 150 pts. by vol. of 80 percent strength aqueous THF are reacted with 5.0 pts. by wt. of 1-chlorocarbonyl-2-oxo-3-(2-chloro)-benzalimino-imidazolidine as in Example 1.3. This gives 11.3 pts. by wt. of sodium 6-{D-α-[(2-oxo-3-{2-chloro}-benzalimino-imidazolidin-1-yl)-carbonylamino]-phenylacetamido}-penicillanate of decomp. pt. 215°–220° C.

β-Lactam content: 83%.

IR (KBr): 1765, 1730, 1675 and 1605 cm$^{-1}$.

NMR (CD$_3$OD): 7.92 (s with overlaid m, 2H), m centred at 7.3

(8H), 5.55 (s, 1H), 5.42 (AB system, 2H), 4.12 (s, 1H), 3.83 (s, broad, 4H), 1.58 (s, 3H) and 1.50 (s, 3H) δ.

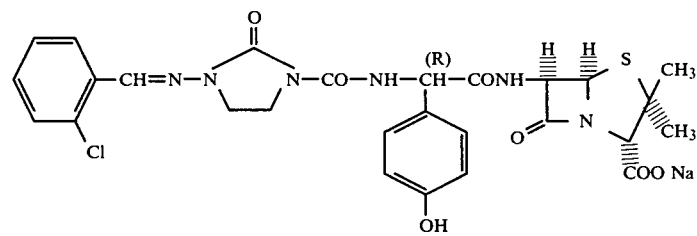

16.4.

6.3 pts. by wt. of amoxicillin trihydrate in 80 pts. by vol. of 80 percent strength aqueous THF are reacted with 2.9 pts. by wt. 1-chlorocarbonyl-2-oxo-3-(2-chloro)-benzalmino-imidazolidine as in Example 1.4.

This gives 8.5 pts. by wt. of sodium 6-{D-α-[(2-oxo-3-{2-chloro}-benzalimino-imidazolidin-1-yl)-carbonylamino]-4-hydroxyphenylacetamido}-penicillanate.

IR (KBr): 1760, 1720, 1655 and 1600 cm$^{-1}$.

NMR (CD$_3$OD): 7.95 s (1H), 7.5–6.8 (8H), 5.5 (m, 3H), 4.20 (s, 1H), 3.92 (s, broad, 4H), 1.60 (s, 3H) and 1.50 (s, 3H) δ.

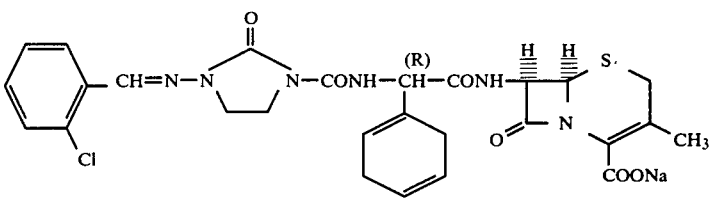

16.5.

10.5 pts. by wt. of cephradin in 100 pts. by vol. of 80 percent strength aqueous THF are reacted with 5.7 pts. by wt. of 1-chlorocarbonyl-2-oxo-3-(2-chloro)-benzalimino-imidazolidine as in Example 1.3. This gives 10.9 pts. by wt. of sodium 7-{D-α-[(2-oxo-3-{2-chloro}-benzalimino-imidazolidin-1-yl)-carbonylamino]-cyclohex-1,4-dien-1-yl-acetamido}-3-methyl-ceph-3-em-4-carboxylate of decomp. pt. 222° C.

IR (KBr): 1770, 1735, 1665 and 1590 cm$^{-1}$.

C$_{27}$H$_{26}$ClN$_6$NaO$_6$S.2H$_2$O: calculated: C, 49.36; H, 4.66; N, 12.79; S, 4.88; Cl, 5.39. found: C, 48.9; H, 4.5; N, 12.4; S, 4.4; Cl, 5.3.

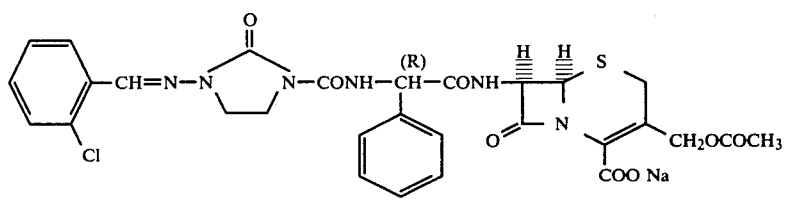

16.6.

C$_{27}$H$_{26}$ClN$_6$NaO$_6$S.2H$_2$O calculated: C, 49.36; H, 4.60; N, 12.79. found: C, 49.4; H, 4.6; N, 12.7.

5.0 pts. by wt. of cephaloglycine dihydrate in 100 pts. by vol. of 80 percent strength aqueous THF are reacted with 3.3 pts. by wt. of 1-chlorocarbonyl-2-oxo-3-(2-chloro)-benzalimino-imidazolidine as in Example 1.6. This gives 6.7 pts. by wt. of sodium 7-{D-α-[(2-oxo-3-{2-chloro}-benzalimino-imidazolidin-1-yl)-carbonylamino]-phenylacetamido}-3-acetoxy-methyl-ceph-3-em-4-carboxylate of decomp. pt. of 195°–200° C.

IR (KBr): 1760, 1725, 1670 and 1600 cm$^{-1}$.

NMR (CD$_3$OD/D$_2$O): 7.2–8.0 (aromatic protons and —CH=N—), 5.65 (d, 1H), 5.50 (s, 1H), 5.05 (d, overlaid by the signal of the replaceable protons), 3.8 (6H) and 2.10 (s, 3H) δ.

C29H26ClN6NaO8S.H2O: calculated: C, 50.11; H, 4.21; N, 12.09; S, 4.63. found; C, 50.1; H, 4.1; N, 12.1; S, 4.8.

with 8.7 pts. by wt. of 1-chlorocarbonyl-2-oxo-3-(3-chloro)-benzalimino-imidazolidine as in Example 1.3. This gives 5.0 pts. by wt. of sodium 6-{D-α-[(2-oxo-3-{3-chloro}-benzalimino-imidazolidin-1-yl)-carbonylamino]-phenylacetamido}-penicillanate.

IR(KBr): 1760, 1720, 1660 and 1600 cm⁻¹.

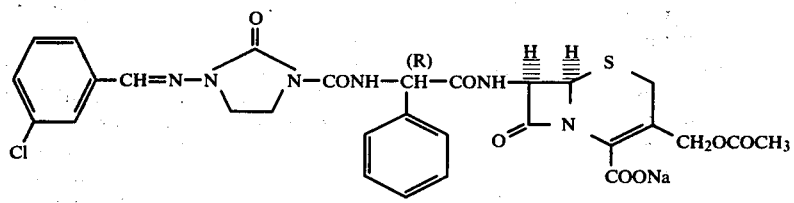

17.4.

EXAMPLE 17

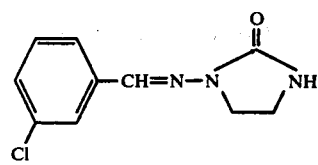

17.1.

47.6 pts. by wt. of 2-oxo-imidazolidine, 34.5 pts. by wt. of sodium nitrite and 78.4 pts. by wt. of zinc dust are processed as in Example 1.1. and the mixture is stirred overnight with 77.0 pts. by wt. of 3-chlorobenzaldehyde. This gives 65.7 pts. by wt. of 1-(3-chloro)-benzalimino-2-oxo-imidazolidine of melting point 210°–212° C.

IR (KBr): 3230, 3120, 1715, 1475 and 1405 cm⁻¹.

NMR (d6-DMSO): m, centred at 7.5 (aromatic protons, —CH═N—and NH: 6H), and 3.65 (m, 4H) δ.

calculated: C, 53.70; H, 4.51; N, 18.79; Cl, 15.85. found: C, 54.0; H, 4.7; N, 18.4; Cl, 16.2.

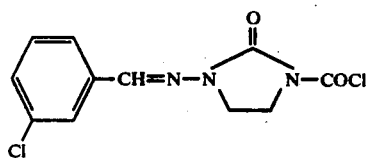

17.2.

A solution of 43.3 pts. by wt. of trimethylchlorosilane in 80 pts. by vol. of abs. dioxane is added dropwise to a boiling solution of 30.0 pts. by wt. of 1-(3-chloro)-benzalimino-2-oxo-imidazolidine and 43.4 pts. by wt. of triethylamine in 250 pts. by vol. of abs. dioxane and the mixture is reacted with 26.4 pts. by wt. of phosgene as in Example 2.2. This gives 16.2 pts. by wt. of 1-chlorocarbonyl-2-oxo-3-(3-chloro)-benzaliminoimidazolodine of decomp. pt. 190° C., which still contains a small amount of starting material.

IR (liquid paraffin): 1800 cm⁻¹.

3.3 pts. by wt. of cephaloglycine dihydrate in 100 pts. by vol. of 80 percent strength aqueous THF are reacted with 2.5 pts. by wt. of 1-chlorocarbonyl-2-oxo-3(3-chloro)-benzalimino-imidazolidine as in Example 1.6. This gives 2.1. pts. by wt. of sodium 7-{D-α-[(2-oxo-3-{3-chloro}-benzalimino-imidazolidin-1-yl)-carbonylamino]-phenylacetamido}-3-acetoxy-methyl-ceph-3-em-4-carboxylate of melting point 212°–218° C. (decomp.).

IR (KBr): 1765, 1735, 1665 and 1610 cm⁻¹.

C29H26ClN6NaO8S.3H2O: calculated: C, 47.65; H, 4.42; N, 11.49. found: C, 47.6; H, 4.8; N, 11.5.

EXAMPLE 18

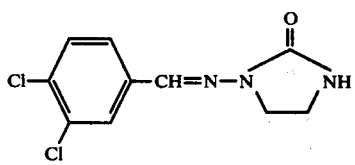

18.1.

47.6 pts. by wt. of 2-oxo-imidazolidine, 34.5 pts. by wt. of sodium nitrite and 78.4 pts. by wt. of zinc dust as well as 87.5 pts. by wt. of 3,4-dichlorobenzaldehyde are reacted as in Example 1.1. This gives 50.4 pts. by wt. of 1-(3,4-dichloro)-benzalimino-2-oxo-imidazolidine of melting point 178°–181° C.

IR (KBr): 3240, 1710 (broad), 1470, 1400 and 1260 cm⁻¹.

NMR (d6-DMSO): 7.95 (s, 1H), 7.7 (m, 3H), 7.37 (s, broad, 1H), and m centred at 3.7 (4H).

calculated: C, 46.46; H, 3.52; N, 16.28; Cl, 27.47. found: C, 46.4; H, 3.6; N, 16.1; Cl, 27.4.

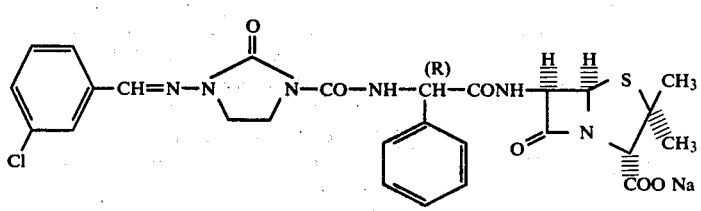

17.3.

9.3 pts. by wt. of ampicillin trihydrate in 100 pts. by vol. of 80 percent strength aqueous THF are reacted 18.2.

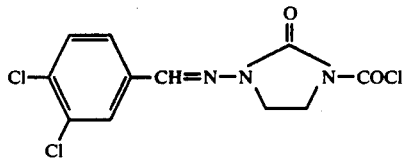

30.0 pts. by wt. of 1-(3,4-dichloro)-benzalimino-2-oxo-imidazolidine and 37.8 pts. of wt. of triethylamine in 250 pts. by vol. of abs. dioxane as well as 37.7 pts. by wt. of trimethylchlorosilane in 80 pts. by vol. of abs. dioxane and 23.1 pts. by wt. of phosgene are reacted as in Example 2.2. This gives 11.2 pts. by wt. of 1-chlorocarbonyl-2-oxo-3-(3,4-dichloro)-benzalimino-imidazoolidine of decomp. pt. 224°–230° C.

IR (liquid paraffin): 1800 cm$^{-1}$.

calculated: C, 41.80; H, 2.82; N, 13.07; Cl, 33.07. found: C, 41.9; H, 2.8; N, 12.9; Cl, 32.8.

18.3.

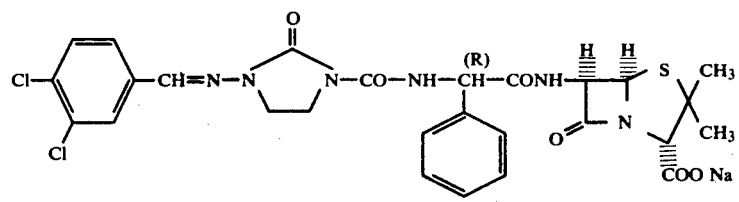

9.4 pts. by wt. of ampicillin trihydrate in 100 pts. by vol. of 80 percent strength aqueous THF are reacted with 5.0 pts. by wt. of 1-chlorocarbonyl-2-oxo-3-(3,4-dichloro)-benzalimino-imidazolidine as in Example 1.3. This gives 5.3 pts. by wt. of sodium 6-{D-α-[(2-oxo-3-{3,4-dichloro}-benzalimino-imidazolidin-1-yl)-carbonylamino]-phenylacetamido}-penicillanate.

IR (KBr): 1765, 1725, 1660 and 1605 cm$^{-1}$.

NMR (CD$_3$OD): 7.3–7.7 (aromatic protons and —CH=N—), 5.61 (s, 1H), 5.50 (q, 2H), 4.18 (s, 1H), 3.85 (s, broad, 4H), 1.58 (s, 3H) and 1.50 (s, 3H) δ.

18.4.

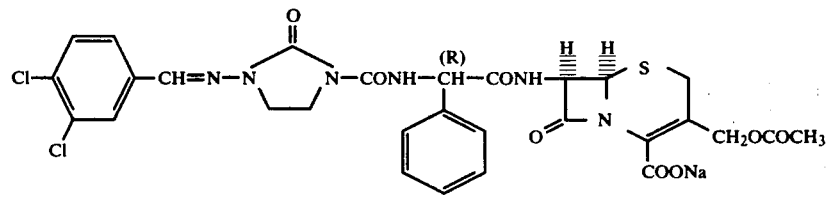

7.0 pts. by wt. of cephaloglycine dihydrate in 100 pts. by vol. of 80 percent strength aqueous THF are reacted with 5.0 pts. by wt. of 1-chlorocarbonyl-2-oxo-3-(3,4-dichloro)-benzalimino-imidazolidine as in Example 1.6. This gives 7.7 pts. by wt. of sodium 7-{D-α-[(2-oxo-3-{3,4-dichloro}-benzalimino-imidazolidin-1-yl)-carbonylamino]-phenylacetamido}-3-acetoxymethyl-ceph-3-em-4-carboxylate of decomp. pt. 190°–5° C.

IR (KBr): 1765, 1740, 1665 and 1615 cm$^{-1}$.

calculated: C, 48.95; N, 11.80; O, 17.99. found: C, 49,0; N, 11.7; O, 18.1.

EXAMPLE 19

19.1.

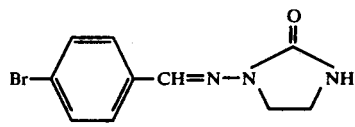

27.8 pts. by wt. of 2-oxo-imidazolidine, 20.0 pts. by wt. of sodium nitrite and 38.0 pts. by wt. of zinc dust as well as 54.0 pts. by wt. of 4-bromobenzaldehyde are reacted as in Example 1.1. This gives 22.4 pts. by wt. of 1-(4-bromo)-benzalimino-2-oxo-imidazolidine of melting point 250°–2° C.

IR (KBr): 3240, 3120, 1740, 1705, 1595, 1475, 1415 and 1270 cm$^{-1}$.

NMR (d$_6$DMSO): 7.67 (aromatic protons and —CH=N—), 7.30 (s, broad, 1H), and m, centred at 3.6 (4H), δ.

calculated: C, 44.80; H, 3.76; N, 15.67. found: C, 44.9; H, 3.7; N, 15.3.

19.2.

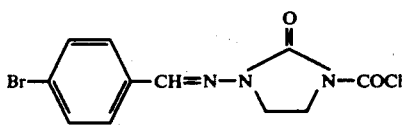

21.7 pts. by wt. of 1-(4-bromo-(benzalimino-2-oxo-imidazolidine and 26.3 pts. by wt. of triethylamine in 250 pts. by vol. of abs. dioxane as well as 26.2 pts. by wt. of chlorotrimethylsilane in 80 pts. by vol. of abs. dioxane and 16.0 pts. by wt. of phosgene are reacted as in Example 2.2.

This gives 4.2 pts. by wt. of 1-chlorocarbonyl-2-oxo-3-(4-bromo)-benzalimino-imidazolidine of melting point 177°–180° C.

IR (liquid paraffin): 1800 cm$^{-1}$.

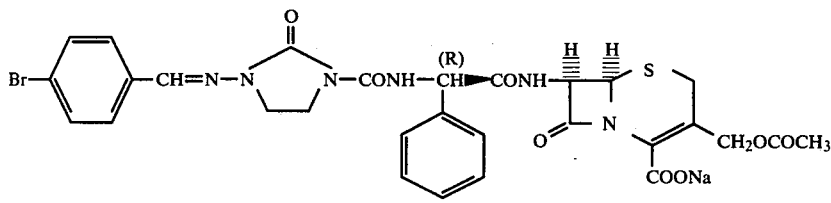

19.3.

5.7 pts. by wt. of cephaloglycine dihydrate and 4.2 pts. by wt. of 1-chlorocarbonyl-2-oxo-3-(4-bromo)-benzalimino-imidazolidine are reacted as in Example 18.3 This gives 3.5 pts. by wt. of sodium 7-{D-α[(2-oxo-3-{4-bromo}-benzalimino-imidazolidin-1-yl)-carbonylamino]-phenylacetamido}-3-acetoxymethyl-ceph-3-em-4-carboxylate of decomp. pt. 190°-3° C.

IR (KBr): 1760, 1725, 1655 and 1600 cm$^{-1}$.

20.3 pts. by wt. of 1-(4-methyl)-benzalimino-2-oxo-imidazolidine, 33.3 pts. by wt. of triethylamine, 32.1 pts. by wt. of chlorotrimethylsilane and 19.8 pts. by wt. of phosgene are reacted as in Example 19.2. This gives 19.6 pts. by wt. of 1-chlorocarbonyl-2-oxo-3-(4-methyl)-benzalimino-imidazolidine of melting point 265°-8° C.

IR (liquid paraffin): 1800 cm$^{-1}$.

calculated: C, 54.24; H, 4.55; N, 15.82; Cl, 13.34. found: C, 54.2. H, 4.5; N, 15.8; Cl, 13.6.

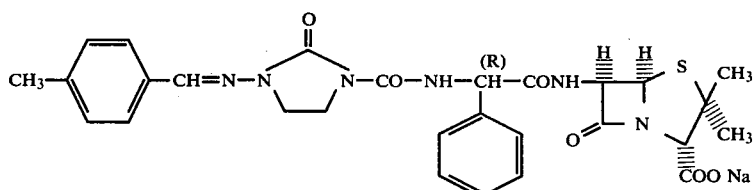

20.3.

EXAMPLE 20

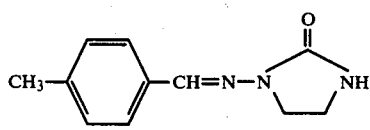

20.1.

47.6 pts. by wt. of 2-oxo-imidazolidine, 34.5 pts. by wt. of sodium nitrite and 78.4 pts. by wt. of zinc dust as well as 60.1 pts. by wt. of 4-methylbenzaldehyde are reacted as in Example 1.1. This gives 52.2 pts. by wt. of 1-(4-methyl)-benzalimino-2-oxo-imidazolidine of melting point 235°-6° C.

8.1 pts. by wt. of ampicillin trihydrate and 2.7 pts. by wt. of 1-chlorocarbonyl-2-oxo-3-(4-methyl)-benzalimino-imidazolidine are reacted as in Example 2.3. This gives 5.0 pts. by wt. of sodium 6-{D-α-[(2-oxo-3-{4-chloro}-benzalimino-imidazolidin-1-yl)-carbonylamino]-phenylacetamido}-penicillanate of decomp. at 220°-225° C.

IR (KBr): 1760, 1725, 1660 and 1600 cm$^{-1}$.

NMR (CD$_3$OD): 7.1-7.8 (aromatic protons and —CH=N—), 5.60 (s, 1H), 2.18 (s, 3H), 1.58 (s, 3H) and 1.50 (s, 3H) δ.

C$_{28}$H$_{29}$N$_6$NaO$_6$S.2H$_2$O: calculated: C, 52.82; H, 5.22; N, 13.20; S, 5.03. found: C, 52.6; H, 5.3; N, 12.8; S, 5.2.

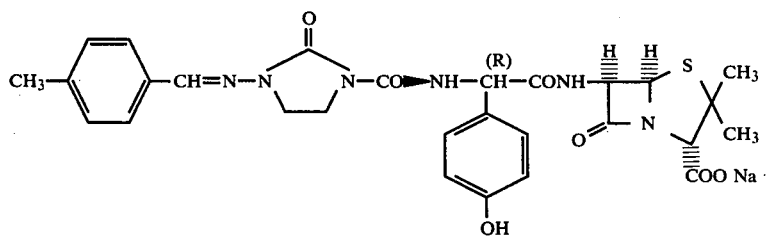

20.4.

IR (KBr): 3230, 3110, 1710 (broad), 1475, 1410 and 1270 (broad) cm$^{-1}$.

NMR (d$_6$-DMSO): 7.2-7.8 (aromatic protons, —CH=N— and NH; 6H), m, centred at 3.7 (4H) and 2.40 (s, 3H) δ.

calculated: C, 65.00; H, 6.45; N, 20.68. found: C, 65,0; H, 6.3; N, 20.8.

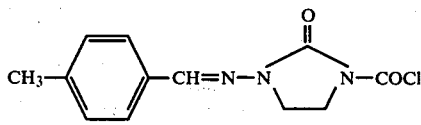

20.2.

5.0 pts. by wt. of amoxicillin trihydrate and 3.2 pts. by wt. of 1-chlorocarbonyl-2-oxo-3-(41 -methyl)-benzalimino-imidazolidine are reacted as in Example 10.5. This gives 6.8 pts. by wt. of sodium 6-{D-α-[(2-oxo-3-{4-methyl}-benzalimino-imidazolidin-1-yl)-carbonylamino]-4-hydroxyphenylacetamido}-penicillinate of decomp. pt. 230°-5° C.

IR (KBr): 1765, 1730, 1665 and 1610 cm$^{-1}$.

NMR (CD$_3$OD): 7.6-6.7 (aromatic protons and —CH=N—), 5.5 (m, 3H), 4.18 (s, 1H), 3.6 (m, 4H), 3.25 (s, 3H), 1.55 (s, 3H) and 1.50 (s, 3H) δ.

C$_{28}$H$_{29}$N$_6$NaO$_7$S.2H$_2$O: calculated: C, 51.53; H, 5.09; N, 12.87; S, 4.91. found: C, 51.2; H, 5.2; N, 12.7; S, 5.1.

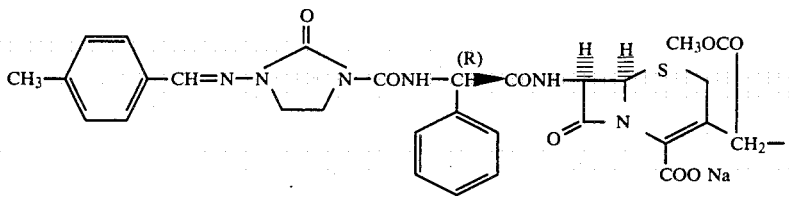

20.5.

5.0 pts. by wt. of cephaloglycine dihydrate in 50 pts. by vol. of 80 percent strength aqueous THF are reacted with 3.0 pts. by wt. of 1-chlorocarbonyl-2-oxo-3-(4-methyl)-benzalimino-imidazolidine as in Example 1.6. This gives 5.5 pts. by wt. of sodium 7-{D-α-[(2-oxo-3-{-b 4-methyl}-benzalimino-imidazolidin-1-yl)-carbonylamino]-phenylacetamido}-3-acetoxymethyl-ceph-3-em-4-carboxylate of decomp. pt. 178°–80° C.

IR (KBr): 1760, 1725, 1660 and 1615 cm$^{-1}$.

$C_{30}H_{29}N_6NaO_8S\cdot H_2O$: calculated: C, 53.41; N, 12.47. found: C, 53.4; N, 12.5.

EXAMPLE 21

21.1.

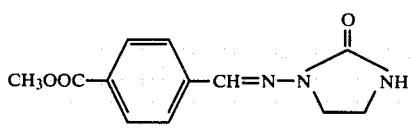

47.6 pts. by wt. of 2-oxo-imidazolidone, 34.5 pts. by wt. of sodium nitrite and 78.4 pts. by wt. of zinc dust as well as 77.1 pts. by wt. of 4-carboxy-benzaldehyde are reacted as in Example 1.1. This gives 82.8 pts. by wt. of 1-(4-carboxy)-benzalimino-2-oxo-imidazolidine, which is suspended in 200 pts. by vol. of methanol, and ethereal diazomethane solution is added until the yellow coloration remains. Shortly after a clear solution has formed, 1-(4-methoxycarbonyl)-benzalimino-2-oxo-imidazolidine of melting point 245°–6° C. crystallises out.

IR (KBr): 2240 and 1700 with a shoulder at 1720 cm$^{-1}$.

NMR (d$_6$-DMSO): 7.6–8.1 (AB system and s at 7.63; 5H), 7.20 (s, broad, 1H), 3.88 (s, 3H) and m centred at 3.7 (4H) δ.

calculated: C, 58.29; H, 5.30; N, 17.00; O, 19.41. found: C, 58.7; H, 5.2; N, 17.3; O, 19.6.

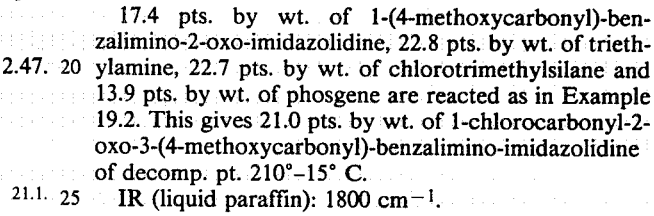

21.2.

17.4 pts. by wt. of 1-(4-methoxycarbonyl)-benzalimino-2-oxo-imidazolidine, 22.8 pts. by wt. of triethylamine, 22.7 pts. by wt. of chlorotrimethylsilane and 13.9 pts. by wt. of phosgene are reacted as in Example 19.2. This gives 21.0 pts. by wt. of 1-chlorocarbonyl-2-oxo-3-(4-methoxycarbonyl)-benzalimino-imidazolidine of decomp. pt. 210°–15° C.

IR (liquid paraffin): 1800 cm$^{-1}$.

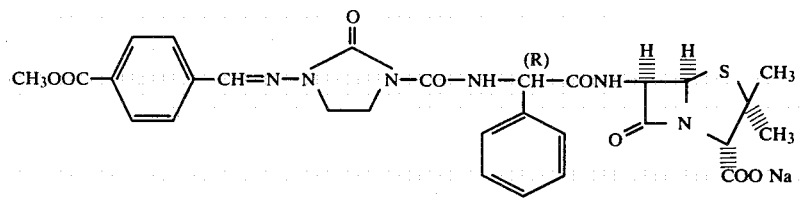

21.3.

6.2 pts. by wt. of ampicillin trihydrate and 4.6 pts. by wt. of 1-chlorocarbonyl-2-oxo-3-(4-methoxycarbonyl)-benzalimino -imidazolidine are reacted as in Example 2.3. This gives 5.4 pts. by wt. of sodium 6-{D-α[(2-oxo-3-{4-methoxycarbonyl}-benzalimino-imidazolidin-1-yl)-carbonylamino]-phenylacetamido}-penicillinate of decomp. pt. 215°–20° C.

IR (KBr): 1760, 1720, 1665 and 1595 cm$^{-1}$.

NMR (CD$_3$OD): 8.0–7.1 (aromatic protons and —CH═N—, 10H), 5.58 (s, 1H), 5.45 (q, 2H), 4.15 (s, 1H), m at about 3.8 (4H), 2.30 (s, 3H), 1.57 (s, 3H) and 1.50 (s, 3H), δ.

$C_{29}H_{29}N_6NaO_8S\cdot 3H_2O$: calculated: C, 49.86; H, 5.05; N, 12.02; S, 4.58. found: C, 49.7; H, 5.2; N, 11.9; S, 4.4.

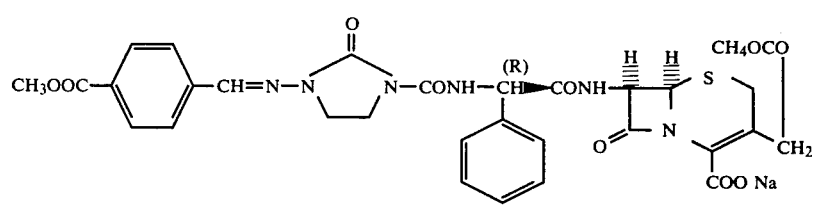

21.4.

2.3 pts. by wt. of cephaloglycine dihydrate in 40 pts. by vol. of 80 percent strength aqueous THF are reacted with 2.2 pts. by wt. of 1-chlorocarbonyl-2-oxo-3-(4-methoxycarbonyl)-benzalimino-imidazolidine as in Example 1.6. This gives 1.0 pts. by wt. of sodium 7-{D-α-[(2-oxo-3-{4-methoxycarbonyl}-benzalimino-imidazolidin-1-yl)-carbonylamino]-phenylacetamido}-3-acetoxymethy-ceph-3-em-carboxylate.

IR (KBr): 1755, 1725, 1665 and 1600 cm$^{-1}$.
$C_{31}H_{29}N_6NaO_{10}S \cdot 3H_2O$: calculated: C, 49.34; H, 4.67; N, 11.14; S, 4.25. found: C, 49.1; H, 4.5; N, 11.1; S, 4.4.

EXAMPLE 22

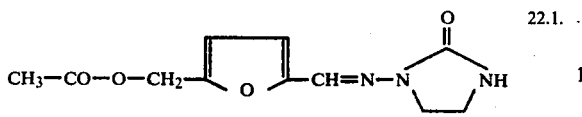

22.1.

A solution of 1-amino-2-oxo-imidazolidine (3.0 pts. by wt.) in water (30 pts. by vol.) is added to a suspension of 5-acetoxymethyl-furane-2-aldehyde (5.0 pts. by wt.) in water (50 pts. by vol.) in the course of 30 minutes, whilst stirring and cooling with ice/water. The mixture is subsequently stirred for a further 20 hrs. at 20° C. and the precipitate is then filtered off and washed with isopropanol. The substance was dried at 70° C. over $P_4O_{10}$ in vacuo.

Yield: 6.6 pts. by wt. Melting point=146° C. calculated: C, 52.6; H, 5.2; N, 16.7; O, 25.5. found: C, 52.6; H, 5.3; N, 16.8; O, 25.8.

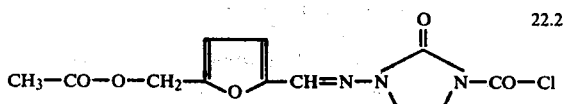

22.2

A solution of trimethylchlorosilane (3.2 pts. by wt.) in benzene is added dropwise to a mixture, boiling under reflux, of 1-(5-acetoxymethyl-furfurylideneamino)-2-oxo-imidazolidine (6.6 pts. by wt.), benzene (60 pts. of vol.) and triethylamine (4.1 pts. by vol.) and the mixture is then boiled for a further 20 hrs. The triethylamine hydrochloride is then filtered off while still hot and rinsed with benzene and a solution of phosgene (1.6 pts. by vol.) in benzene (10 pts. by vol.) is added to the combined filtrates, whilst cooling. The mixture is left to stand for 20 hrs. at 20° C. and the precipitate is then filtered off.

Yield: 4.3 pts. by wt. Melting point = 184°-85° C.
IR spectrum (carbonyl range): 1810 and 1745 cm$^{-1}$. (in liquid paraffin)
calculated: C, 45.9; H, 3.8; Cl, 11.3; N, 13.4; O, 25.5. found: C, 46.4; H, 3.9; Cl, 11.1; N, 13.4; O, 25.3.

This penicillin is formed when ampicillin trihydrate (2.0 pts. by wt.) and 1-chlorocarbonyl-2-oxo-3-(5-acetoxymethyl-furfurylidene-amino)-imidazolidine (1.75 pts. by wt.) are reacted with one another in the manner described in Example 1.3.

Yield: 2.8 pts. by wt. of sodium D-α-{[2-oxo-3-(5-acetoxymethylfurfurylideneamino)-imidazolidin-1-yl]-carbonylamino}-benzylpenicillin.

Melting point=agglutination from about 190° C., then increasing decomposition.

NMR signals at τ=2.37 (1H), 2.5–2.85 (5H), 3.15–3.30 (d, 1H), 3.40–3.55 (d, 1H), 4.43 (1H), 4.43–4.70 (AB, 2H), 4.93 (2H), 5.87 (1H), 5.98–6.30 (4H), 7.94 (3H), 8.45 (3H) and 8.52 ppm (3H).

IR spectrum (carbonyl range): 1767 (shoulder), 1734, 1660, (in liquid paraffin) 1600 and 1530–1510 cm$^{-1}$
β-Lactam content: 92%.

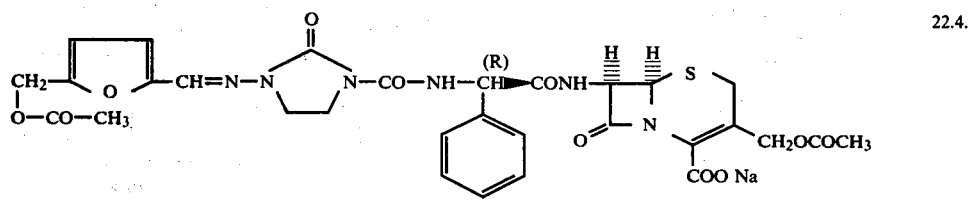

22.4.

This cephalosporin is obtained when cephaloglycine dihydrate (2.0 pts. by wt.) and 1-chlorocarbonyl-2-oxo-3-(5-acetoxymethyl-furfurylidene-amino)-imidazolidine (1.5 pts. by wt.) are reacted with one another in the manner such as is described for penicillins in Examples 1.3. and 1.6. On acidifying, this gives one part of the cephalosporin as a precipitate which is insoluble in water and in the organic phase (ethyl acetate): (yield: 0.1 pt. by wt.; melting point=tacky at 205° C., increasing decomposition up to 260° C., but no clear melt; IR spectrum, carbonyl range: 1770, 1726, 1678, 1600 and 1528 cm$^{-1}$ in liquid paraffin). The cephalosporin can then be precipitated from the organic phase as described.

Yield: 2.7 pts. by wt. of sodium 7-D-α-[{[2-oxo-3-(5-acetoxymethyl-furfurylidene-amino)-imidazolidin-1-yl]-carbonylamino}-phenylacetamido]-3-acetoxymethyl-ceph-3-em-4-carboxylate.

β-Lactam content: 86%.

IR spectrum (carbonyl range): 1770 (shoulder), 1760 (shoulder), 1730, 1668, 1610, 1550 (shoulder) and 1530 cm$^{-1}$.

NMR signals at τ=2.33 (1H), 2.45–2.85 (5H), 3.15–3.25 (1H), 3.4–3.52 (1H), 4.24–4.48 (2H), 4.92 (2H), 5.0–5.22 (3H), 6.0–6.27 (4H), 6.55–6.75 (2H), 7.96 (3H) and 8.02 ppm (3H).

Melting point=from 220° C. falling and decomp.

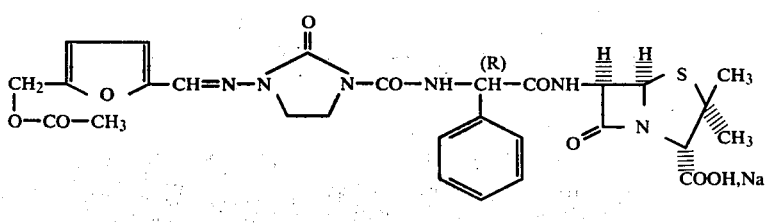

22.3.

EXAMPLE 23

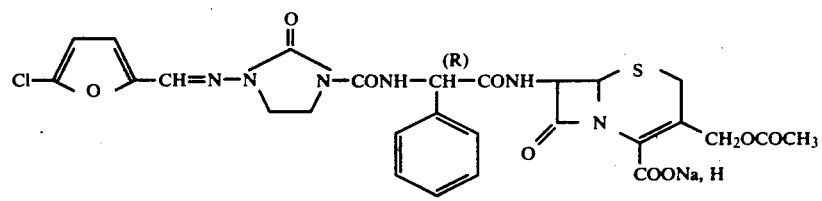

23.4.

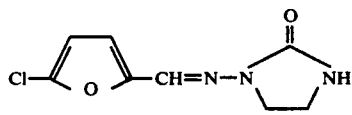

23.1.

2-Chlorofurane-5-aldehyde is reacted with 1-amino-2-oxo-imidazolidine as in Example 1.1. This gives 1-(5-chlorofurylideneamino)-2-oxo-imidazolidine of melting point 173–175° C.

NMR (d$_6$-DMSO): 7.45 (s, 1H), 7.26 (s, broad, 1H), 6.77 (d, 1H), 6.60 (d, 1H) and 3.55 (m, 4H) δ.

calculated: C, 45.0; H, 3.7; N, 19.7; Cl, 16.6. found: C, 45.5; H, 3.8; N, 20.0; Cl, 16.2.

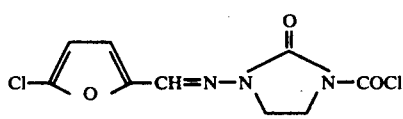

23.2.

20.0 pts. by wt. of 1-(5-chlorofurylideneamino)-2-oxo-imidazolidine, 31.8 pts. by wt. of triethylamine, 31.8 pts. by wt. of chlorotrimethylsilane and 18.6 pts. by wt. of phosgene are reacted as in Example 1.2.

This gives, after recrystallisation from acetonitrile, 16.5 pts. by wt. of 1-chlorocarbonyl-2-oxo-3-(5-chlorofurylideneamino)-imiadzolidine of decomp. pt. 193°–196° C.

calculated: Cl, 25.68. found: Cl, 25.7.

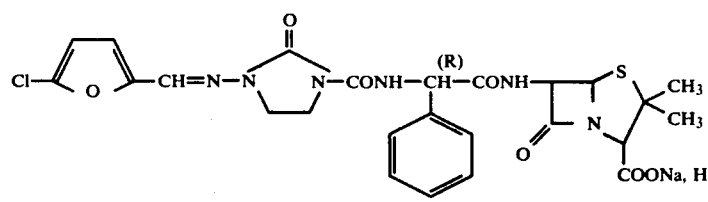

23.3.

3.9 pts. by wt. of 1-chlorocarbonyl-2-oxo-3-(5-chlorofurylideneamino)-imidazolidine and 5.0 pts. by wt. of ampicillin trihydrate in 100 pts. by vol. of 80 percent strength aqueous THF are reacted as in Example 1.3. This gives 4.7 pts. by wt. of sodium 6-{D-α-[(2-oxo-3-{5-chloroflurylideneamino}-imidazolidin-1-yl)-carbonylamino]-phenylacetamido}-penicillanate of decomp. pt. 210°–220° C.

IR (KBr): 1760, 1720, 1660, 1600, 1525, 1470, 1405, 1270 and 1225 cm$^{-1}$.

NMR (CD$_3$OD): 7.55 (s, 1H), 7.3 (m, 5H), 6.82 (d, 1H), 6.35 (d, 1H), 5.56 (s, 1H), 5.43 (pseudo q, 2H), 4.12 (s, 1H), 3.82 (s, broad, 4H), 1.55 (s, 3H) and 1.48 (s, 3H) δ.

C$_{25}$H$_{24}$ClN$_6$NaO$_7$S.1½H$_2$O calculated: C, 47.06; H, 4.27; N, 13.18; S, 5.04. found: C, 47.1; H, 4.7; N, 13.2; S, 5.2.

5.0 pts. by wt. of cephaloglycine dihydrate in 100 pts. by vol. of 80 per cent strength aqueous THF and 3.5 pts. by wt. of 1-chlorocarbonyl-2-oxo-3-(5-chlorofurylideneamino)-imidazolidine are reacted as in Example 1.6. This gives 4.3 pts. by wt. of sodium 7-{D-α-[(2-oxo-3-{5-chlorofurylideneamino}-imidazolidin-1-yl)-carbonylamino]-phenylacetamido}-3-acetoxymethyl-ceph-3-em-4-carboxylate of decomp. pt. 185°–190° C.

IR (KBr): 1765, 1720, 1660, 1595, 1520, 1405 and 1225 cm$^{-1}$.

NMR (CD$_3$OD/D$_2$O): 7.48 (s) and 7.37 (m, a total of 6H), 6.78 (1H), 6.34 (1H), 5.65 (1H), 5.43 (1H), 4.95 (overlaid by the signal of the replaceable protons), 3.8 (s, broad, 4H), 3.6 (overlaid by the solvent peak) and 2.06 (s, 3H) δ.

EXAMPLE 24

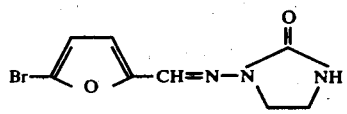

24.1.

33.5 pts. by wt. of 2-bromofurane-5-aldehyde, dissolved in 100 pts. by vol. of THF, are added to a solution of 1-amino-2-oxo-imidazolidine hydrochloride in 350 pts. by vol. of water, adjusted to pH 5 with sodium hydroxide solution, and the mixture is stirred overnight. The precipitate is filtered off, washed with water and recrystallised from methanol. This gives 30.0 pts. by wt. of 1-(5-bromofurylideneamino)-2-oxo-imidazolidine of decomp. pt. 153°–158° C.

IR (KBr): 1720, 1580, 1410, 1265 and 1245 cm$^{-1}$.

NMR (d$_6$-DMSO): 7.55 (s, 1H), 7.31 (s, 1H), 6.80 (AB, 2H) and m at about 3.6 (4H) δ.

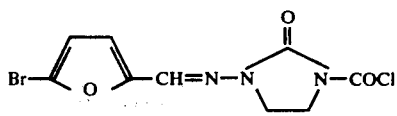

24.2.

30.0 pts. by wt. of 1-(5-bromofurylideneamino)-2-oxo-imidazolidine, 37.8 pts. by wt. of triethylamine, 36.8 pts. by wt. of chlorotrimethylsilane as well as 23.0 pts. by wt. of phosgene are reacted as in Example 1.2.

This gives, after recrystallisation from acetonitrile, 21.6 pts. by wt. of 1-chlorocarbonyl-2-oxo-3-(5-bromofurylideneamino)-imidazolidine of decomp. pt. 190°–194° C.

IR (liquid paraffin): 1815 cm$^{-1}$.

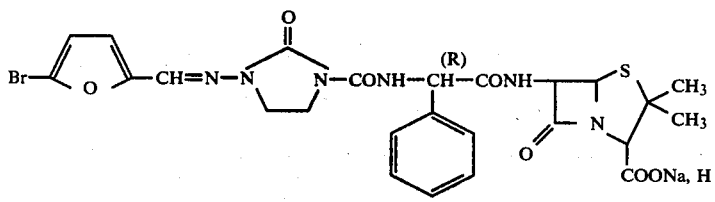

6.1 pts. by wt. of ampicillin trihydrate and 3.2 pts. by wt. of 1-chlorocarbonyl-2-oxo-3-(5-bromofurylideneamino)-imidazolidine in 80 pts. by vol. of 80 per cent strength aqueous THF are reacted as in Example 1.3. This gives 3.7 pts. by wt. of sodium 6-{D-α-[(2-oxo-3-{5-bromofurylideneamino}-imidazolidin-1-yl)-carbonylamino]-phenylacetamido}-penicillanate of decomp. pt. 220°–228° C.

IR (KBr): 1760, 1725, 1660, 1600, 1400 and 1225 cm$^{-1}$.

NMR (CD$_3$OD): 7.60 (s, 1H), 7.46 (s, 5H), 6.83 (d, 1H), 6.52 (d, 1H), 5.58 (s,1H), 5.50 (AB, 2H), 4.18 (s, 1H), 3.85 (s, broad, 4H), 1.57 (s, 3H) and 1.50 (s, 3H) δ.

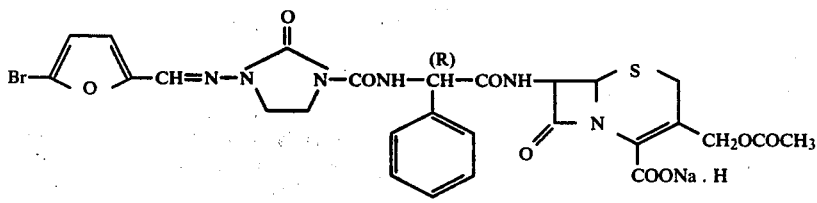

4.5 pts. by wt. of cephaloglycine dihydrate and 3.3 pts. by wt. of 1-chlorocarbonyl-2-oxo-3-(5-bromofurylideneamino)-imidazolidine in 100 pts. by vol. of 80 percent strength aqueous THF are reacted as in Example 1.6. This gives 3.3 pts. by wt. of sodium 7-{D-α-[(2-oxo-3-{5-bromofurylideneamino}-imidazolidin-1-yl)-carbonylamino]-phenylacetamido}-3-acetoxymethyl-ceph-3-em-4-carboxylate of decomp. pt. 187°–196° C.

IR (KBr): 1775, 1715, 1655, 1450 and 1275 cm$^{-1}$.

NMR (CD$_3$OD/D$_2$O): 7.55 (s, 1H), 7.4 (m, 5H), 6.80 (d, 1H), 6.50 (d, 1H), 5.68 (d, 1H), 5.50 (s, 1H), 4.96 (d, 1H), 4.92 (overlaid by the signal of the replaceable protons), 3.80 (s, broad, 4H), 3.4 (overlaid by the solvent peak) and 2.08 (s, 3H) δ.

EXAMPLE 25

25.1.

24.3.

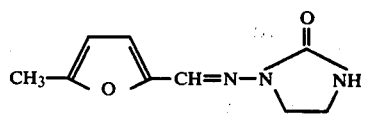

98.3 pts. by wt. of 2-methylfurane-5-aldehyde are added to a solution of 1-amino-2-oxo-imidazolidine hydrochloride in 1,000 pts. by vol. of water, brought to pH 4.5 with sodium hydroxide solution, and the mixture is stirred overnight. The precipitate is filtered off, washed with water and recrystallised from ethanol. This gives 126 pts. by wt. of 1-(5-methylfurylideneamino)-2-oxo-imidazolidine of melting point 194°–6° C.

IR (KBr): 3320, 1735, 1710, 1480, 1420, 1395 and 1245 cm$^{-1}$.

NMR (d$_6$-DMSO): 7.57 (s, 1H), 7.22 (s, broad, 1H), 24.4.

6.67 and 6.25 (AB system, 2H), 3.65 (m, 4H) and 2.38 (s, 3H) δ.

calculated: C, 55.95; H, 5.74; N, 21.75. found: C, 56.0; H, 5.8; N, 21.3.

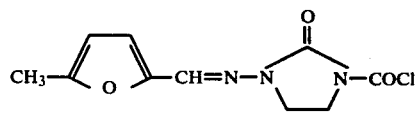

25.2.

50.0 pts. by wt. of 1-(5-methylfurylideneamino)-2-oxo-imidazolidine, 84.3 pts. by wt. of triethylamine, 84.0 pts. by wt. of chlorotrimethylsilane and 51.4 pts. by wt. of phosgene are reacted as in Example 1.2. This gives, after recrystallisation from acetonitrile, 50.7 pts. by wt. of 1-chlorocarbonyl-2-oxo-3-(5-methyl-furylideneamino)-imidazolidine of decomp. pt. 180°–186° C.

IR (liquid paraffin): 1815 cm$^{-1}$.

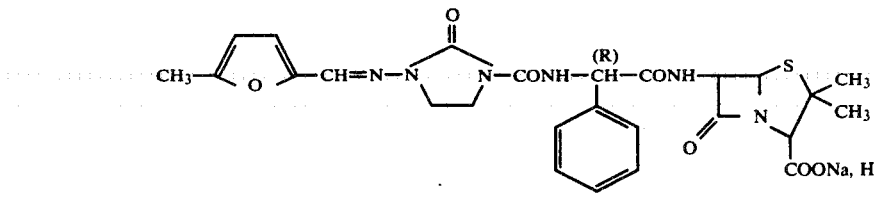

6.1 pts. by wt. of ampicillin trihydrate and 2.6 pts. by wt. of 1-chlorocarbonyl-2-oxo-3-(5-methyl-furylideneamino)-imidazolidine in 80 pts. by vol. of 80 percent strength aqueous THF are reacted as in Example 1.3. This gives 4.2 pts. by wt. of sodium 6-{D-α-[(2-oxo-3-{5-methylfurylideneamino}-imidazolidin-1-yl)-carbonylamino]-phenylacetamido}-penicillanate of decomp. pt. 210°–220° C.

IR (KBr): 1760, 1720, 1660, 1600, 1525 and 1410 cm$^{-1}$.

NMR (CD$_3$OD): 7.62 (s, 1H), 7.35 (m, 5H), 6.75 (d, 1H), 6.13 (d, 1H), 5.60 (s, 1H), 5.45 (AB, 2H), 4.18 (s, 1H) 3.83 (s, broad, 4H), 2.35 (s, 3H), 1.56 (s, 3H) and 1.49 (s, 3H).

14.0 pts. by wt. of 5-methyl-3-formyl-isoxazole are reacted with 25.6 pts. by wt. of 1-amino-2-oxo-imidazolidine hydrochloride in 100 pts. by vol. of water as in Example 25.1. After 90 minutes, the precipitate is filtered off, washed with water, dried and recrystallised from absolute acetonitrile. This gives 12.5 pts. by wt. of 1-(5-methyl-isoxazol-3-yl-methyleneamino)-2-oxo-imidazolidine of melting point 195°–7° C.

IR (liquid paraffin): 3220, 1695 and 1610 cm$^{-1}$.

NMR (CD$_3$OD): 7.65 (s, 1H), 7.47 (s, broad, 1H), 6.53 (s, 1H), 3.7 (m, 4H) and 2.50 (s, 3H) δ.

calculated: C, 49.48; H, 5.19; N, 28.85. found: C, 49.6; H, 5.2; N, 29.2.

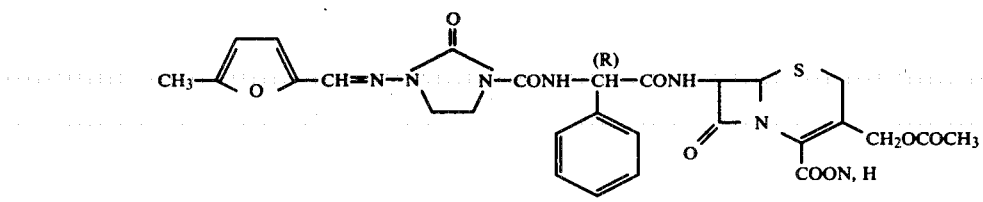

4.4 pts. by wt. of cephaloglycine dihydrate and 2.6 pts. by wt. of 1-chlorocarbonyl-2-oxo-3-(5-methyl-furylideneamino)-imidazolidine in 80 pts. by vol. of 80 percent strength aqueous THF are reacted as in Example 1.6. This gives 4.4 pts. by wt. of sodium 7-{D-α-[(2-oxo-3-{5-methylfurylideneamino}-imidazolidin-1-yl)-carbonylamino]-phenylacetamido}-3-acetoxymethyl-ceph-3-em-4-carboxylate.

IR (KBr): 1760, 1725, 1660, 1600, 1525, 1405 and 1225 cm$^{-1}$.

NMR (CD$_3$OD): 7.70 (s, 1H), 7.40 (m, 5H), 6.80 (d, 1H), 6.20 (d, 1H), 5.75 (d, 1H), 5.68 (s, 1H), 4.95 (m, overlaid by the signal of the replaceable protons), 3.88 (s, broad, 4H), 3.45 (overlaid by the solvent peak), 2.35 (s, 3H) and 2.04 (s, 3H) δ.

EXAMPLE 26

26.1.

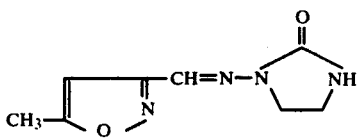

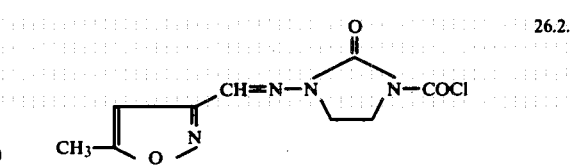

12.0 pts. by wt. of 1-(5-methyl-isoxazol-3-yl-methyleneamino)-2-oxo-imidazolidine, 21.0 pts. by wt. of triethylamine, 20.8 pts. by wt. of chlorotrimethylsilane and 12.3 pts. by wt. of phosgene are reacted as in Example 1.2.

This gives 19.8 pts. by wt. of 1-chlorocarbonyl-2-oxo-3-(5-methyl-isoxazol-3-yl-methyleneamino)-imidazolidine of melting oint 199°–203° C. The compound still contains small amounts of triethylamine hydrochloride, which do not need to be removed since they are not troublesome in the subsequent reaction.

IR (liquid paraffin): 1790 cm$^{-1}$.

26.3.

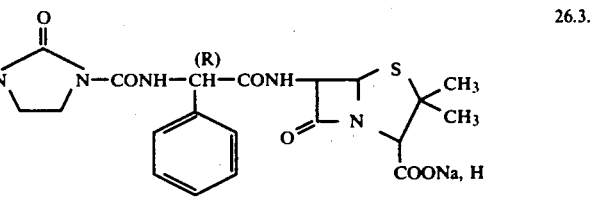

16.5 pts. by wt. of ampicillin trihydrate and 9.5 pts. by wt. of 1-chlorocarbonyl-2-oxo-3-(5-methylisoxazol-3-yl-methyleneamino)-imidazolidine in 100 pts. by vol. of 80 percent strength aqueous THF are reacted as in Example 1.6. This gives 1.0 pt. by wt. of sodium 6-{D-

α-[(2-oxo-3-{5-methylisoxazol-3-yl-methyleneamino}-imidazolidin-3-yl)-carbonylamino]-phenylacetamido}-penicillanate.

IR (KBr): 1760, 1730, 1660, 1600, 1525, 1395 and 1225 cm$^{-1}$.

NMR (CD$_3$OD/D$_2$O): 7.72 (s, 1H), 7.38 (s, 5H), 6.62 (s, 1H), 5.53 (s, 1H), 5.43 (m, 2H), 4.13 (s, 1H), 3.90 (m, 4H), 2.45 (s, 3H), 1.53 (s, 3H), and 1.48 (s, 3H) δ.

calculated: C, 42.9; H, 3.6; N, 25.0; O, 28.6. found: C, 42.8; H, 3.7; N, 25.2; O, 29.1.

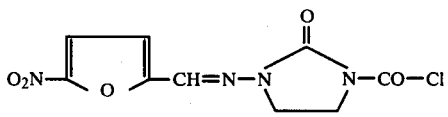

27.2

26.4.

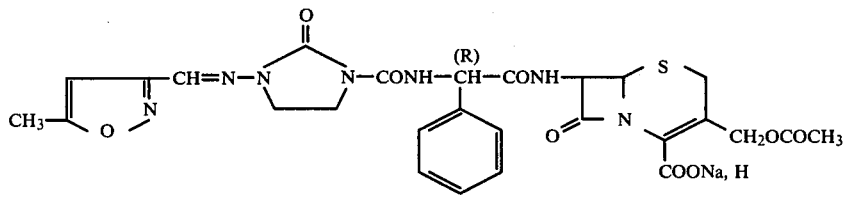

18.1 pts. by wt. of cephaloglycine dihydrate and 9.5 pts. by wt. of 1-chlorocarbonyl-2-oxo-3-(methylisoxazol-3-yl-methyleneamino)-imidazolidine in 150 pts. by vol. of 80 percent strength aqueous THF are reacted as in Example 1.6.

This gives 2.2 pts. by wt. of sodium 7-{D-α-[(2-oxo-3-{5-methyl-isoxazol-3-yl-methyleneamino}-imidazolidin-1-yl)-carbonylamino]-phenylacetamido}-3-acetoxymethyl-ceph-3-em-4-carboxylate. Decomp. pt. 215°-220° C.

8.0 pts. by wt. of the product described above (27.1.) are silylated in the manner described in Example 1.2. and then reacted with phosgene (2.6 pts. by vol.).

Yield: 5.2 pts. by wt.

Melting point=188°-190° C. (Kofler stage)

The substance still contains some triethylamine hydrochloride (the majority is removed by washing with dichloromethane) which, however, is not troublesome in the further reaction.

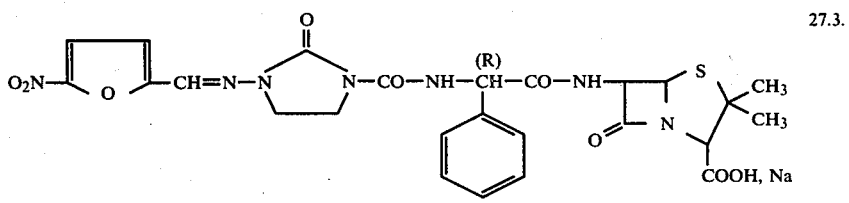

27.3.

IR (KBr): 1760, 1730 (shoulder), 1670, 1595 and 1395 cm$^{-1}$.

NMR (CD$_3$OD/D$_2$O): 7.74 (s, 1H), 7.38 (s, 5l H), 6.63 (s, 1H), 5.65 (d, 1H), 5,50 (s, 1H), 4.95 (overlaid by the signal of the replaceable protons), 3.90 (s, broad, 4H), 3.4 (overlaid by the solvent peak), 2.45 (s, 3H) and 2.05 (3, 3H) δ.

EXAMPLE 27

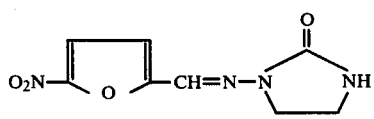

27.1.

2-(Diacetoxymethyl)-5-nitro-furane (48.6 pts. by wt.) are boiled in a mixture of water (216 pts. by vol.) and concentrated H$_2$SO$_4$ (108 pts. by wt.) for 15 minutes under N$_2$, the mixture is then cooled and the 5-nitro-furfurol formed is taken up in ether and, after removing the ether, dissolved in 100 pts. by vol. of methanol. A solution of 1-amino-2-oxo-imidazolidine hydrochloride (27.5 pts. by wt.) in water (100 pts. by vol.) is added to this solution. After 4.5 hrs., the product which has separated out is filtered off, washed with water and dried.

Yield: 42.1 pts. by wt.

Melting point=259°-260° C. (Kofler heated stage)

This penicillin is obtained when ampicillin trihydrate (1.5 pts. by wt.) is reacted with 1-chlorocarbonyl-2-oxo-3-(5-nitro-furylideneamino)-imidazolidine (1.1 pts. by wt.) in the manner described in Example 1.3. This gives, after working up, 0.7 pt. by wt. of the crude sodium salt. For purification, this is suspended in a little water and the undissolved material is filtered off and dried (1st yield: 0.3 pt. by wt.). The aqueous filtrate is covered with a layer of ethyl acetate and acidified down to pH 1.5 and the sodium salt is precipitated from this mixture in the manner already described (2nd yield: 0.2 pt. by wt.).

Total yield: 0.5 pt. by wt. of sodium D-α-{[2-oxo-3-(5-nitrofurylideneamino)-imidazolidin-1-yl]-carbonylamino}benzylpenicillin.

β-Lactam content (according to the NMR spectrum and elementary analysis): 44%. The substance also contains 44% of the product with an open β-lactam ring (the reaction mixture had stood at 20° C. for a relatively long time after the acidification).

According to the NMR spectrum and the analysis, the substance contains (including that consumed in the opening of the β-lactam ring) 4.8 molar equivalents of water. This was taken into consideration in the following calculated analysis data:

calculated: C, 42.4; H, 4.8; N, 13.8; S, 4.5. found: C, 42.1; H, 4.8; N, 13.8; S, 4.3.

Melting point=decomposition from about 260° C.

IR spectrum (carbonyl range): 1775 (shoulder), 1745, 1665, 1590 and 1515 cm$^{-1}$ (in Nujol).

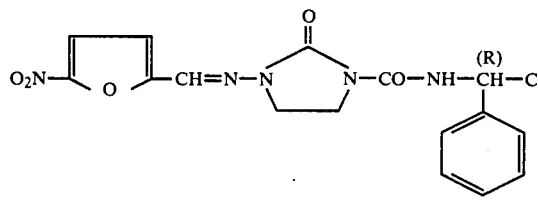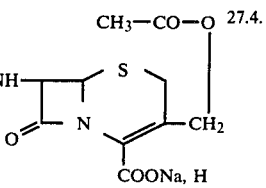

27.4.

The cephalosporin is obtained when cephaloglycine dihydrate (4.0 pts. by wt.) is reacted with 1-chlorocarbonyl-2-oxo-3-(5-nitro-furylidene-amino)-imidazolidine (2.5 pts. by wt.) with one another in the manner described in Example 1.3. and 1.6. On acidifying the reaction mixture, freed from tetrahydrofurane, only some of the cephalosporic acid formed dissolves in the ethyl acetate. The rest precipitates. The sodium salt is then obtained from the two fractions in the manner already described.

Yield: 2.8 pts. by wet. of sodium 7-{D-α-[(2-oxo-3-{5-nitro-furylideneamino}-imidazolidin-1-yl)-carbonylamino]-phenylacetamido}-3-acetoxymethyl-ceph-3-em-4-carboxylate.

Melting point=decomposition from about 230° C.—up to 260° C., but no clear melt (Kofler heated stage)

β-Lactam content (determined iodometrically) 84%.

NMR signals at τ=1.95-2.9 (8H), 4.1-4.5 (2H), 4.9-5.2 (3H), (in d₆-DMF) 6.0 (4H), 6.6-6.85 (2H and 8.0 ppm/3H).

IR spectrum (carbonyl range): 1765 (shoulder), 1725, 1670, 1600 and 1510 cm⁻¹ (in Nujol).

EXAMPLE 28

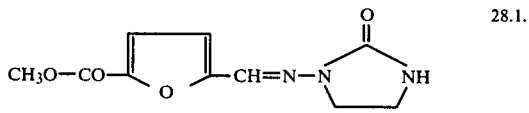

28.1.

This substance is obtained from 1-amino-2-oxo-imidazolidine (1.2 pts. by wt.) and 5-methoxycarbonyl-furfural (1.8 pts. by wt.) in aqueous methanol (1:1; 12 pts. by vol.) at 20° C. in 60 minutes.

Yield: 2.7 pts. by wt.

Melting point=sticky from 88° C. (Kofler stage).

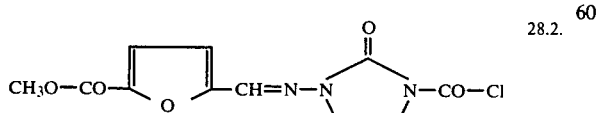

28.2.

2.6 pts. by wt. of the product described above (29.1.) are silylated in the manner described in Example 1.2. and then reacted with phosgene (0.8 pt. by vol.).

Yield: 1.5 pts. by wt.

Melting point=(crude product, still contains some triethylamine hydrochloride)=about 220° C., decomposition (Kofler stage).

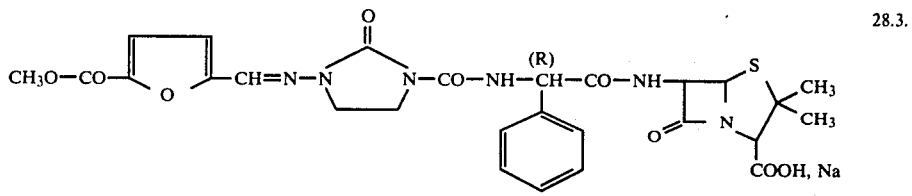

28.3.

This penicillin is obtained from 0.87 pt. by wt. of ampicillin trihydrate when this compound is reacted with 0.65 pt. by wt. of 1-chlorocarbonyl-2-oxo-3-(5-methoxycarbonylfurylidene-amino)-imidazolidine, in the manner described in Example 1.3.

Yield: 0.5 pt. by wt. of sodium D-α-{[2-oxo-3-(5-methoxycarbonyl-furylidene-amino)-imidazolidin-1-yl]-carbonylamino}-benzylpenicillin.

β-Lactam content (determined iodometrically): 80%.

Melting point=185°-210° C., decomposition (Kofler stage).

IR spectrum (carbonyl range): 1770, 1730, 1670, 1605 and 1530 cm⁻¹ (in Nujol).

EXAMPLE 29

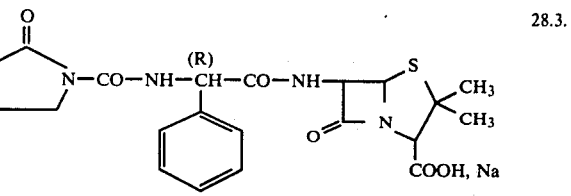

29.1.

This substance is obtained from 1-amino-2-oxo-imidazolidine (1.3 pts. by wt.) and 5-ethoxycarbonyl-furfural (2.6 pts. by wt.) in aqueous methanol.

Yield: 3.1 pts. by wt.

Melting point (crude product)=135°-138° C. (Kofler stage).

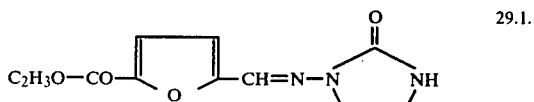

29.2.

2.85 pts. by wt. of the product described above (30.1.) are silylated in the manner described in Example 1.2. (but using dioxane as the solvent) and then reacted with phosgene (0.9 pt. by vol.)

Yield: 1.1 pts. by wt.

Melting point=230°-233° C. (Kofler stage) (crude product).

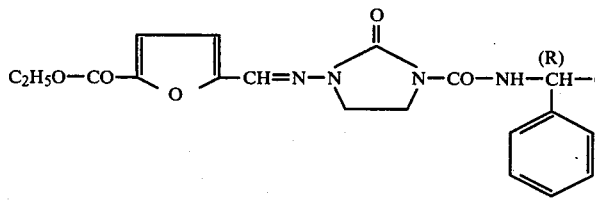
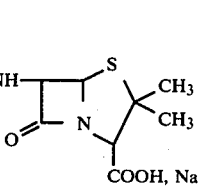

29.3.

This penicillin is obtained when ampicillin trihydrate (1.3 pts. by wt.) is reacted with 1-chlorocarbonyl-2-oxo-3-(5-ethoxycarbonyl-furylidene-amino)-imidazolidine (1.0 pt. by wt.) with one another in the manner described in Example 1.3.

Yield: 0.8 pt. by wt. of sodium D-α-{[2-oxo-3-(5-ethoxycarbonyl-furylidene-amino)-imidazolidin-1-yl]-carbonylamino}-benzylpenicillin.

β-Lactam content (determined iodometrically): 92% (the substance contains about 6% of the product with an open β-lactam ring).

Melting point = about 220° C., decomposition (Kofler stage).

IR spectrum (carbonyl range): 1775–1790, 1740, 1675, 1610 and 1520–1540 cm$^{-1}$ (in Nujol).

According to the analysis and the NMR data, the penicillin contains about 4.3 molar equivalents of water and 0.16 molar equivalent of sodium 2-ethylhexanoate.

This was taken into consideration in the following calculated analysis figures:

calculated: C, 46.7; H, 5.3; N, 11.2; S, 4.3. found: C, 46.7; H, 5.6; N, 11.2; S, 4.5.

EXAMPLE 30

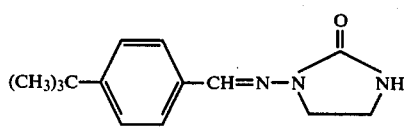

30.1.

The precursor is obtained when 1-amino-2-oxo-imidazolidine hydrochloride (6.9 pts. by wt.) is dissolved in 1 N sodium hydroxide solution (50 pts. by vol.), 4-tertiary-butyl-benzaldehyde (8.0 pts. by wt.) is added and the mixture is stirred for 24 hrs. at 20° C. The product which has precipitated is recrystallised from acetonitrile.

Yield: 5.9 pts. by wt.
Melting point = 208° C. (Kofler stage).

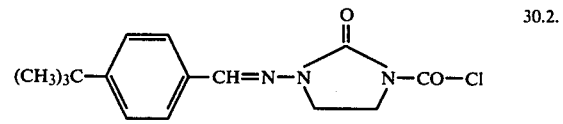

30.2.

This substance is obtained, using the procedure described in Example 1.2., from the product (5.5 pts. by wt.) described above (31.1.), after silylation with triethylchlorosilane (4.4 pts. by wt.) and subsequent reaction with phosgene (2.1 pts. by vol.), using dioxane as the solvent.

The substance still contained some triethylamine hydrochloride.

IR spectrum (COCl): 1808 cm$^{-1}$ (in Nujol).

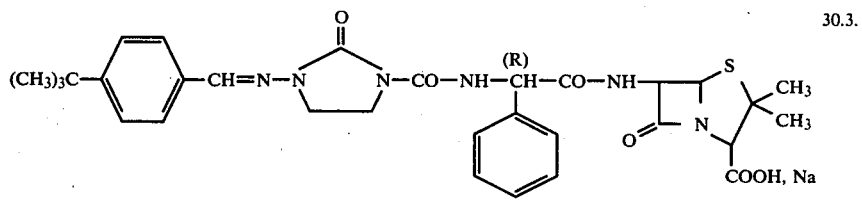

30.3.

This penicillin is obtained when ampicillin trihydrate (2.2 pts. by wt.) is reacted with 1-chlorocarbonyl-2-oxo-3-(4-tertiary butyl-benzalimino)-imidazolidine (see above; 2.0 pts. by wt.) using the procedure described in Example 1.3.

Yield: 2.7 pts. by wt. of sodium 6-{D-α-[(2-oxo-3-{4-tertiary butyl-benzalimino}-imidazolidin-1-yl)-carbonylamino]-phenylacetamido}-penicillanate.

β-Lactam content (iodometrically): 83% (the penicillin contained about 10% of the product with an open β-lactam ring).

Melting point = tacky from about 240° C., a dark melt at about 259° C., which rapidly solidified again as a result of decomposition.

NMR signals at τ = 2.15–2.8 (10H), 4.4 (1H), 4.4–4.65 (2H), (in CD$_3$OD) 5.85 (1H), 6.3 (broad, 4H), 8.45 (3H), 8.52 (3H) and 8.75 ppm (9H).

The NMR spectrum shows that the substance contains about 1.8 molar equivalents of water. This was taken into consideration in the calculated analysis figures:

calculated: C, 55.1; H, 5.8; N, 12.4; S, 4.7. found: C, 55.1; H, 5.9; N, 12.4; S, 4.8.

IR spectrum (carbonyl range): 1772, 1730, 1672, 1610 and 1515–1530 cm$^{-1}$ (in Nujol).

EXAMPLE 31

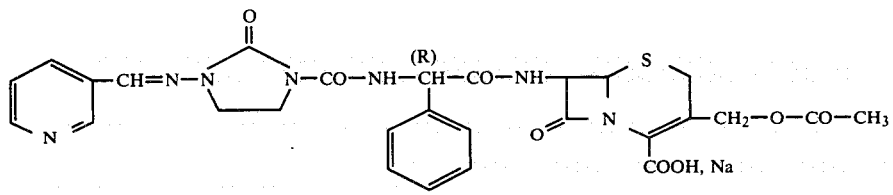

To prepare this cephalosporin, cephaloglycine dihydrate (1.5 pt. by wt.) and 1-chlorocarbonyl-2-oxo-3-(3-pyridylmethylidene-amino)-imidazolidine (0.8 pts. by wt.) are reacted in the manner described in Examples 1.3. and 1.6. After removing the tetrahydrofurane and acidifying the mixture to pH 1.5, the free cephalogsporic acid separates out as a precipitate (0.8 pt. by wt.; melting point: decomposition from about 200° C.-to 260° C., no clear melt [Kofler heated stage]; IR bands at 1770, 1745, 1675 and 1520–1550 cm$^{-1}$ [Nujol]), which is insoluble in water and ethyl acetate. This acid is dissolved in a little dimethylformamide, 1.3 pts. by vol. of an approximately 1 molar sodium 2-ethylhexanoate solution in methanol-containing ether are added and the sodium salt of the cephalosporin is precipitated with ether.

Yield: 0.6 pt. by wt. of sodium 7-{D-α-[(2-oxo-3-{3-pyridyl-methylidene-amino}-imidazolidin-1-yl)-carbonylamino]-phenylacetamido}-3-acetoxymethyl-ceph-3-em-4-carboxylate.

Melting point=on sprinkling the finely powdered substance onto the Kofler heated stage, it melts briefly to give a clear melt from 242° C. and then decomposes and solidifies immediately - no further melting up to 260° C.

IR spectrum (carbonyl range): 1770 (shoulder), 1760, 1730, 1670, 1605 and 1530–1550 cm$^{-1}$ (in Nujol).

According to the NMR spectrum, the substance contains about 5.5 molar equivalents of water and 0.26 molar equivalent of sodium 2-ethylhexanoate. This was taken into consideration in the following calculated analysis figures:

calculated: C, 45.9; H, 5.2; N, 12.5. found: C, 45.9; H, 5.3; N, 12.4.

β-Lactam content: (determined iodometrically) 82%.

EXAMPLE 32

11.0 pts. by wt. of 7-(D-α-amino-phenylacetamido)-3-hydroxymethyl-ceph-3-em-4-carboxylic acid in 100 pts. by vol. of 80 percent strength aqueous THF and 6.1 pts. by wt. of 1-chlorocarbonyl-2-oxo-3-furylideneamino-imidazolidine are reacted as in Example 1.6. and the mixture is worked up. This gives 6.9 pts. by wt. of sodium 7-{D-α-[(2-oxo-3-furyl-ideneamino-imidazolidin-1-yl)-carbonylamino]-phenylacetamido}-3-hydroxymethyl-ceph-3-em-4-carboxylate of decomp. pt. 215°–220° C.

NMR (CD$_3$OD): 7.80 (s, 1H), 7.70 (s, 1H), 6.97 (q, 1H), 5.75 (d, 1H), 5.63 (s, 1H), 5.37 (overlaid by the replaceable protons), 4.40 (s, 2H), 3.95 (s, broad, 4H), the C-2protons are overlaid by the solvent peak (in δ).

EXAMPLE 33

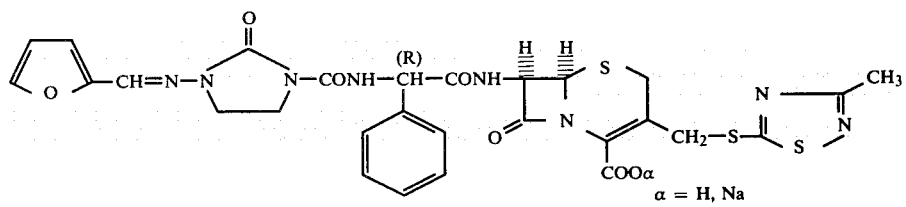

7.5 pts. by wt. of 7-(D-α-amino-phenylacetamido)-3-[(3-methyl-thiadiazol-5-yl)-thiomethyl]-ceph-3-em-4-carboxylic acid in 100 pts. by vol. of 80 percent strength aqueous THF and 6.1 pts. by wt. of 1-chlorocarbonyl-2-oxo-3-furylideneamino-imidazolidine are reacted as in Example 1.6. and the mixture is worked up.

This gives 5.2 pts. by wt. of sodium 7-{D-α-[(2-oxo-3-furylideneamino-imidazolidin-1-yl)-carbonylamino]-phenyl-acetamido}-3-[(3-methyl-thiadiazol-5-yl)-thiomethyl]-ceph-3-em-4-carboxylate of decomp. pt. 210°–215° C.

IR (KBr): 1760, 1720, 1660, 1595, 1525, 1475, 1410, 1275 and 1230 cm$^{-1}$.

NMR (CD$_3$OD): 7.70 (s, 1H), 7.64 (d, 1H), 7.33 (m, 5H), 6.86 (d, 1H), 6.50 (dd, 1H), 5.65 (d, 1H), 5.55 (s, 1H), 4.90 (d, 1H), 4.02 (pseudo q. 2H), 3.85 (s, broad, 4H), 3.4 (overlaid by the solvent peak) and 2.52 (s, 3H) δ.

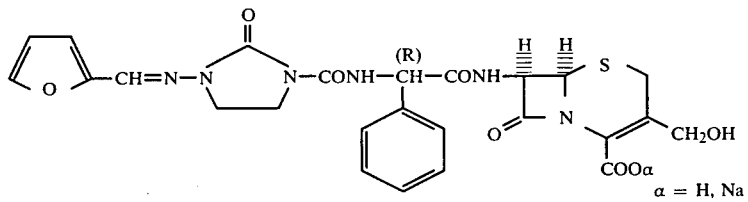

EXAMPLE 34

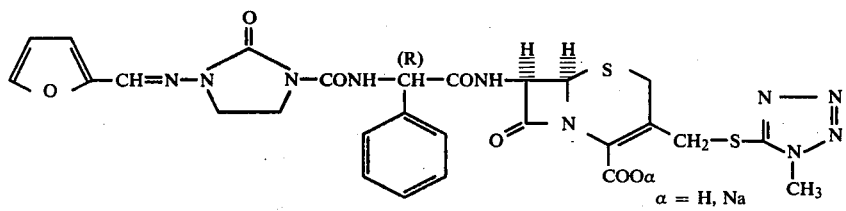

5.0 pts. by wt. of 7-1-(D-α-amino-phenylacetamido)-3-[(1-methyltetrazol-5-yl)-thiomethyl]-ceph-3-em-4-carboxylic acid in 100 pts. by vol. of 80 percent strength aqueous THF and 6.1 pts. by wt. of 1-chlorocarbonyl-2-oxo-3-furylideneaminoimidazolidine are reacted as in Example 1.6 and the mixture is worked up. This gives 3.2 pts. by wt. of sodium 7-{D-α-[(2-oxo-3-furylideneamino-imidazolidin-1-yl)-carbonylamino]-phenylacetamido}-3-[(1-methyl-tetrazol-5-yl)-thiomethyl]-ceph-3-em-4-carboxylate of decomp. pt. 210°–220° C.

IR (KBr): 1760, 1720, 1660, 1610, 1520, 1475, 1410 and 1230 cm$^{-1}$.

NMR (CD$_3$OD): 7.73 (s, 1H), 7.63 (d, 1H), 7.38 (m, 5H), 6.88 (d, 1H), 6.54 (q, 1H), 5.67 (d, 1H), 5.56 (s, 1H), 4.9 (overlaid by the replaceable protons), 4.32 (s, 2H), 3.95 (s, 3H), 3.85 (s, broad, 4H) and 3.45 (overlaid by the solvent peak) δ.

EXAMPLE 34a

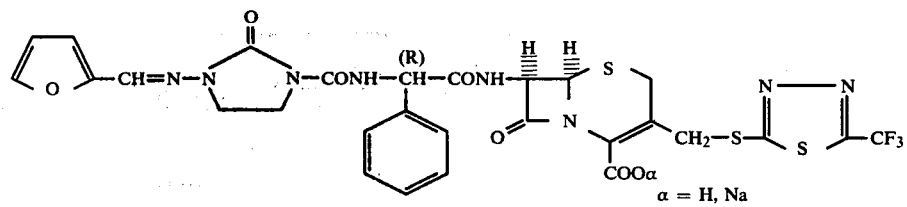

8.0 pts. by wt. of 7-(D-α-amino-phenylacetamido)-3-[(5-trifluoromethyl-1,3,4-thiadiazol-2-yl)-thiomethyl]-ceph-3-em-4-carboxylic acid in 100 pts. by vol. of 80 percent strength aqueous THF and 6.1 pts. by wt. of 1-chlorocarbonyl-2-oxo-3-furylideneamino-imidazolidine are reacted as in Example 1.6. and the mixture is worked up.

This gives 7.8 pts. by wt. of sodium 7-{D-α-[(2-oxo-3-furylideneamino-imidazolidine-1-yl)-carbonylamino]-phenylacetamido}-3-[(5-trifluoromethyl-1,3,4-thiadiazol-2-yl)-thiomethyl]-ceph-3-em-4-carboxylate of decomp. pt. 220° C. with a β-lactam content of 76%.
IR (liquid paraffin): carbonyl range: 1765, 1720, 1660, 1600 and 1530 cm$^{-1}$.

EXAMPLE 35 (A)

(35.1.) Preparation of the 1-alkylideneamino-imidazolidin-2-ones 0.10 mol of 1-aminoimidazolidin-2-one and 50 mg of p-toluenesulphonic acid as well as 15 g of a molecular sieve (4A) are added to a solution of 0.12 mol of the freshly distilled aliphatic aldehyde in 100 ml of abs. acetonitrile. After standing for 3 days at room temperature (the reaction product partially crystallizes out during this period) the molecular sieve is separated off, the reaction mixture is concentrated and the residue is recrystallised (Table 35.1.).

Table for Example 35.1

R—CH=N—(imidazolidin-2-one ring)—NH  (B)

| Example No. | R | Melting point, recrystallised from | Yield | IR (KBr) in cm$^{-1}$ | NMR in ppm (δ) | calculated: found: | C | H | N |
|---|---|---|---|---|---|---|---|---|---|
| 35.1.1 | CH$_3$— | 174–7° Acetone | 19.4% | 3300, 1730, 1690, 1490, 1420, 1270, 1220 | CD$_3$OD: q 6.99 (1H), m 3.62 (4H) d 2.00 (3H) | | 47.23 47.2 | 7.13 7.1 | 33.05 32.7 |
| 35.1.2 | CH$_3$—CH$_2$— | 116–7° Ethyl acetate | 35.3% | 3300, 1740, 1695, 1480, 1415, 1265 | CD$_3$OD: t 7.00 (1H), m 2.40 (2H), pseudo t 1.17 (3H) | | 51.06 51.7 | 7.86 7.9 | 29.77 29.7 |
| 35.1.3 | CH$_3$\\CH—/CH$_3$ | 152–8° Acetonitrile | 45.8% | 3290, 1740, 1700, 1460, 1410, 1260, 1220 | CD$_3$OD: d 6.86 (1H), m 3.60 (4H), sep 2.55 (1H), s 1.16 (3H), s 1.05 (3H) | | 54.18 54.3 | 8.44 8.3 | 27.08 27.9 |

Table for Example 35.1-continued (B)

R—CH=N—N(C=O)NH  (imidazolidinone ring)

| Example No. | R | Melting point, recrystallised from | Yield | IR (KBr) in cm$^{-1}$ | NMR in ppm (δ) | calculated: found: | C | H | N |
|---|---|---|---|---|---|---|---|---|---|
| 35.1.4 | (CH₃)₃C— | 186–8° Isopropanol | 51.9% | 3340, 1740–1690, 1470, 1410, 1250, 1230 | CD₃OD: s 6.90 (1H), m 3.59 (4H), s 1.17 (9H) | | 56.78 56.7 | 8.93 9.0 | 24.83 24.6 |
| 35.1.5 | CH₃—CH=CH— | 209–13° | 83.1% | 3290, 1730, 1700, 1480, 1405, 1255 | CD₃OD: d 7.33 (1H), m 6.25 (2H), m 3.63 (4H), d 1.87 (3H) | | 54.89 54.5 | 7.24 7.1 | 27.43 27.2 |
| 35.1.6 | (CH₃)₂C=CH— | 243–7° | 81.3% | 3200, 3100, 1705, 1405, 1265, 1230 | d₆-DMSO: d 7.53 (1H), s (broad) 7.20 (NH), d 6.05 (1H), m at about 3.6 (4H), s 1.90 (6H) | | 57.46 57.4 | 7.84 7.8 | 25.13 25.1 |
| 35.1.7 | cyclohexenyl— | 145–8° | 61.6% | 3280, 1740–1710, 1405, 1255, 1220 | d₆-acetone: d 7.05 (1H), s 5.69 (2H), m 3.6–3.3 (5H) m at about 2.05 (+ solvent peak) | | 62.15 61.5 | 7.82 6.9 | 21.75 21.8 |
| 35.1.8 | CH₃O—C(CH₃)₂— | 133–4° Acetone | 64.0% | 3400, 3260, 1690, 1440, 1280, 1070 | CD₃OD: s 6.83 (1H), m 3.59 (4H), s 3.49 (3H), s 1.10 (6H) | | 51.87 51.6 | 8.16 8.1 | 22.69 22.6 |

(35.2.) Preparation of the 1-alkylideneamino-3-chlorocarbonyl-imidazolidin-2-ones First 60 mmols of phosgene and then 60 mmols of tributylamine are added to a suspension of 60 mmols of the 1-alkylideneamino-imidazolidinone compound in 100 ml of abs. ethyl acetate at 0°–5°. The mixture is stirred overnight at room temperature and thereafter dry nitrogen is bubbled through for 1 hour. The sparingly soluble acid chlorides are filtered off and further reacted directly. In the case of the more readily soluble acid chlorides (R=CH₃—, CH₃—CH₂ or (CH₃)₂CH—), the reaction mixture is concentrated and the residue is used for the further reactions.

The acid chlorides are characterised by the appearance of the COCl band at about 1800 cm$^{-1}$ (Table 35.2.).

Table for Example 35.2

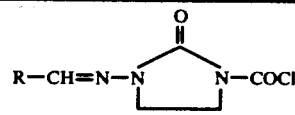
R—CH=N—N(C=O)N—COCl

| Example No. | R | IR (Nujol) in cm$^{-1}$ |
|---|---|---|
| 35.2.1 | CH₃— | 1820 |
| 35.2.2 | CH₃—CH₂— | 1800 |
| 35.2.3 | (CH₃)₂CH— | 1820 |

Table for Example 35.2-continued

R—CH=N—N(C=O)N—COCl

| Example No. | R | IR (Nujol) in cm$^{-1}$ |
|---|---|---|
| 35.2.4 | (CH₃)₃C— | 1800 |
| 35.2.5 | CH₃—CH=CH— | 1810 |
| 35.2.6 | (CH₃)₂C=CH— | 1810 |
| 35.2.7 | cyclohexenyl— | 1820 |

(35.3.) Preparation of the acylated ampicillins, amoxicillins, dephaloglycines and 7-methoxy-cephaloglycines 15–50 mmols of ampicillin trihydrate, amoxicillin trihydrate, cephaloglycine dihyrate or 7-methoxycephaloglycine trifluoroacetate are suspended in 100–150 ml of 80% strength aqueous THF and 4% strength sodium hydroxide solution is added at 5° until the pH remains constant at 8.1. The equivalent amount of acid chloride is then added and 2% strength sodium hydroxide solution is added dropwise until the pH remains constant at 7.5. The amount of undissolved material is filtered off, 100 ml of water are added to the filtrate and the THF is stripped off. The aqueous phase is extracted with 100 ml of ethyl acetate and the extract is cooled to 5°, covered with a layer of 100 ml of ethyl acetate and brought to pH 1.8 by adding dropwise 0.1 N hydrochloric acid. During this procedure, some of the acid precipitates (A) and some dissolves in the ethyl acetate (B). (The particular quantitative proportion depends on the solubility of the corresponding derivative).

(A) is dissolved in methanol, the equivalent amount of sodium caprylate solution is added and (A) is precipitated as the sodium salt by pouring the mixture into abs. ether containing 5% of methanol.

(B) is dried over magnesium sulphate, sucked up and reacted with sodium caprylate solution in the same manner as (A).

The sodium salts are freed from ether under a high vacuum and then dried in ethyl acetate over $P_2O_5$.

The $\beta$-lactum content was determined from the NMR spectra (Table 35.3.).

Table for Example 35.3

$$R-CH=N-N\underset{\phantom{X}}{\overset{\overset{\displaystyle O}{\|}}{\diagdown}}N-CO-R'$$

| Example No. | R | R' | Yield | β-Lactam content | IR (KBr) in cm$^{-1}$ | NMR (CD$_3$OD) in ppm (δ) |
|---|---|---|---|---|---|---|
| 35.3.1 | CH$_3$— | -ampi | 44.0% | 85% | 3420, 1760, 1720, 1630, 1600, 1520 | m 7.6 (5H), s 5.58 (1H), AB 5.45 (2H), s 4.15 (1H), m 3.8 (4H), d 2.02 (3H), s 1.57 (3H), s 1.49 (3H) |
| 35.3.2 | CH$_3$— | -amoxi | 76.6% | 60% | 3320, 1760, 1665, 1600, 1510, 1260 | A$_2$B$_2$ + q 7.20 and 6.72 (5H), m 5.4 (3H), s 4.13 (1H), m at about 3.5 (4H), d 2.00 (3H), s 1.50 (3H) |
| 35.3.3 | CH$_3$— | -cephgly | 74.6% | 80% | 3420, 3380, 1760, 1720, 1665, 1600, 1410, 1380, 1220 | m at about 7.25 (5H), q 7.20 (1H), s 5.58 (1H), d 4.9 (1H), AB ~ 4.85 (2H), m 3.75 (4H), AB 3.3 (2H), s 2.00 (3H), d 8.01 (3H) |
| 35.3.4 | CH$_3$—CH$_2$— | -ampi | 29.7% | 75% | 3380, 1765, 1730, 1670, 1600, 1520, 1410 | m 7.3 (5 + 1H), m 5.5 (3H), s 4.1 (1H), m 3.7 (4H), m 2.4 (2H), s 1.55 (3H), S 1.50 (3H) |
| 35.3.5 | CH$_3$—CH$_2$— | -chephygly | 44.0% | 80% | 3310, 1765, 1725, 1605, 1530, 1410, 1220 | m 7.35 (5H), t 7.15 (1H), d 5.67 (1H), s 5.58 (1H), d 4.92 (1H), AB 4.86 (2H), m 3.8 (4H), AB ~ 3.3, m 2.4 (2H), s 2.00 (3H) |
| 35.3.6 | CH$_3$\\<br>  CH—<br>CH$_3$/ | -ampi | 80.1% | 90% | 3400, 1760, 1720, 1660, 1600, 1520, 1410, 1205 | m 7.4 (5H), d 7.03 (1H), s 5.60 (1H), AB 5.45 (2H), s 4.15 (1H), m 3.77 (4H), septet 2.59 (1H), s 1.56 (3H), s 1.50 (3H), d 1.12 (6H) |
| 35.3.7 | CH$_3$\\<br>CH$_3$—C—<br>CH$_3$/ | -ampi | 93.3% | 90% | 3300–3500, 1760, 1725, 1665, 1600, 1520, 1410 | m at about 7.35 (5H), s 7.08 (1H), s 5.58 (1H), AB 5.45 (2H), s 4.15 (1H), m 3.76 (4H), s 1.58 (3H), s 1.50 (3H), s 1.15 (9H) |
| 35.3.8 | CH$_3$\\<br>CH$_3$—C—<br>CH$_3$/ | -amoxi | 97.1% | 90% | 3310, 1760, 1730, 1670, 1610, 1410 | A$_2$B$_2$ 7.25 and 6.75 (4H), s 7.04 (1H), m 5.42 (3H), s 4.12 (1H), m 3.75 (4H), s 1.55 (3H), s 1.48 (3H), s 1.12 (9H) |
| 35.3.9 | CH$_3$\\<br>CH$_3$—C—<br>CH$_3$/ | -cephygly | 90.9% | 80% | 3300, 1760, 1720, 1660, 1600, 1400, 1260 | m at about 7.35 (5H), s 7.06 (1H), d 5.56 (1H), s 5.58 (1H), d 4.90 (1H), AB 4.85 (2H), m 3.75 (4H), AB ~ 3.3, s 2.00 (3H), s 1.14 (9H) |
| 35.3.10 | CH$_3$—CH=CH— | -ampi | 81.5% | 85% | 3320, 1765, 1715, 1670, 1600, 1515, 1410, 1265, 1215 | m 7.35 (5 + 1H), m 6.27 (2H), s 5.55 (1H), AB 5.42 (2H), s 4.22 (1H), m 3.75 (4H), m 1.84 (3H), s 1.54 (3H), s 1.46 (3H) |
| 35.3.11 | CH$_3$—CH=CH— | -amoxi | 57.3% | 90% | ~3400, 1760, 1720, 1660, 1600, 1410, 1260, 1210 | pseudo d 7.43 (1H), A$_2$B$_2$ 7.22 and 6.77 (4H), d 6.28 (2H), AB + s 5.50–5.33 (3H), s 4.12 (1H), m 3.78 (4H), m 1.87 (3H), s 1.54 (3H), s 1.48 (3H) |
| 35.3.12 | CH$_3$—CH=CH— | -cephgly | 88.2% | 80% | 3440, 1760, 1720, 1665, 1600, 1425, 1410, 1265, 1220 | m at about 7.35 (5 + 1H), dd 6.26 (2H), d 5.63 (1H), s 5.52 (1H), m at about 4.85 (3H), m 3.58 (4H), AB~3.3, s 1.98 (3H) |
| 35.3.13 | CH$_3$\\<br>  C=CH—<br>CH$_3$/ | -ampi | 87.2% | 90% | 3400, 1760, 1720, 1660, 1600, 1515, 1410, 1260, 1220 | d 7.63 (1H), m 7.3 (5H), d 6.05 (1H), s 5.58 (1H), AB 5.38 (2H), s 4.08 (1H), s 1.88 (6H), s 1.55 (3H), s 1.46 (3H) |
| 35.3.14 | CH$_3$\\<br>  C=CH—<br>CH$_3$/ | -cephgly | 75.9% | 80% | 3420, 1755, 1720, 1665, 1605, 1920, 1410, 1370, 1270, 1220 | d 7.65 (1H), m 7.3 (5H), d 6.05 (1H), d + s 5.5 (2H), m 4.85 (3H), m 3.8 (4H), AB ~ 3.3 (covered), s 1.98 (3H), s 1.88 (6H) |

Table for Example 35.3-continued

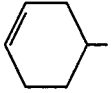

| Example No. | R | R' | Yield | β-Lactam content | IR (KBr) in cm⁻¹ | NMR (CD₃OD) in ppm (δ) |
|---|---|---|---|---|---|---|
| 35.3.15 | cyclohexenyl | -ampi | 92.3% | 90% | 3400, 3300, 1799, 1720, 1600, 1919, 1405, 1270, 1219 | m 7.3 (5H), d 7.02 (1H), s (broad), 5.67 (2H), s 5.58 (1H), AB 5.45 (2H), s 4.13 (1H), m 3.8 (5H), m 2.6 (2H?), m 2.15 (4H), s 1.58 (3H), s 1.50 (3H) |
| 35.3.16 | cyclohexenyl | -cephgly | 79.3% | 85% | 3280, 1760, 1715, 1660, 1600, 1920, 1410, 1270, 1220 | m 7.35 (5H), d 7.08 (1H), m 5.75–5.55 (4H), d 4.9 (1H), AB 4.88 (2H), m 3.75 (5H), AB ~ 3.3 (covered), m + s 2.15 and 2.00 (5H?) |
| 35.3.17 | CH₃ | 7-methoxy-cephgly. | 61.2% | 85% | 3430, 3380, 2850, 1760, 1720, 1665, 1600, 1430, 1385 | m at about 7.25 (5H), d 7.20 (1H), s 5.58 (1H), s 9.9 (1H), a,b ~ 4.84 (2H), s 9.45 (3H), m 3.75 (4H), a,b 3.3 (2H), s 2.05 (3H), d 2.00 (3H) |
| 35.3.18 | (CH₃)₂C=CH | 7-methoxy-cephgly. | 60.8% | 80% | 3425, 2855, 1765, 1720, 1660, 1600, 1510, 1410, 1385 | d 7.65 (1H), m 7.3 (5H), d 6.05 (1H), s 5.6 (1H), m 4.9 (3H), m 3.85 (4H), s 3.45 (3H), a,b ~ 3.3 (2H) (covered), s 2.00 (3H), s 1.9 (6H) |

EXAMPLE 36

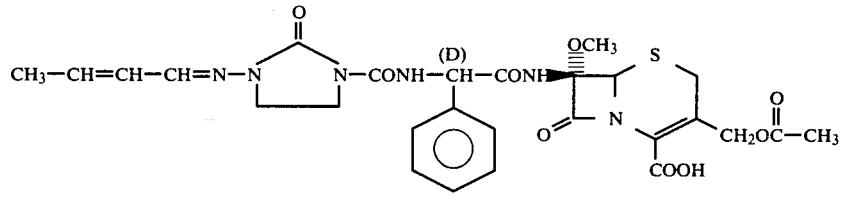

1.65 pts. by wt. of 7-methoxy-7-(D-α-amino-phenylacetamido)-3-acetoxymethyl-ceph-3-em-carboxylic acid trifluoroacetate are dissolved in 120 parts by vol. of 80% strength aqueous THF and the solution is adjusted to a pH value of 7.5 with dilute NaOH, whilst cooling with ice. 0.65 part by wt. of 1-chlorocarbonyl-2-oxo-3-but-2-enylideneamino-imidazolidine in 150 parts by wt. of THF are added to this solution at 0° C., whilst stirring; at the same time, enough dilute NaOH to keep the pH value at ~7.5 and a further 40 parts of vol. of water are added.

After one hour, the clear solution is concentrated to ~100 parts by vol. and extracted twice with acetic acid ethyl ester and the aqueous phase is then acidified to pH 2.0 with dilute HCl (cooling with ice) and extracted several times with ethyl acetate/acetone.

The organic phases are dried over MgSO₄ and slowly concentrated; during this procedure, 1.2 parts by wt. of 7-methoxy-7-{D-α-[(2-oxo-3-but-2-enylideneamino-imidazolidin-1-yl)-carbonylamino]-phenylacetamido}-3-acetoxymethyl-ceph-3-em-4-carboxylic acid crystallise out; β-lactam content >85%.

IR spectrum (KBr) 3396, 2913, 2720, 1780, 1675, 1459, 1378, 1267, 973, 875 and 720;

NMR spectrum (acetone+10% H₂O) m 7.5 (1), s 7.3 (5H), m 6.2 (2H), s 5.5 (1H), s 5.0 (1H), A,B 4.8 (2H), m 3.7 (4H) (covered), s 3.45 (3H),

EXAMPLE 37

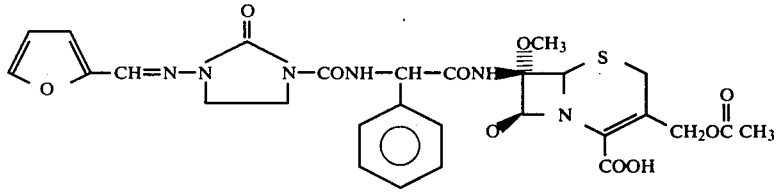

(A) 1.1 parts by wt. of 7-methoxy-7-(D-α-amino-phenylacetamido)-3-acetoxymethyl-ceph-3-em-carboxylic acid trifluoroacetate are dissolved in 60 parts by vol. of 80% strength aqueous THF, the solution is brought to pH=7.5 with dilute NaOH, whilst cooling with ice, and 0.5 part by wt. of solid 1-chlorocarbonyl-2-oxo-3-furfurylidine amino-imidazoline is added at 0° C., whilst stirring. The pH value is kept at 7.5 with dilute NaOH. After half an hour, the reaction has ended and the mixture is worked up as described under Example 1.3 or 6.4.

This gives 0.8 part by wt. of crystalline 7-methoxy-7-{D-α-[(2-oxo-3-furfurylideneamino-imidazolidin-1-yl)-carbonylamino]-phenylacetamido}-3-acetoxymethyl-ceph-3-em-4-carboxylic acid; β-lactam content 85%.

100 MHz-1H-NMR spectrum (acetone (D₂O)

s 2.0 3H, A,B 3.3 2H, s 3.45 3H, s 3.8 2H, A,B 4.8 2H, s 4.9 1H,
s 5.7 1H, q 6.5 1H, d 6.8 1H, s 7.4 5H, d 7.55 1H and s 7.7 1H.

(B) Alternatively, this compound can also be obtained in the following manner:

1. 30.5 Parts by wt. of the acid prepared according to Example 6.4 are esterified on the carboxyl group with 15.5 parts by wt. of biphenyldazomethane.

600 Parts by vol. of THF are used as the solvent. After 12 hours, the solution is concentrated and washed with n-pentane until a colourless substance remains. This procedure gives 37.2 parts by wt. of biphenylmethyl-7-methoxy-7-{D-2-[(2-oxo-3-furfurylideneamino-imidazolidin-1-yl)-carbonylamino]-phenylacetamido}-3-acetoxymethyl-ceph-3-em-4-carboxylate.

2. 500 parts by vol. of absolute THF are added to 34.1 parts by wt. of this compound under nitrogen; this mixture is cooled to $-65°$ C. and a solution of 1.35 parts by wt. of LiH in 200 parts by vol. of methanol is first added dropwise, and immediately thereafter 7.16 parts by wt. of tert.-butyl hypochlorite are added dropwise.

The mixture is subsequently stirred for a further 20 minutes, it being allowed to come to $-40°$ C. 72 parts by vol. of glacial acetic acid and 7.2 parts by wt. of triethyl phosphite are then added and the mixture is subsequently allowed to warm to room temperature.

The solution is added to 4 l of acetic acid ethyl ester and this mixture is washed successively with one liter each of 5% strength NaCl solution, 10% strength $Na_2S_2O_3$ solution, saturated $NaHCO_3$ solution, citric acid solution, water and saturated NaCl solution.

After drying over $MgSO_4$, the solution is concentrated and the product is reprecipitated from $CH_2Cl_2$ (n-pentane). This product is chromatographed on 600 parts by wt. of silica gel with $CH_2Cl_2$/ethyl acetate.

This gives, finally, 25.3 parts by wt. of the corresponding 7-methoxy compound.

3. The removal of the ester protective group is effected with trifluoroacetic acid/anisole, as is described, for example, in DOS (German Published Specification) No. 2,555,159.

The acid is finally obtained in a purity comparable to that under 37 A.

(C) Furthermore, this compound can also be prepared in the following manner:

48.8 Parts by wt. of 7-[D-α-[(2-oxo-3-furfurylideneamino-imidazolidin-1-yl)-carbonylamino]-phenylacetamido]-3-acetoxymethyl-ceph-3-em-4-carboxylic acid in anhydous tetrahydrofurane are added to a solution, cooled to $-70°$ C. of 1,000 parts by volume of anhydrous tetrahydrofurane, 2.54 parts by wt. of lithium hydride and 1,000 parts by volume of abs. methanol.

8.68 Parts by wt. of t-butyl hypochlorite are then added immediately to the clear solution and the mixture is subsequently stirred for 20 minutes at $-70°$ C.

The reaction solution is then added to water, whilst simultaneously adding half-concentrated hydrochloric acid, so that the pH value is about 7.

After clarifying with active charcoal, the solution is concentrated in vacuo and covered with a layer of ethyl acetate, the pH value is adjusted to 7.5 and the aqueous phase is separated off and extracted again with ethyl acetate.

The aqueous phase is then covered with a layer of ethyl acetate and the pH value is adjusted to 1.8, whilst stirring. After separating off the organic phase and extracting it a further two times with ethyl acetate, the organic phases are dried over $MgSO_4$ and concentrated in vacuo. The white precipitate which has separated out is filtered off, washed thoroughly with ether and dried in vacuo in a disiccator. Yield: 39 parts by wt. (76%).

In the thin layer chromatogram, the compound appears uniform, with virtually the same Rf value as the corresponding compound without a methoxy group.

(Running agent: 200 ml of n-butyl acetate, 36 ml of n-butanol and 100 ml of acetic acid (treated with phosphate buffer of pH 6))

100 MHz-$^1$H-NMR spectrum (acetone D$_2$O): s 2.0 3H, a,b 3.3 2H, s 3.45 3H, s 3.8 2H, a,b 4.8 2H, s 4.9 1H, s 5.7 1H, g 6.5 1H, d 6.8 1H m 7.4 5H d 7.55 1H and 5 7.7 1H.

The compounds which follow can be prepared by the procedure of Example 37A), B) or, advantageously, also c). If the procedure of Example 37 B) is followed, the protective group introduced is removed with hydrogen in the presence of a platinum catalyst.

EXAMPLES 38–45

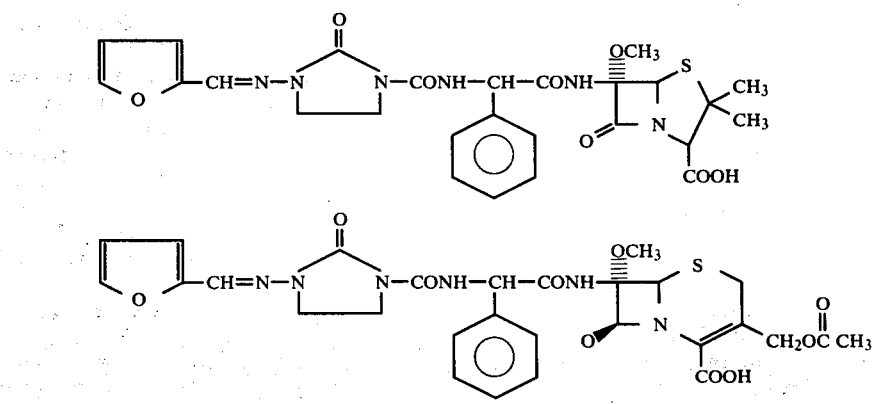

-continued

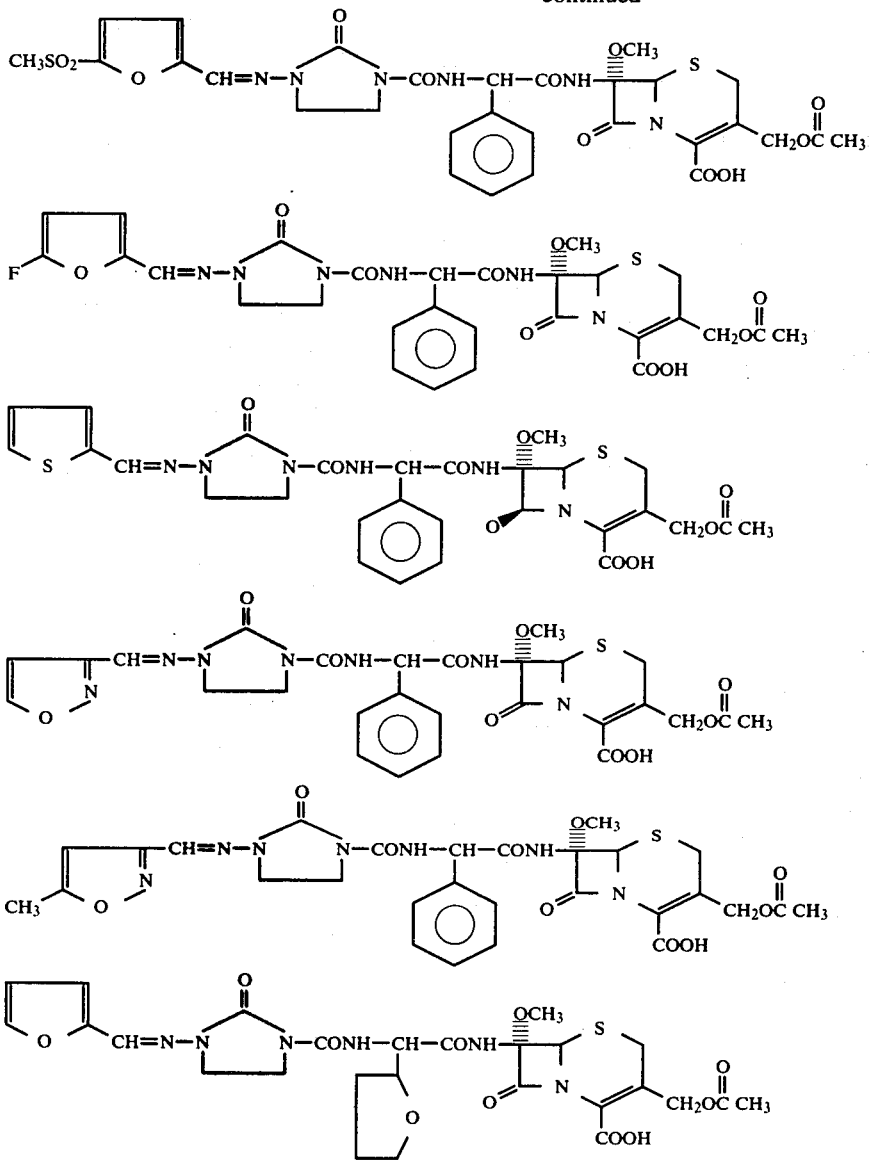

EXAMPLES 46

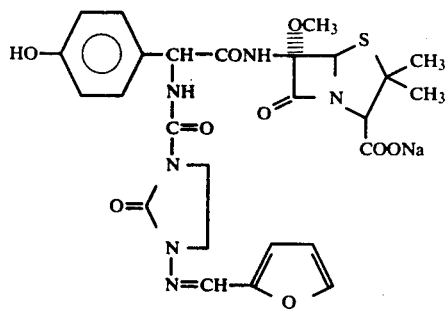

8.1 Parts by wt. of sodium 6-{-D-α-[2-oxo-3-(furfurylideneamino)-imidazolidin-1-yl)-carbonylamino}-p-hydroxyphenylacetamido]-penicillanate, dissolved in abs. methanol, are added to a solution, cooled out of −70° C., of 150 parts by vol. of THF/100 parts by vol. of methanol (both anhydrous) and 0.52 part by wt. of LiH in the course of 5 minutes. 3.1 Parts by wt. of t-butyl hypochlorite are then added at the same temperature and the mixture is subsequently stirred for 2 hrs. at −70° to −60° C.

The working up is initially as described in Example 1.

The 6-methoxy-penicillic acid then contained in the ethyl acetate, by acid extraction at pH 1.8, is now converted into the sodium salt in the following manner:

A layer of water is introduced below the ethyl acetate solution, the pH value is adjusted to 7.2 with dilute sodium hydroxide solution, the aqueous phase is separated off and the procedure is repeated.

The combined aqueous phases are extracted with ether and the aqueous phase is finally subjected to freeze-drying.

Yield: 6.2 parts by wt. (73%)

In the thin layer chromatogram, the white salt is uniform and has a slightly higher Rf value than the corresponding non-methoxylated starting material.

100 MHz - ¹H - NMR spectrum (d-acetone/D₂O): s 1.1 3H, s 1.4 3H, s 3.5 3H, s 3.95 4H, s 4.1 1H, s 5.5 1H, s 5.55 1H, m 6.5 1H, d 6.85 1H, m 6.7–7.05 3H, m 7.25–7.55 2H, d 7.7 1H and s 7.8 1H.

IR spectrum, bands [cm⁻¹]: 3418, 1762, 1721, 1667, 1608, 1526, 1476, 1415, 1272, 1234, 1096, 1015, 931, 882 and 741.

EXAMPLE 47

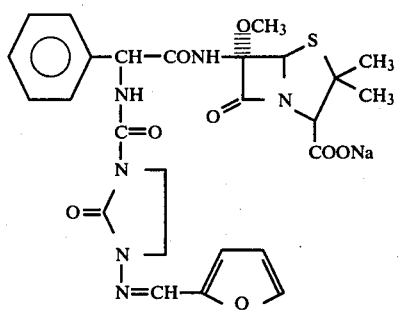

4 Parts by wt. of 6-{D-α-[(2-oxo-3-furfurylideneaminoimidazolidinin-1-yl)-carbonaylamino]-phenylacetamido}-penicillanic acid, 0.23 part by wt. of LiH, 0.78 part by wt. of t-butyl hypochlorite and 50 parts by volume each of metanol and tetrahydrofurane are reacted in the manner described in Example 1. The reaction time is 2 hrs.

Yield: 3.7 parts by wt. (80%)

60 MHz ¹H-NMR sectrum (d-acetone/D₂O): s 0.95 3H, s 1.35 3H, s 3.53 3H, s 3.95 4H, s 5.6 1H, s 5.65 1H, g 6.6 1H, d 6.9 1H and multiplet 7.3–7.8 7H.

The compound is uniform in the thin layer chromatogram.

EXAMPLE 48

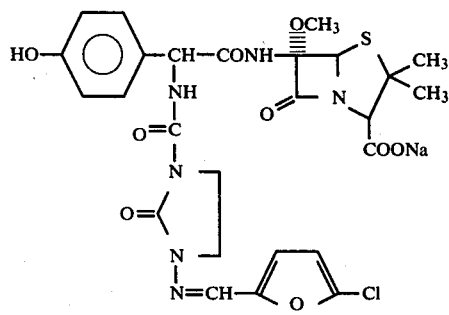

9.1 Parts by wt. of 6-{D-α-[(2-oxo-3-{5-chlorofurylideneamino}-imidazolidin-1-yl)-carbonylamino]-p-hydroxyphenylacetamido{-penicillanic acid, 0.5 part by wt. of LiH and 3.3 parts by wt. of t-butyl hypochlorite in methanol and THF are reacted as in Example 1.

Yield: 6.7 parts by wt. (68%). A uniform compound according to thin layer chromatography.

NMR spectrum (in d-acetone/D₂O):
s 1.0 3H, s 1.35 3H, s 3.5 3H, s 3.95 4H, s 4.05 1H, s 5.5 1H, s 5.53 1H, d 6.5 1H, m 6.8–7.0 3H, m 7.2–7.55 2H and s 7.8 1H.

EXAMPLE 49

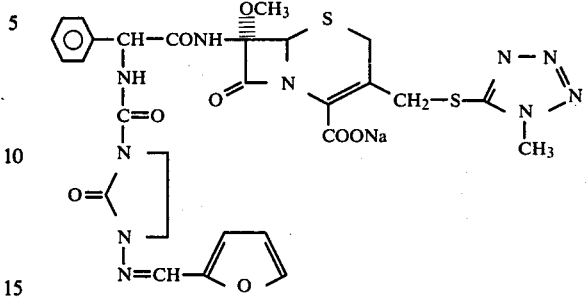

This compound is obtained when (a) the compound from Example 37 is treated with an equimolar amount of 1-methyltetrazole-5-thiol in an aqueous solution at a pH value of 6.5 for 3 hrs. at 70° C., or (b) the compound from Example 8.4 is methoxylated directly according to Example 37 C.

NMR spectrum: (d-acetone/D₂O): s 3.4 3H, s 3.55 2H, broad s 3.85 4H, s 3.95 3H, s 4.4 2H, s 4.9 1H, s 5.7 1H, g 6.5 1H, d 6.8 1H, m 7.4 5H, d 7.55 1H and s 7.7 1H.

EXAMPLE 50

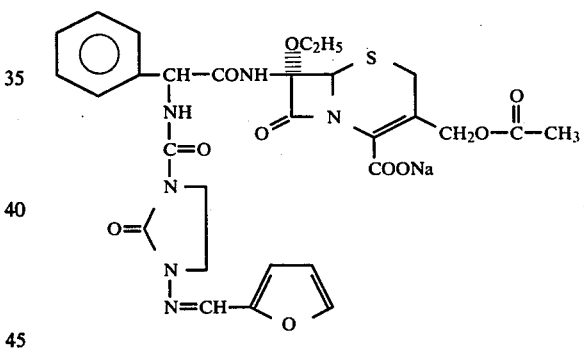

The above compound is prepared from the following amounts of substances in the manner described in Example 46: 7 Parts by wt. of 7-{D-α-[(2-oxo-3-furylideneamino-imidazolidin-1-yl)-carbonylamino]-phenylacetamido}-3-acetoxy-methyl-ceph-3-em-4-carboxylic acid and 0.36 part by wt. of LiH in 150 parts by vol. of abs. ethanol, 1.25 parts by wt. of t-butyl hypochlorite and 100 parts by vol. of THF.

The reaction time is 2 hrs. at −50° to −65° C.

Yield: 4.8 parts by wt. (70%)

According to thin layer chromatography, the compound is uniform and has a higher R$_f$ (more lipophilic) than the starting material and also than the compound from Example 37.

The NMR spectrum is as for the compound from Example 37, except that there is an additional triplet (3H) at δ=1.3 and instead of the singlet at δ=3.5 there is now a quartet (2H) which, however, is indistinct due to overlaying.

EXAMPLE 51

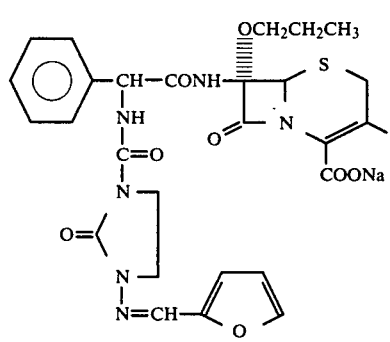

9.15 Parts by wt. of 7-{D-α-[(2-oxo-3-furylideneamino-imidazolidin-1-yl)-carbonylamino]-phenylacetamido}-3-acetoxymethyl-ceph-3-em-4-carboxylic acid and 0.5 part by wt. of LiH, dissolved in 250 parts by vol. of n-propanol, whilst warming, 1.6 parts by wt. of t-butyl hypochlorite and 150 parts by vol. of THF are reacted for 2 hrs. at −60° C. according to Example 46.

Yield: 8 parts by wt. (77%).

Thin layer chromatography: uniform, significantly higher $R_f$ value than the starting material.

NMR: similar change as in the transition from the compound from Example 37 → the compound from Example 50.

EXAMPLE 52

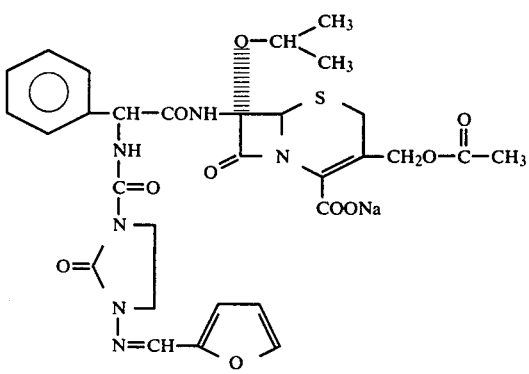

The preparation is as in Example 51, except that the alcoholate solution is prepared beforehand from i-propanol and BuLi.

The reaction time is about 3 hrs. at −55° C.

EXAMPLE 53

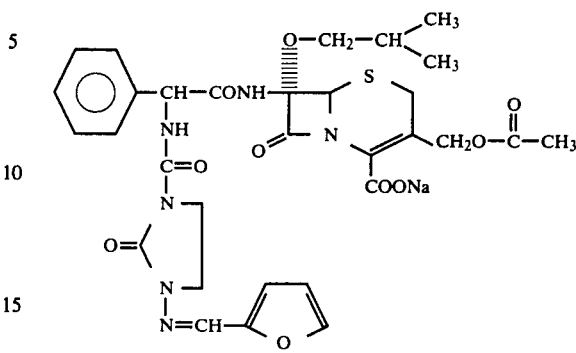

The preparation is analogous to Example 52, except that i-butanol is used instead of i-propanol.

The reaction time is 4 hrs. at −55° C.

EXAMPLE 54

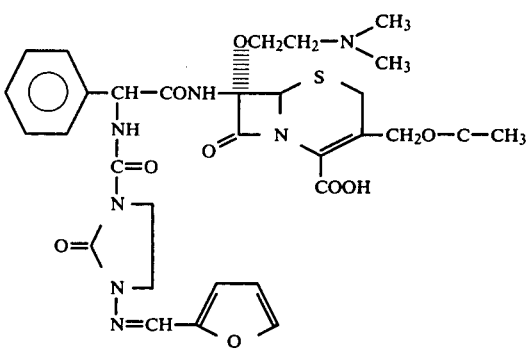

200 Parts by vol. of abs. THF and 150 parts by vol. of freshly distilled 2-dimethylaminoethanol are initially introduced, under nitrogen, and 39 parts by vol. of a 15% strength solution of n-butyllithium in n-hexane are added dropwise (together with 20 parts by vol. of THF). 9.8 Parts by wt. of 7-{D-α-[(2-oxo-3-furylideneamino-imidazolidin-1-yl)-carbonylamino]-phenylacetamido}-3-acetoxymethyl-cephen-3-em-4-carboxylic acid, dissolved in 100 parts by vol. of THF are added to this solution, cooled to −70° C. Finally, 1.9 parts by vol. of t-butyl hypochlorite are slowly added dropwise and the mixture is subsequently stirred for 3 hrs. at −60° C.

The reaction solution is then poured into 200 ml of water, the organic impurities are extracted several times with ethyl acetate at pH 7–7.5, the aqueous phase is then slowly acidified to pH 4.5–4.7 and the precipitate is filtered off and washed thoroughly with acetone/H₂O.

After drying, 5.7 g (51%) of the desired compound are obtained.

What is claimed is:

1. A cephalosporin compound of the formula

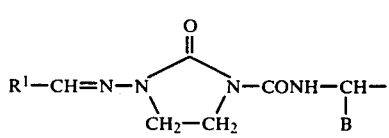

-continued

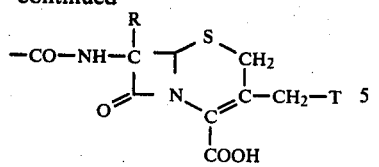

in which
R is alkoxy having 1 to 4 carbon atoms or —OCH₂CH₂N(CH₃)₂,
R¹ is phenyl optionally substituted by halogen, alkyl having 1 to 4 carbon atoms, alkoxy having 1 to 4 carbon atoms, nitro, cyano, alkylsulphonyl having 1 to 4 carbon atoms or CH₃OOC—; furyl or thienyl optionally substituted by halogen, NO₂, alkyl or alkoxycarbonyl having 1 to 4 carbon atoms, or CH₃COOCH₂—; pyridyl; optionally substituted cyclic alkyl or alkenyl having up to 7 carbon atoms; or optionally substituted alkyl or alkenyl having up to 4 carbon atoms,
B is phenyl, hydroxyphenyl or cyclohexadienyl,
T is hydrogen, O—CO—CH₃, hydroxyl, or thiadiozolylthio or tetrazolylthio optionally substituted by alkyl having 1 to 4 carbon atoms or by CF₃, or a salt or hydrate thereof.

2. A compound as claimed in claim 1, in the form of the free acid.
3. A compound as claimed in claim 1, in which R is methoxy.
4. A compound as claimed in claim 1 in which R¹ is phenyl optionally substituted by fluorine, chlorine, bromine, methyl, methoxy, nitro, cyano or methylsulphonyl; furyl or thienyl substituted in the 4- or 5-position by chlorine, bromine, NO₂, alkyl or alkoxycarbonyl having 1 to 4 carbon atoms or CH₃ COOCH₂—; the furyl and thienyl ring being bonded in the 2- or 3- position; pyridyl -3; cyclohexenyl; or alkyl or alkenyl having up to 4 carbon atoms and being optionally substituted by halogen or alkoxy having a 1 to 4 carbon atoms; and B is phenyl, p- hydroxyphenyl or cyclohexa -1,4-dien-1-yl.
5. A compound according to claim 1 of the formula

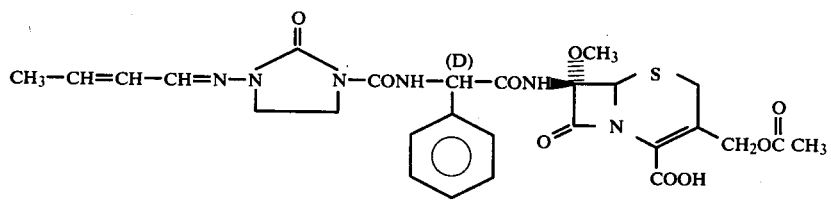

or a salt or hydrate thereof.
6. A compound of the formula

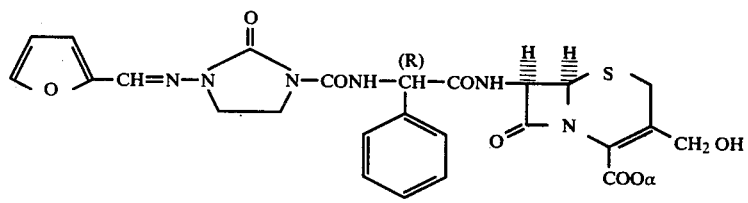

wherein Q is H or Na, or a hydrate thereof.
7. A compound according to claim 1 of the formula

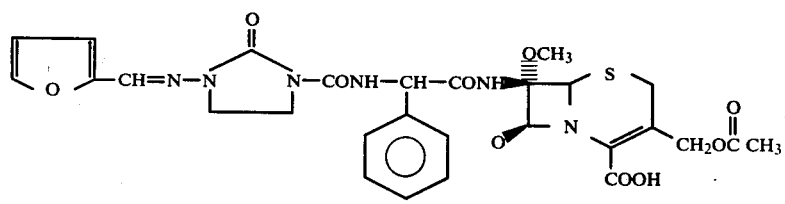

or a salt or hydrate thereof.
8. A compound according to claim 1 of the formula

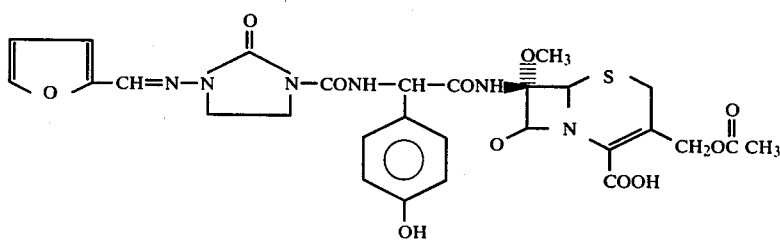

or a salt or hydrate thereof.
9. A compound according to claim 1 of the formula

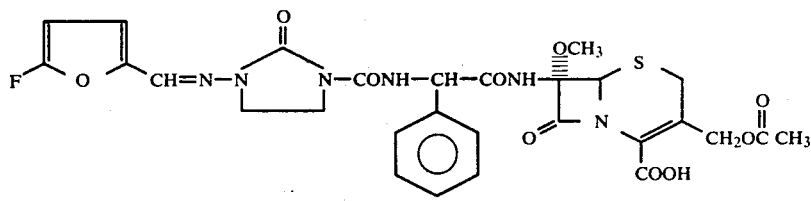

or a salt or hydrate thereof.

10. A compound according to claim 1 of the formula

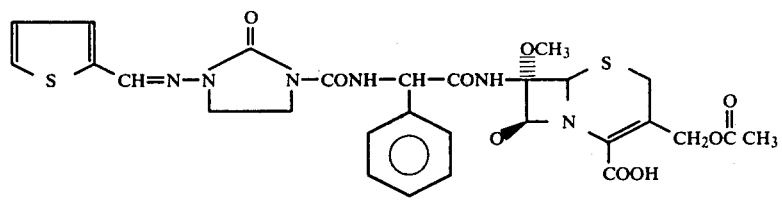

or a salt or hydrate thereof.

11. A compound according to claim 1 of the formula

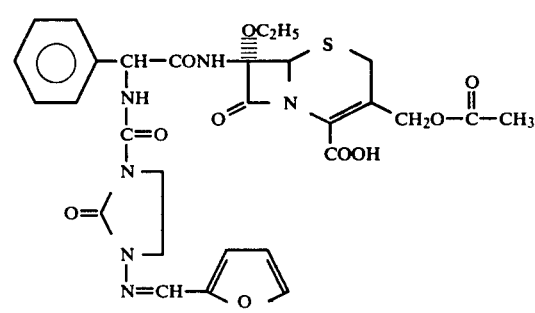

or a salt or hydrate thereof.

12. A compound according to claim 1 of the formula

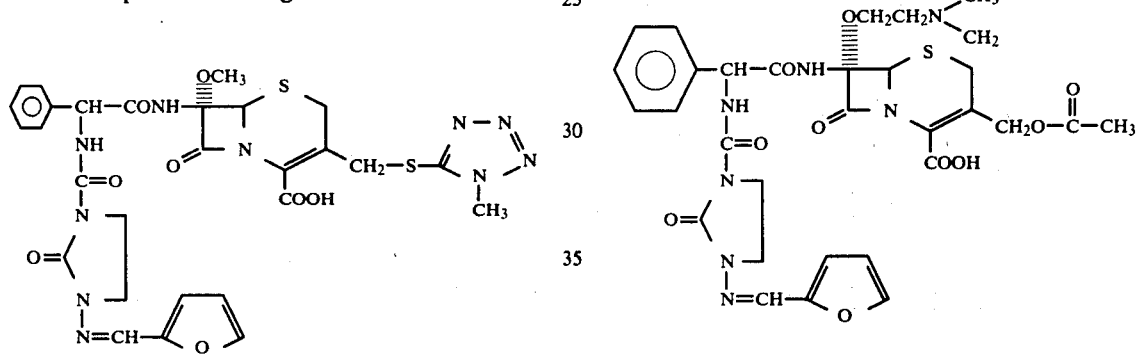

or a salt or hydrate thereof.

13. A compound according to claim 1 of the formula or a salt or hydrate thereof.

14. An antibacterial and growth promoting composition containing as an active ingredient an antibacterial or growth promoting amount of a compound or salt according to claim 1 in admixture with a diluent.

15. An antibacterial composition in dosage unit form comprising a compound or salt according to claim 1.

16. A method of combating bacterial diseases in human and non-human animals which comprises administering to the animals an antibacterially effective amount of a compound or salt according to claim 1.

17. A medicament animal fodder comprising an effective amount of compound or salt according to claim 1 in admixture with a nutritious material.

18. A method of promoting the growth of animals which comprises feeding said animals a growth promoting amount of a compound or salt according to claim 1.

19. A compound of the formula

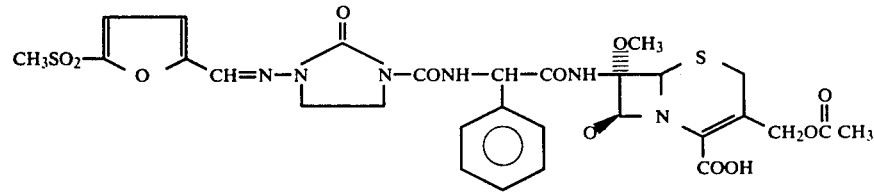

or a salt or hydrate thereof.

20. A compound of the formula

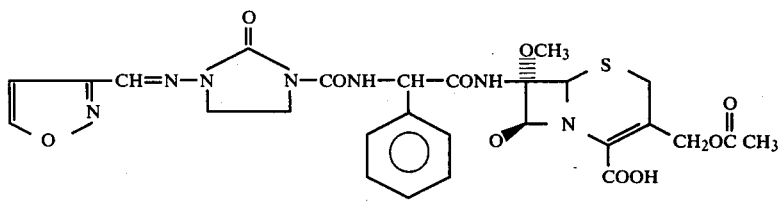
or a salt or hydrate thereof.
21. A compound of the formula
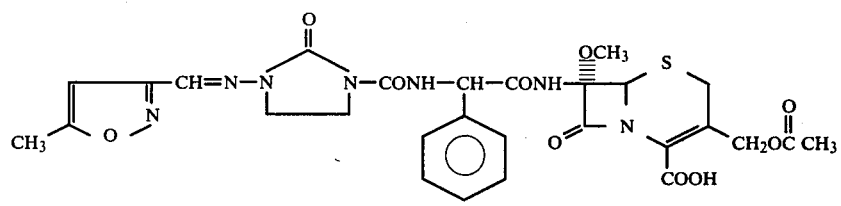
or a salt or hydrate thereof.
22. A compound of the formula
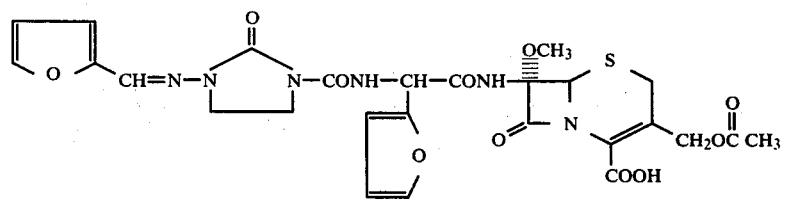
or a salt or hydrate thereof.
* * * * *

UNITED STATES PATENT AND TRADEMARK OFFICE
CERTIFICATE OF CORRECTION

PATENT NO. : 4,200,576

DATED : April 29, 1980

INVENTOR(S) : Peter Feyen et al

It is certified that error appears in the above–identified patent and that said Letters Patent are hereby corrected as shown below:

| COLUMN | LINE | |
|---|---|---|
| 116 | 42 | insert --effective-- before "amount". |

Signed and Sealed this

Ninth Day of September 1980

[SEAL]

Attest:

SIDNEY A. DIAMOND

Attesting Officer

Commissioner of Patents and Trademarks